US011839759B2

(12) United States Patent
Finkelstein et al.

(10) Patent No.: US 11,839,759 B2
(45) Date of Patent: Dec. 12, 2023

(54) SYSTEMS AND METHODS FOR MANAGED TRAINING AND REHABILITATION VIA ELECTRICAL STIMULATION

(71) Applicant: NEURO20 TECHNOLOGIES CORP., Tampa, FL (US)

(72) Inventors: Michael Howard Finkelstein, Tampa, FL (US); Dennis Michael Schmitt, Tampa, FL (US); Jana Schmitt, Tampa, FL (US)

(73) Assignee: NEURO20 TECHNOLOGIES CORP., Tampa, FL (US)

( * ) Notice: Subject to any disclaimer, the term of this patent is extended or adjusted under 35 U.S.C. 154(b) by 0 days.

(21) Appl. No.: 18/187,624

(22) Filed: Mar. 21, 2023

(65) Prior Publication Data
US 2023/0226345 A1 Jul. 20, 2023

Related U.S. Application Data

(63) Continuation-in-part of application No. PCT/US2021/051149, filed on Sep. 20, 2021.
(Continued)

(51) Int. Cl.
*A61N 1/04* (2006.01)
*A61N 1/36* (2006.01)
(Continued)

(52) U.S. Cl.
CPC ......... *A61N 1/0484* (2013.01); *A61N 1/0452* (2013.01); *A61N 1/0456* (2013.01);
(Continued)

(58) Field of Classification Search
CPC .. A61N 1/0484; A61N 1/0452; A61N 1/0456; A61N 1/36003; A61N 1/36031; A61B 5/024; A61B 5/318; A61B 5/4266
See application file for complete search history.

(56) References Cited

U.S. PATENT DOCUMENTS 7,660,636 B2  2/2010  Castel et al.
7,949,403 B2  5/2011  Palermo et al.
(Continued)

FOREIGN PATENT DOCUMENTS

WO   WO 2016/130867   8/2016
WO   WO 2017/088275   6/2017
(Continued)

OTHER PUBLICATIONS

International Search Report and Written Opinion for PCT/US2021/051149 dated Mar. 18, 2022.

*Primary Examiner* — Amanda K Hulbert
*Assistant Examiner* — Philip C Edwards
(74) *Attorney, Agent, or Firm* — Knobbe, Martens, Olson & Bear LLP

(57) ABSTRACT

An electrical stimulation training and neuromuscular rehabilitation system including a machine-washable stimulation suit with multiple electrodes to provide controlled stimulation of various muscle groups is provided. The stimulation suit may also include one or more integrated biosensors to provide diagnostic capability in addition to stimulation. The system may also include a software platform executable on a user computing device (such as a tablet) that may facilitate control of the stimulation programs (e.g., intensity level, duration, isolation of individual muscle groups vs. full body stimulation) of one or more stimulation suits by the wearer or a fitness practitioner or trainer and/or that may facilitate intervention by a medical provider through a remote telemedicine platform.

21 Claims, 63 Drawing Sheets

Related U.S. Application Data

(60) Provisional application No. 63/269,818, filed on Mar. 23, 2022, provisional application No. 63/204,226, filed on Sep. 21, 2020.

(51) Int. Cl.
 A61B 5/00 (2006.01)
 A61B 5/024 (2006.01)
 A61B 5/318 (2021.01)

(52) U.S. Cl.
 CPC ..... A61N 1/36003 (2013.01); A61N 1/36031 (2017.08); *A61B 5/024* (2013.01); *A61B 5/318* (2021.01); *A61B 5/4266* (2013.01)

(56) References Cited

U.S. PATENT DOCUMENTS

| | | | |
|---|---|---|---|
| 8,660,651 B2 | 2/2014 | Castel et al. | |
| 8,738,142 B2 | 5/2014 | Palermo et al. | |
| 9,390,630 B2 | 7/2016 | Daniels | |
| 9,802,039 B2 | 10/2017 | Palermo et al. | |
| 10,143,397 B2 | 12/2018 | Altshuler et al. | |
| 10,437,335 B2 | 10/2019 | Daniels | |
| 10,698,492 B2 | 6/2020 | Daniels | |
| 11,033,206 B2 | 6/2021 | Roh | |
| 11,229,787 B2 | 1/2022 | Daniels et al. | |
| 2012/0016440 A1* | 1/2012 | Muccio | A61N 1/0452 607/48 |
| 2012/0144551 A1* | 6/2012 | Guldalian | A61N 1/0484 2/102 |
| 2015/0202429 A1 | 7/2015 | Fritzsche | |
| 2017/0303849 A1* | 10/2017 | De Sapio | A61N 1/36031 |
| 2017/0347923 A1 | 12/2017 | Roh | |
| 2017/0358235 A1 | 12/2017 | Daniels | |
| 2018/0001086 A1* | 1/2018 | Bartholomew | B29C 35/02 |
| 2018/0036531 A1 | 2/2018 | Schwarz | |
| 2019/0001135 A1* | 1/2019 | Yoo | A61N 1/36132 |
| 2019/0083784 A1* | 3/2019 | Raghunathan | A61B 5/4082 |
| 2020/0237031 A1 | 7/2020 | Daniels et al. | |
| 2020/0353239 A1 | 11/2020 | Daniels et al. | |
| 2020/0393905 A1 | 12/2020 | Daniels | |
| 2021/0244941 A1 | 8/2021 | Daniels et al. | |
| 2021/0353181 A1 | 11/2021 | Roh | |
| 2022/0288382 A1 | 9/2022 | Daniels | |

FOREIGN PATENT DOCUMENTS

| | | |
|---|---|---|
| WO | WO 2017/088276 | 6/2017 |
| WO | WO 2017/163131 | 9/2017 |

* cited by examiner

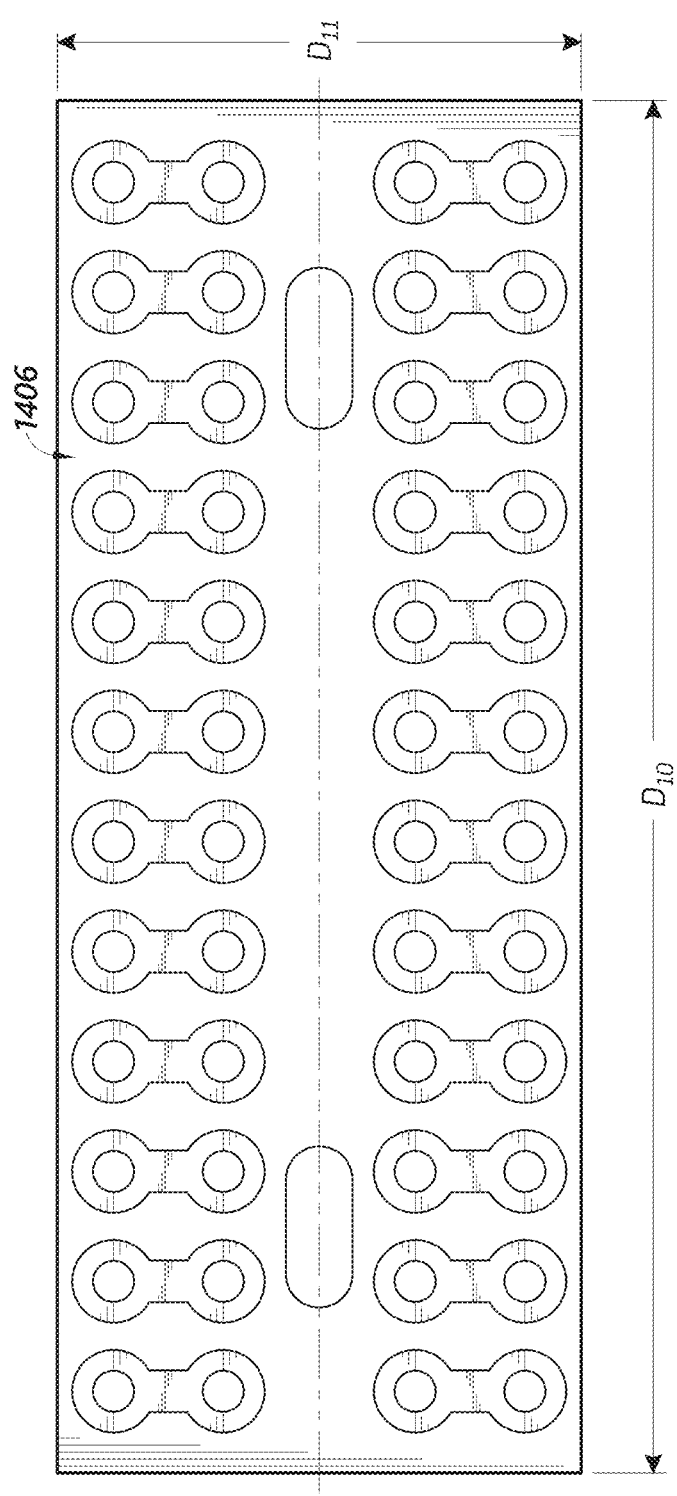 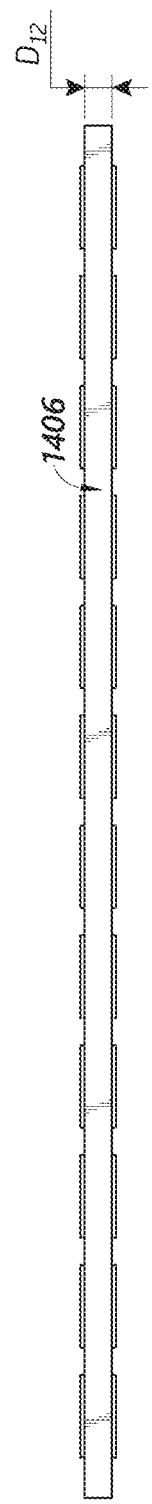
FIG. 14A
FIG. 14B

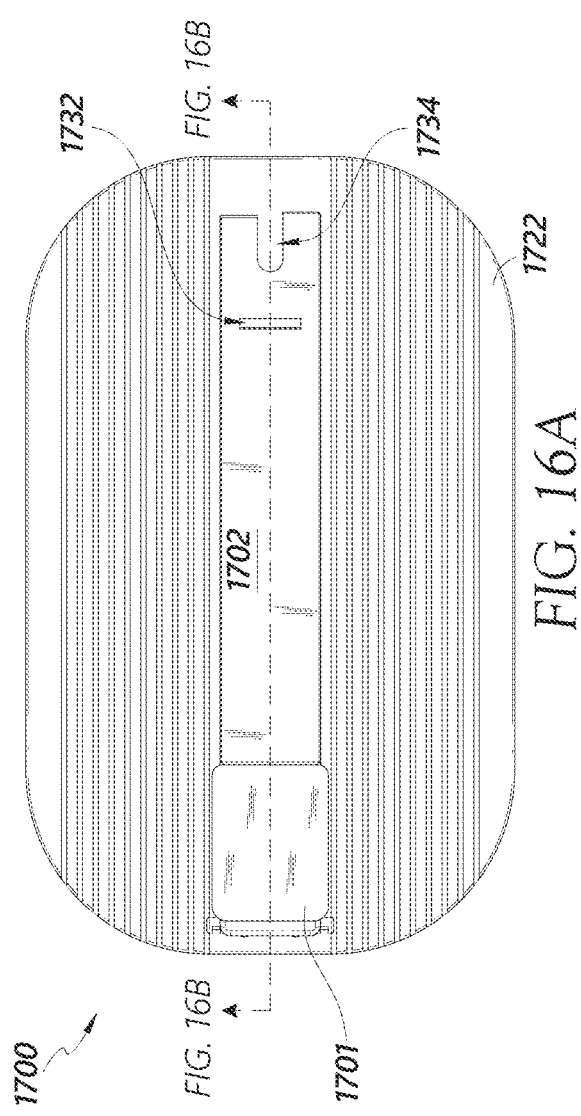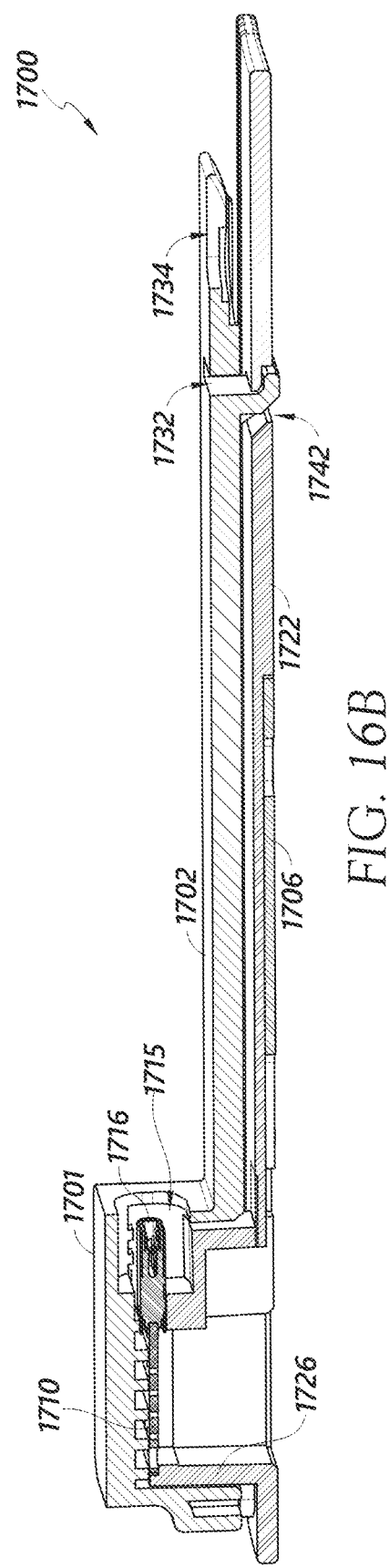

SYSTEMS AND METHODS FOR MANAGED TRAINING AND REHABILITATION VIA ELECTRICAL STIMULATION

INCORPORATION BY REFERENCE TO ANY PRIORITY APPLICATIONS

This application is a continuation-in-part application of International PCT Application No. PCT/US2021/051149 filed Sep. 20, 2021, which claims priority to U.S. Provisional Appl. No. 63/204,226 filed Sep. 21, 2020. This application also claims priority to U.S. Provisional Appl. No. 63/269,818 filed Mar. 23, 2022. The entire contents of each of the above-recited applications are hereby incorporated by reference under 37 CFR 1.57.

FIELD

Electrical muscle stimulation (EMS) uses electrical impulses to elicit muscle contraction via electrodes applied to the skin over target musculature. EMS is a tool useful for, among other things, strength training and exercise recovery in healthy individuals and athletes, rehabilitation and injury prevention, pain management, and testing and evaluation of the neuromuscular system.

BACKGROUND

Electrical muscle stimulation (EMS) machines (e.g., transcutaneous electrical nerve stimulation (TENS) machines) have been used to strengthen muscles or assist in pain relief. The electrical muscle stimulation machines may be used at home or in a clinical or office setting. Typically, the electrical muscle stimulation is provided to separate muscles using separate adhesive electrode units or machines. Wired stimulation vests or stimulation wraps have also been used.

SUMMARY

In accordance with several implementations, training and rehabilitation systems and methods described herein incorporate electrical stimulation devices (e.g., whole-body wearable suits with stimulation electrodes and sensors) that are constructed into a machine washable, monitored, and/or remotely-controlled platform. The systems may provide widespread diagnostic capability and may advantageously facilitate interventions in conjunction with the diagnostic capability, substantially in real time and/or after the fact.

In accordance with several implementations, a training and rehabilitation system (e.g., functional impulse training and rehabilitation system or a training and/or rehabilitation delivery and/or management system) is a platform for delivery and/or management of electro-muscular stimulation (EMS) via a wearable and washable textile, which gives medical providers the ability to conduct, for example, neuromuscular rehabilitation and pain management prevention remotely through a telemedicine platform. The training and rehabilitation system can include a wearable textile that cooperates with a remote telemedicine platform using EMS. In several implementations, the wearable stimulation delivery textile is washable, antibacterial and/or antimicrobial, with moisture-wicking electrodes woven into a comfortable suit. The telemedicine platform may advantageously allow the system to be used at home, or in a gym, athletic facility, clinic, or office (e.g., a professional setting). The training and rehabilitation system advantageously offers health and fitness practitioners (such as trainers, therapists, and clinicians) the flexibility to train or manage clients, or users, individually or within a group setting. For example, in a group setting, each trainee or patient may have their own individual stimulation parameters (e.g., power intensity, durations, or amplitude levels) set for individual muscle groups. The training and rehabilitation delivery and/or management system also allows practitioners to adjust electrical stimulation parameters in real time, for both individual trainees or patients and individual muscle groups, to dynamically adapt to each client's changing performance. Parameters and/or the stimulation itself may be adjusted or stopped for various individuals in a group setting in an efficient manner using a graphical user interface (e.g., via a touchscreen display on a user computing device (e.g., tablet, laptop, smartphone)).

In accordance with several implementations, the training and rehabilitation system includes diagnostic sensors in the suit used to perform analysis (for example, sweat and/or heart rate or other biomarker analysis) and provide feedback (e.g., to facilitate intervention in response to diagnostics). Capturing of biomarker, or physiological parameter, data pre, during, and/or post-exercise/therapy using a wearable textile is advantageously facilitated by the training and rehabilitation system. Software analysis of that data cross-referenced with other data points can be used (e.g., using artificial intelligence algorithms or techniques) to predict specific issues and report to a medical professional through an electronic medical record. This diagnostic capability is available before, during, and after client interventions are delivered from the wearable and software. This provides simple delivery and widespread diagnostic capability.

The training and rehabilitation system can be used in multiple different settings and/or by multiple different types of entities including but not limited to hospitals, rehabilitation facilities, private practice physical therapists or occupational therapists, physiatrists, orthopedic surgeons, chiropractors, recovery centers, corporate wellness programs, private consumers for at-home use or use in gyms or workout centers, athletic or fitness trainers for private or group training sessions conducted in person or virtually via the Internet, gym personnel, athletic facilities, sports teams, pilots in fighter planes, space travel, and space stations with military and/or other government agency personnel for both human performance optimization and physical rehabilitation, and with patients both inpatient and outpatient including over a telehealth platform.

In some implementations, an electrical stimulation (e.g., fitness training and rehabilitation system or delivery and/or management system) includes a machine-washable textile body suit. The suit can include conductive electrodes positioned along the textile body suit at various locations so as to facilitate neuromuscular stimulation of various regions of a body of a wearer and at least one integrated sensor adapted to collect biodata indicative of a physiological parameter of the wearer. The various locations may correspond to locations of various different muscles that are candidates for electrical stimulation (e.g., pectorals, right/left biceps, right/left triceps, abdominal muscles, upper back muscles, lower back muscles, glutes, right/left quadriceps, right/left hamstrings, and/or deltoids). A controller can be configured to provide adjustable stimulation signals to the conductive electrodes and to receive the biodata. A signal pathway can connect the plurality of conductive electrodes to the controller. The controller can be configured to wirelessly communicate with a user computing device to allow a user to adjust the stimulation signals via a user interface (e.g., touchscreen display) of the user computing device that, upon execution of program instruction stored on a non-transitory computer-readable storage medium, receives input data from the user and generates control signals to the controller responsive to the user input data.

In some implementations, the system can include at least 20 electrodes. However, other numbers of electrodes may be used. The electrodes can be dry electrodes. The electrodes can be configured to contact at least body locations corresponding to muscles of the arms, chest, back, legs, and/or shoulders when the body suit is worn. The electrodes can be adapted to absorb moisture and/or include an anti-microbial agent. The anti-microbial agent can be silver. In some implementations, the signal pathway can be conductive wire, conductive thread, conductive ink, wireless protocol, or combinations thereof.

In some implementations, the controller can be removably connected to the signal pathway with a connector port (e.g., via a mechanical connection interface). The connector port can include an outer circuit on an outside of the body suit for connecting to the controller, an inner circuit on an inside of the body suit connected to the signal pathway, and flexible wires connecting the outer circuit to the inner circuit. The outer circuit can include an outer printed circuit board and the inner circuit includes an inner printed circuit board. The outer circuit can include an electrical connector and the connector port can include an outer cover containing the outer circuit. The connector port can further include a removable seal over the electrical connector. The removable seal can include a watertight seal. The controller can be housed in a control box, and the outer cover can be shaped to mate with a back of the control box when the controller is connected.

In some implementations, the signal pathway can include a first connector port on a first side of the garment and a second connector port on a second side of the garment, and the controller can be removably connectable to both the first connector port and second connector port.

In some implementations, the integrated sensor can include a heart rate sensor. In one implementation, the heart rate sensor can be an EKG sensor. The integrated sensor can also include one or more sweat sensor. The controller can be configured to send the biodata (e.g., using wireless communication implementations) to the user computing device to facilitate monitoring of the physiological parameter or biomarker.

In some implementations, a neuromuscular stimulation training and rehabilitation system can include a machine-washable neuromuscular stimulation body suit. The body suit can include conductive electrodes positioned along the body suit at various locations to facilitate neuromuscular stimulation of various regions of a body of a wearer, an integrated sensor adapted to collect biodata indicative of a physiological parameter of the wearer, a controller configured to provide adjustable stimulation signals to the conductive electrodes and to receive the biodata, and a signal pathway connecting the plurality of conductive electrodes to the controller.

In some implementations, the integrated sensor can include a sweat sensor, a temperature sensor, a wetness sensor, a pH sensor, or a cardiac sensor. The integrated sensor can be connected to the controller via the signal pathway.

In some implementations, the system also includes a manager device (e.g., computing or processing and display device) configured to wirelessly communicate with the controller and to receive signals from the at least one integrated sensor. The manager device can be further configured to, upon execution of program instructions stored in memory on the manager device, allow a user to adjust an intensity, duration, or other parameter of the stimulation signals.

In some implementations, the sensor is a cardiac sensor. The controller and/or the manager device can be further configured to determine a heart rate from the cardiac sensor. In some implementations, the sensor is a sweat sensor, and the controller and/or the manager device is further configured to measure at least one of lactose, glucose, sodium, and potassium in sweat of a person wearing the body suit. Multiple sensors may also be used.

In some implementations, the stimulation signals are a pre-set pattern configured to cause a coordinated motion of a person wearing the body suit. The coordinated motion can include but is not limited to walking, jogging, running, cycling, throwing, swinging a baseball bat or golf club or other athletic equipment, strength training, body toning, sitting to standing, standing to sitting, reaching and returning, and combinations thereof.

In some implementations, a method can provide electrical stimulation to a wearer of a stimulation suit including a plurality of electrodes positioned to provide simultaneous electrical stimulation to a plurality of different muscle groups of the wearer. The method can comprise, at a user computing device (e.g., tablet, laptop, smartphone) wirelessly coupled to a controller of the stimulation suit, determining a training task and determining a pre-programmed electrical stimulation program based on the training task, wherein the electrical stimulation program comprises stimulation program parameters including an intensity level, a duration, and muscle groups to be targeted. The method can include transmitting instructions associated with the electrical stimulation program to the controller coupled to the stimulation suit so as to cause the controller to execute the electrical stimulation program by applying stimulation signals to the plurality of electrodes of the stimulation suit, receiving biodata from at least one integrated sensor of the stimulation suit, and storing the biodata in memory of the user computing device.

In some implementations, the method can include adjusting one or more of the stimulation program parameters via a graphical user interface of the user computing device. For example, the user computing device may comprise a touchscreen display configured to receive user input data in connection with touching of the display screen. The graphical user interface may facilitate global adjustments and/or adjustments to individual users (e.g., trainees, clients, or patients).

In some implementations, a method can facilitate control and monitoring of electrical stimulation provided to a plurality of individuals each wearing a stimulation suit comprising a plurality of electrodes positioned to provide simultaneous electrical stimulation to a plurality of different muscle groups of the individual. The method can comprise, at a user computing device wirelessly coupled to a controller of each of the stimulation suits, determining a pre-programmed electrical stimulation program associated with a training task identified by a user via a graphical user interface of the user computing device, wherein the electrical stimulation program comprises stimulation program parameters including an intensity level, a duration, and muscle groups to be targeted, transmitting instructions associated with the electrical stimulation program to the controller of each of the stimulation suits so as to cause the controllers to execute the electrical stimulation program by applying stimulation signals to the plurality of electrodes of the stimulation suits, adjusting one or more stimulation program parameters for at least one of the plurality of individuals by providing user input data via a graphical user interface of the user computing device, and transmitting adjusted instructions to the controller coupled to the stimulation suit the at least one of the plurality of individuals.

Additional features and advantages will be set forth in the detailed description that follows, and in part will be readily apparent to those skilled in the art from that description or recognized by practicing the apparatus and methods as described herein, including the detailed description that follows, the claims, and the appended drawings.

It is to be understood that both the foregoing general description and the following detailed description are merely exemplary, and are intended to provide an overview or framework for understanding the nature and character of the apparatus and methods as they are claimed. The drawings illustrate various embodiments and together with the description serve to explain the principles and operation.

BRIEF DESCRIPTION OF THE DRAWINGS

FIGS. 14A and 14B illustrate top and side views of an implementation of an inner printed circuit board of the control box connection of FIGS. 12A-B.

FIGS. 16A-16C illustrate another implementation of a control box connection between the stimulation suit and the control box.

FIG. 20 illustrates an implementation of platform software of the training and rehabilitation system after a user has successfully logged in.

DETAILED DESCRIPTION

Figure 1:
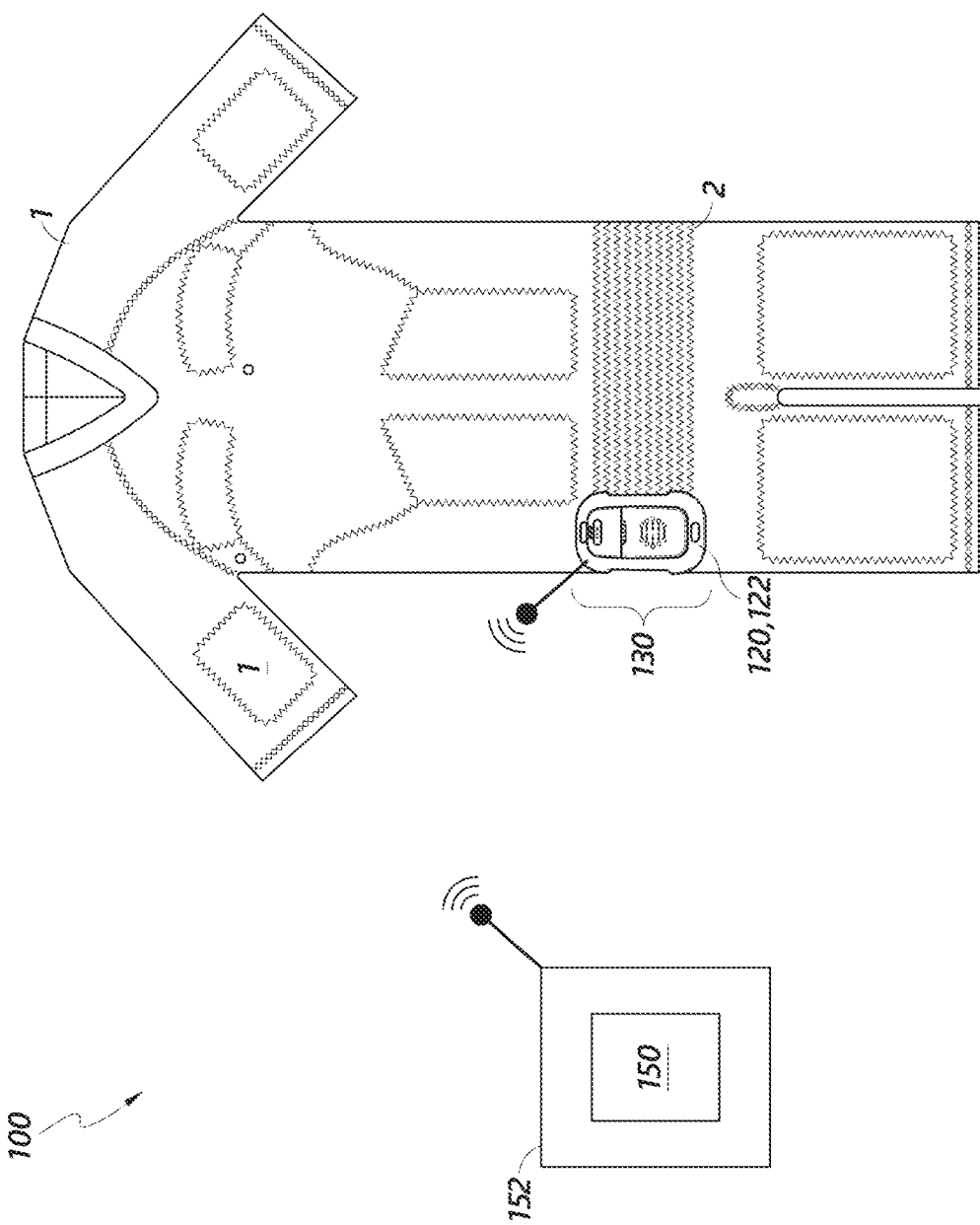
FIG. 1 illustrates an example of a training and rehabilitation system.

In accordance with several implementations of the training and rehabilitation system, a client and/or practitioner log in to a software platform while the client wears a textile stimulation delivery suit. A stimulation control box (e.g., CPU box) is attached to the textile stimulation delivery suit and activated. A detachable stimulator device (which may be incorporated into the stimulation control box) transmits, receives, and regulates electrical stimulation delivered to a plurality of electrodes or electrode pads in the suit through commands entered on the software platform (e.g., a graphical user interface on a tablet, laptop, smartphone, or other user computing device). In accordance with several implementations, sensors (e.g., biomarker sensors) coupled to the suit advantageously collect and analyze physiological or biodata parameters (for example sweat, heart rate, heart rate variability, blood oxygen levels, respiratory rate, electromyography), pre-, during-, and/or post-intervention. A snapshot may be created for a medical provider (e.g., as an electronic medical record with artificial intelligence (AI) analysis) of various precursors for medical conditions and areas of concern. This all advantageously occurs either in person or remotely through a rehabilitation therapeutic platform, in accordance with several implementations.

As illustrated in FIGS. 1-4, the training and rehabilitation system 100 includes a wearable garment, such as a textile suit 110, that carries multiple electrodes 1 and one or more biomarker or physiological parameter sensors 7A, 7B, 10 adapted to be held against the skin of a wearer or client. The suit 110 also carries a controller connection area 130, which includes a mechanical connection 8 and an electrical connection 9 for a stimulation controller 120. The controller connection area 130 is electrically connected to the electrodes 1 and the one or more sensors 7A, 7B, 10 via conductive pathways 2. A closure system 140 facilitates donning and doffing of the suit 110. The stimulation controller 120, housed in a control box 122, sends stimulation signals to the electrodes 1 and collects biodata from the sensors 7A, 7B, 10 via the conductive pathways. In the illustrated implementation, the stimulation controller 120 also wirelessly connects to a manager device 152 (e.g., computing device with a display screen) that runs software 150. The software 150, upon execution of program instructions stored on a computer-readable storage medium, displays collected data and system performance information (e.g., via a graphical user interface on a display screen). The software 150 also allows a practitioner or home-use client to control or manage (e.g., via a graphical user interface of a computing device, such as the manager device 152) the delivered stimulation according to pre-set patterns, and provides practitioners with flexibility to manage stimulation (e.g., adjust parameters of pre-set stimulation patterns, turn on or off stimulation) for an individual client (e.g., trainee or patient) and for multiple individual clients in a group setting. The centralized control facilitates efficient coordination of group training sessions of individuals each wearing a stimulation suit 110. The individual components of the system 100 are discussed in further detail below.

Smart Suit

The wearable textile suit 110, or "smart suit," comprises individualized wearable technology that delivers both a training and recovery program for the wearer, and collects physiological data, or biodata, from the wearer. Suit 110 reads the body (e.g., via sensors 7A, 7B, 10), generates wearer data (e.g., physiological parameter data, or biodata), and delivers the actual training and/or recovery stimulation. Suit 110 is designed to be tight-fitting yet comfortable throughout a training and/or recovery session. In many implementations, no moisture or cables are necessary to facilitate electrical or mechanical connections, so that freedom of movement is maximized. In some implementations, suit 110 is hygienic. For example, suit 110 is machine washable, and can be made antibacterial, for example through the incorporation of silver flaking. These various features of suit 110 are described in detail below.

The fabric of the textile suit 110 is comfortable to wear during movement or exercise, and holds the electrodes 1 and optional sensors (e.g., 7A, 7B, 10) in place against the wearer (e.g., against the skin of the wearer). In some implementations, the fabric is washable, antibacterial and/or antimicrobial, and moisture-wicking. In some implementations, suit 110 includes a washable textile made of 20% Rayon and 80% BlendX, a Polyamide/Spandex warp knitted jersey. However, other percentages, ratios or materials may also be used as desired and/or required.

Figure 2B:
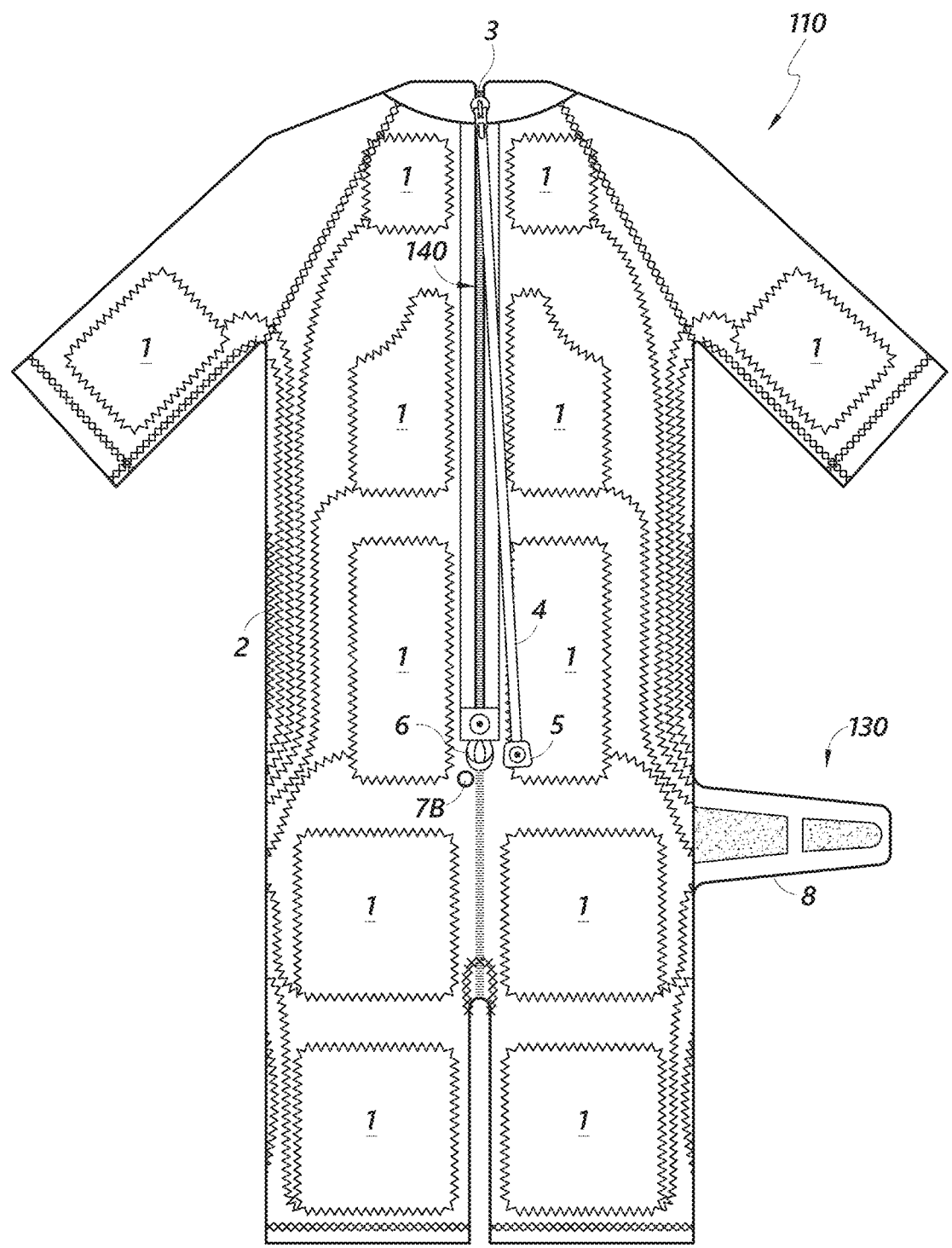
Figure 3B:
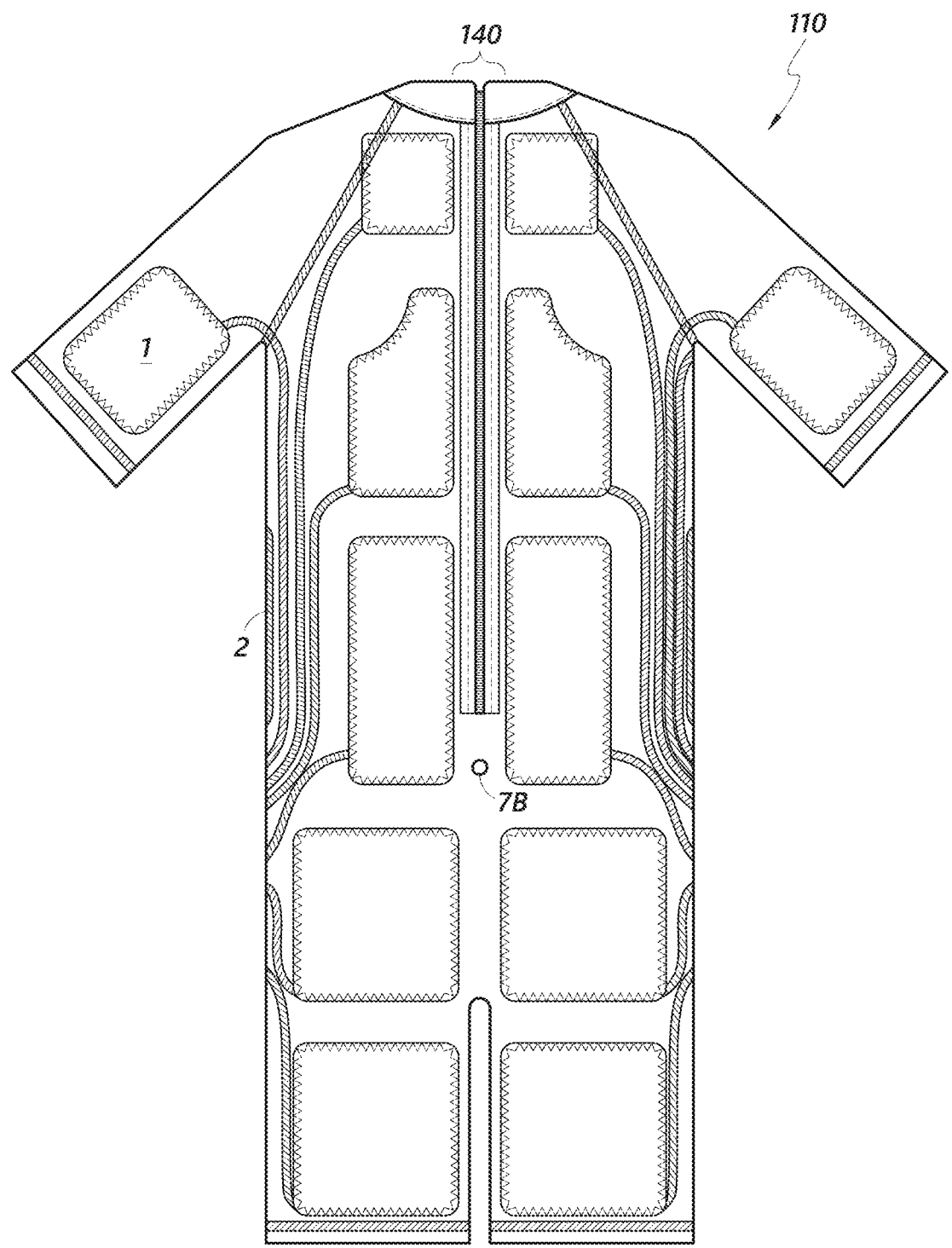
Figure 4A:
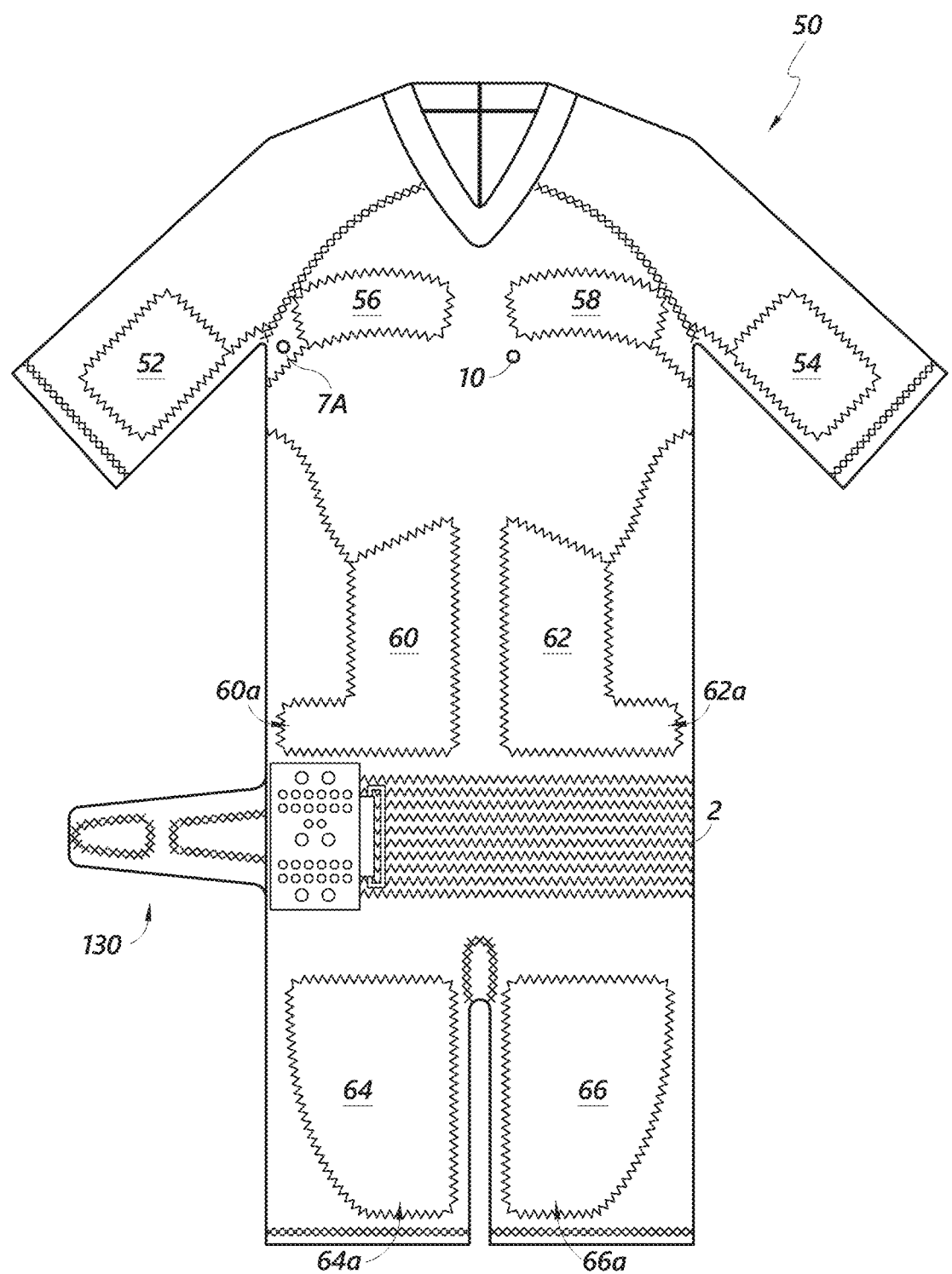
FIGS. 4A-4B illustrate an alternative implementation of the front and back of a wearable stimulation suit of the training and rehabilitation system.
Figure 4B:
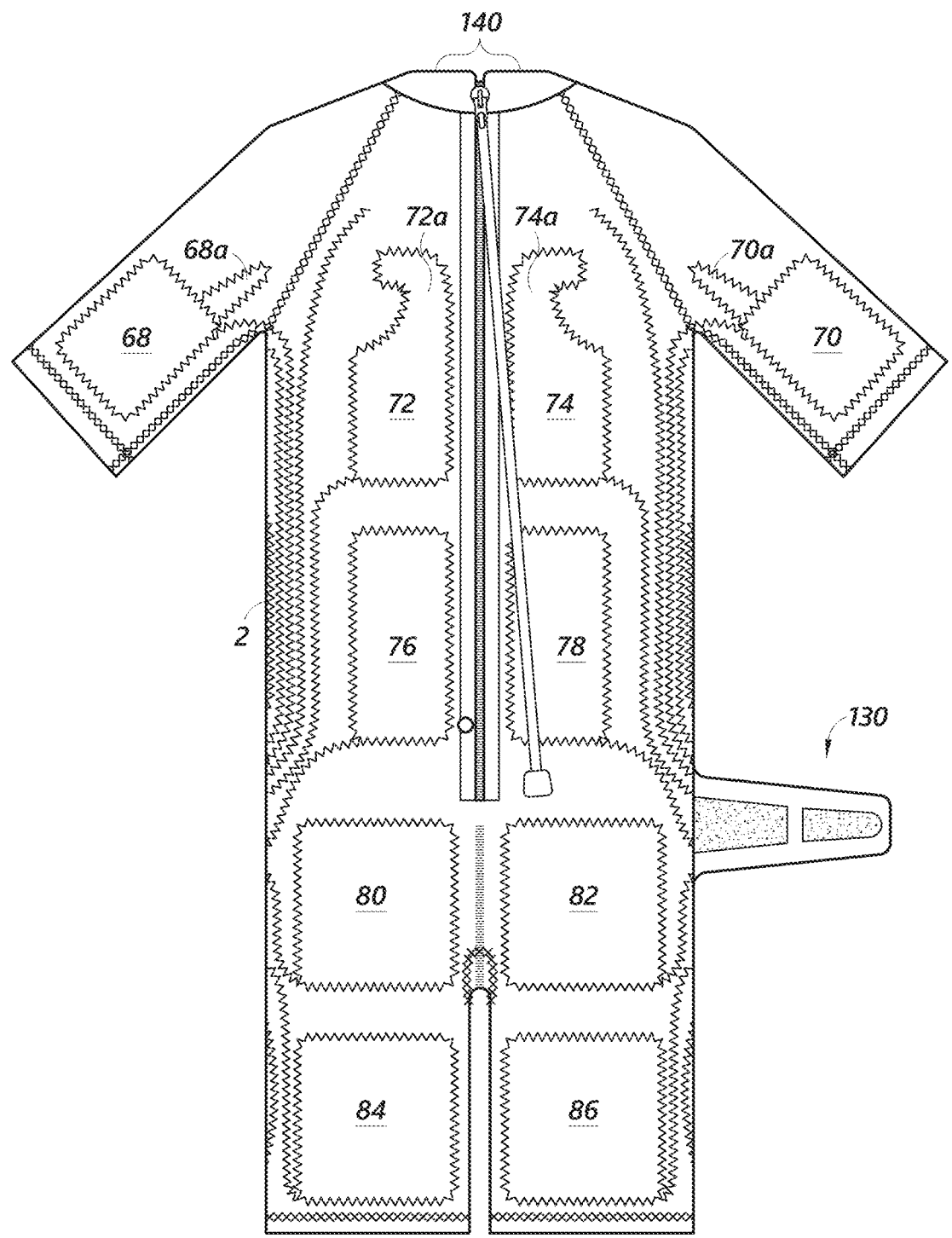

Suit 110 can include a closure system 140 that facilitates donning and doffing of the garment or textile. In some implementations, closure system 140 includes a zipper 3 with a pull cord 4 and a zipper pull loop 6. In some implementations, a magnet connection fastener 5 can hold the pull cord 4 in place after zipping. In some implementations, the closure system 140 can include hooks, snaps, hook-and-loop fasteners, or other suitable fasteners. In some implementations, such as illustrated in FIGS. 2B, 3B and 4B, the closure system 140 is located on the back of the suit 110, where the zipper 3 opens nearly all of the back of the suit 110. In some implementations, the closure system 140 can be shorter or longer, and can be located in other appropriate places on the suit 110. For example, the closure system 140 can extend along a side of the suit 110, over a shoulder, and/or down a leg. In some implementations, the suit 110 can include multiple closure systems 140, such as a zipper 3 down the back and additional closure system(s) at the neck, chest, and/or wrists.

FIGS. 1-4 illustrate the garment as a body suit 110, but the garment is not limited to this size or shape. For example, suits 110 may be full-body suits in some implementations, extending from neck to ankle or may extend from neck to knee, or may extend along other body lengths. In some implementations, the suit 110 may be an arm sleeve, shirt, vest, leg sleeve, sock, and/or shorts, for example.

Electrodes

As illustrated in FIGS. 1-4, the textile suit 110 carries electrodes 1 adapted to be held against, or placed in contact with, the skin of the wearer. Like the textile of suit 110, the electrodes 1 are washable, antibacterial and/or antimicrobial, and moisture-wicking textiles woven into or attached to the wearable suit 110. In some implementations, the electrodes 1 are high-density padded, absorbent, antimicrobial/antibacterial conductive electrodes. In some implementations, the electrodes 1 are moisture wicking. In some implementations, the electrodes 1 are Polyamide 18.9%, Polyester 36.5%, Spandex 12.3%, PE film, Sponge 25.2%, Pure silver 6.5%, and other material 0.6%. However, other percentages and materials may be used as desired and/or required (e.g., Polyamide 15-25%, Polyester 35-50%, Spandex 5-20%, Sponge 20-30%, pure silver 5-10%, and other material 0-5%).

The electrodes 1 are designed specifically to deliver electrical stimulation to the wearer from the suit 110. Therefore, the electrodes 1 are placed in or on the suit 110 in areas that contact the target musculature and/or nerves (e.g., skin overlying the muscles and/or nerves). In some implementations, the moisture-wicking feature of the electrodes 1 and/or suit fabric create an environment that conducts electrical pulses to the muscles and/or nerves. The pulses create a sensory neuromuscular contraction of the muscles and/or tissue (e.g., nerves) in contact with the particular electrode 1. This promotes circulation and strengthening of muscle fibers. At certain stimulation frequencies, the electrical pulses can be used for pain management, for example as a TENS unit.

In several implementations, electrodes 1 are embedded strategically within the suit 110 so as to be positioned over target musculature when the suit 110 is worn and comprise electrode pads that span an area of a particular muscle group or area of the body. In some implementations, the suit 110 includes twenty electrodes 1; however, other numbers of electrodes 1 may be used (e.g., 4, 5, 6, 7, 8, 9, 10, 11, 12, 13, 14, 15, 16, 17, 18, 19, 21, 22, 23, 24, 25, or more than 25 electrodes). In some implementations, the electrode locations correspond to one or more of the quadriceps, hamstrings, gluteals, abdominals, pectoralis, trapezius, posterior deltoid, latissimus dorsi, erector spinae, and triceps. Additional electrode locations corresponding to one or more other muscles, such as biceps, teres major, teres minor, rhomboids, infraspinatus, calf muscles (e.g., gastrocnemius, soleus), anterior tibialis, and/or anterior deltoid, can also be added. In some implementations, the suit 110 is optimized for a particular function, such as a rehabilitative function. For example, in a shoulder rehabilitation system, the suit 110 includes electrodes 1 located to stimulate the rotator cuff. In this sense, some implementations of the suit 110 include electrodes 1 to target neck, shoulder, elbow, wrist, hand, hip, knee, ankle, foot, and/or core (e.g., trunk, including shoulders, back, chest, and abdominals) musculature to improve flexibility, strength, and/or endurance.

The electrodes 1 are generally sized and shaped to correspond to the target muscles and/or nerves. In some implementations, such as that illustrated in FIGS. 2A-3B, the electrodes 1 are generally rectangular. In some implementations, the electrodes 1 can be rounded, for example a polygon with rounded corners, oval, elliptical, or circular. In still other implementations, the electrodes 1 are non-geometric shapes. In some implementations, the suit 110 includes electrodes 1 of different sizes and shapes. The electrodes 1 can each optionally include various extensions designed to target particular muscles or muscle bundles while avoiding other nearby muscles or muscle bundles. For example, in some implementations, the electrode shape is tailored to target the deltoid, without activating the nearby rhomboids. In accordance with several implementations, this process of matching an electrode shape to the particular target musculature to be stimulated can advantageously help control movements, assist proper exercise technique, avoid injury, increase joint stability, and/or optimize rehabilitation or other focused muscle work.

Figure 2A:
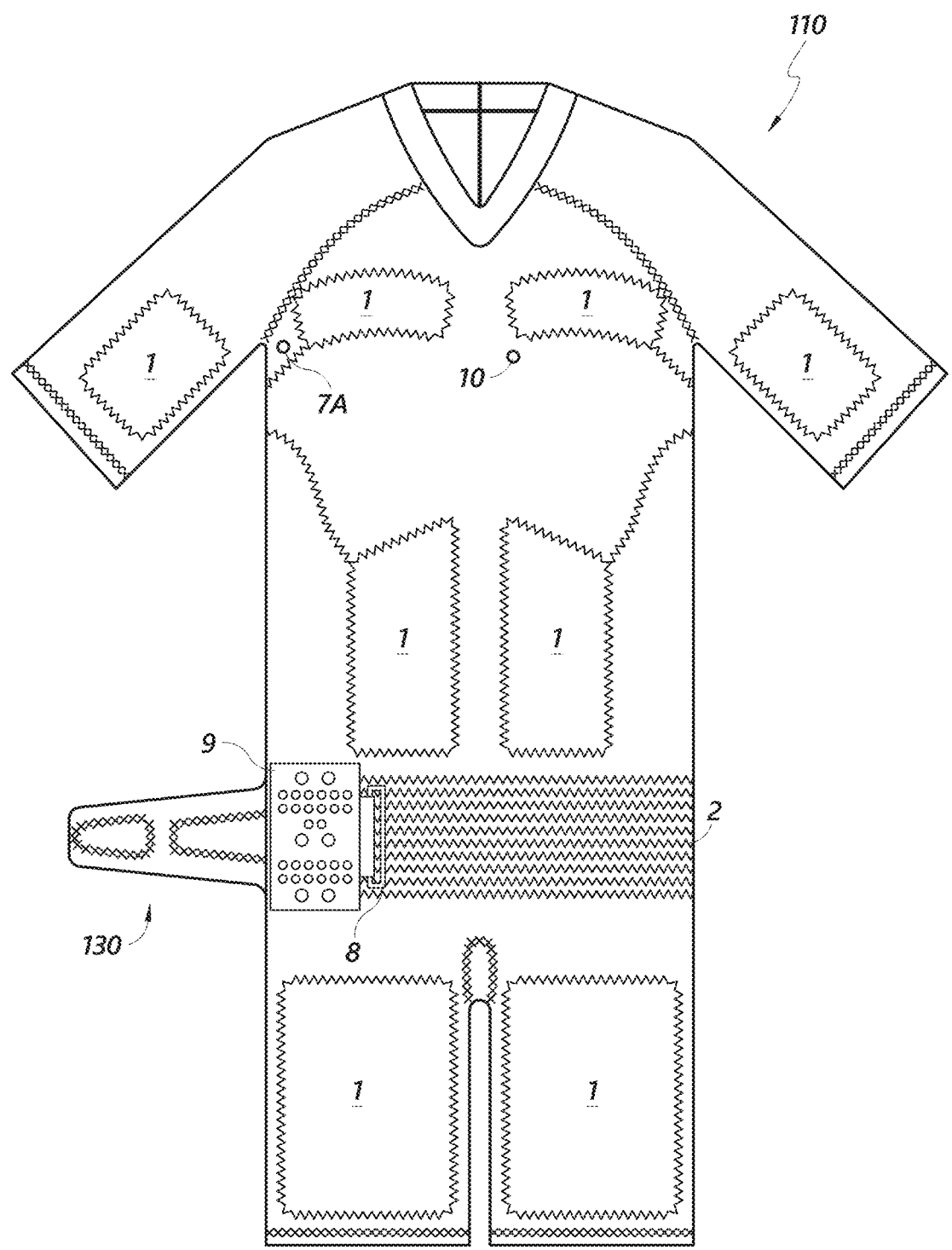
FIGS. 2A-2B illustrate the outside front and back of one implementation of a wearable stimulation suit of the training and rehabilitation system.
Figure 3A:
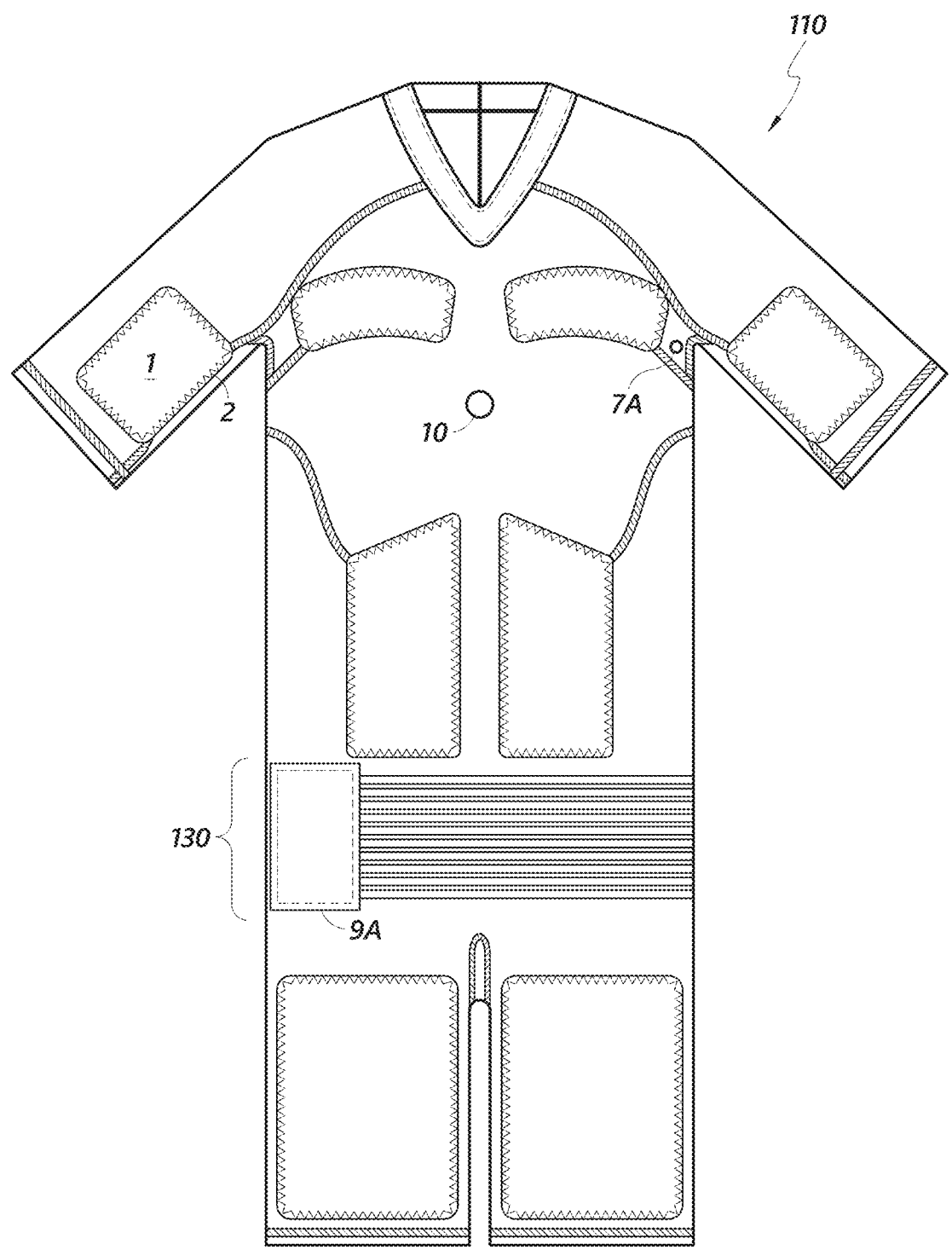
FIGS. 3A-3B illustrate the inside front and back of the wearable suit of FIGS. 2A-2B.
Figure 4C:
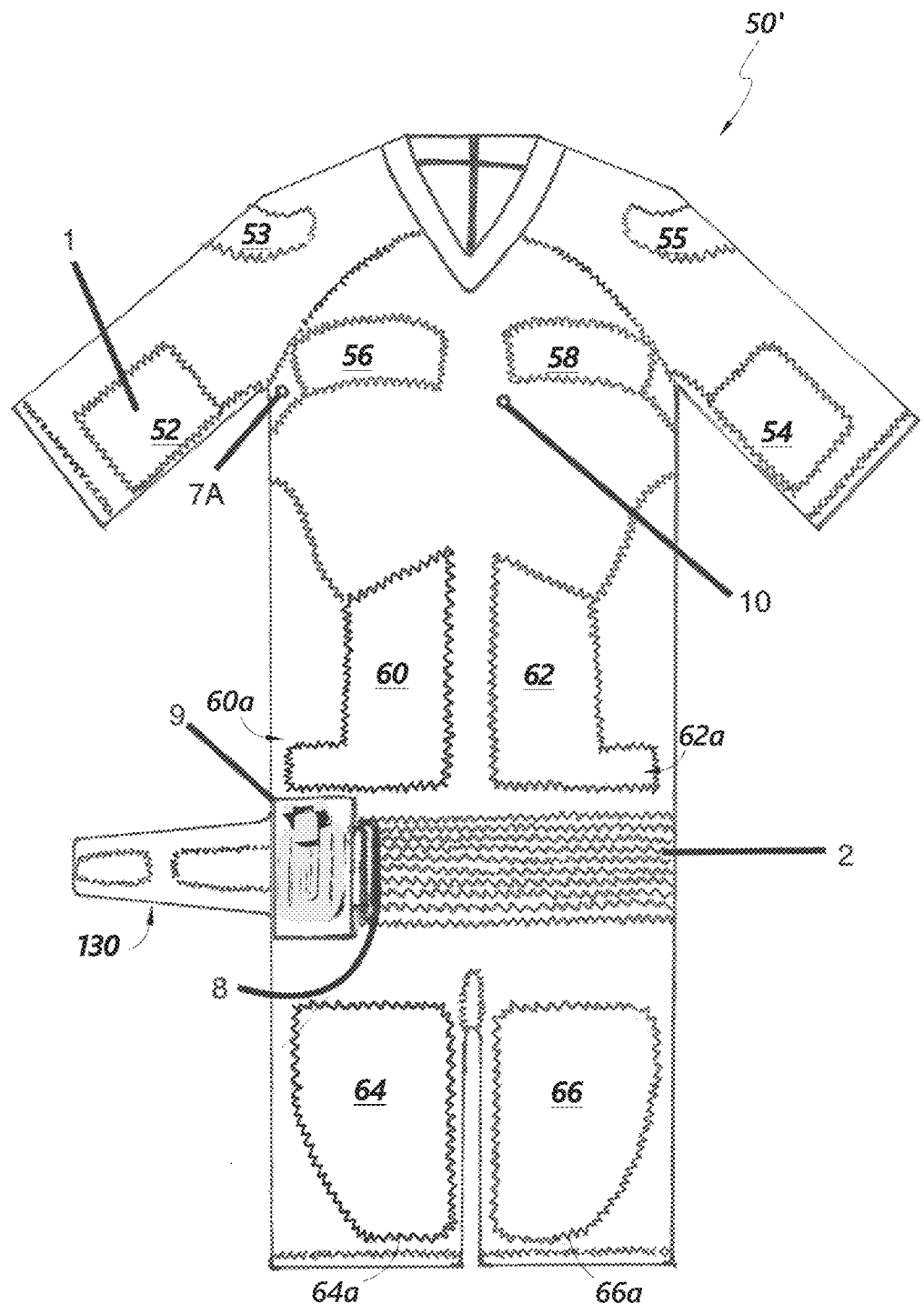
FIGS. 4C-4D illustrate an alternative implementation of the front and back of a wearable stimulation suit of the training and rehabilitation system.
Figure 4D:
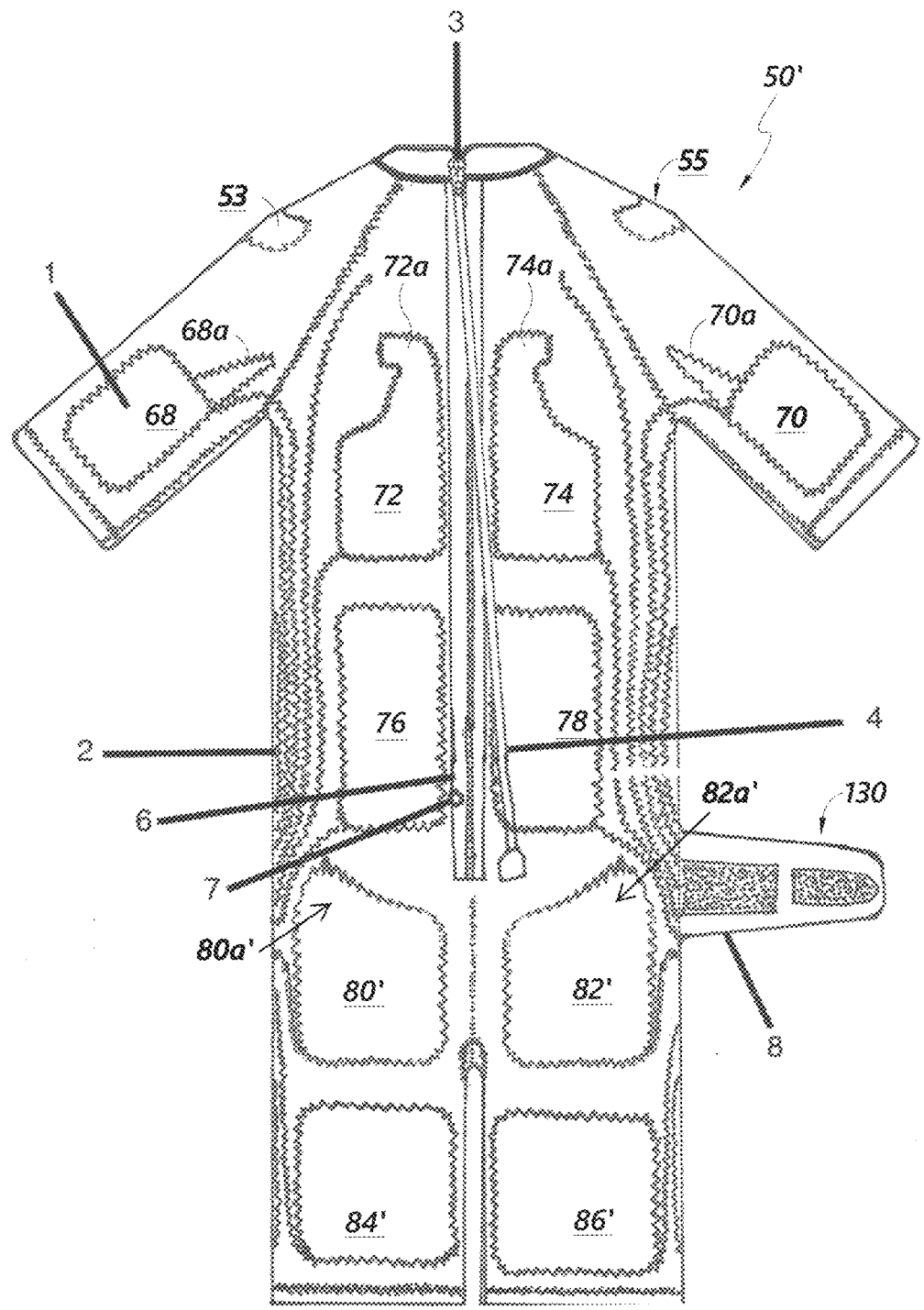

As illustrated in the example implementation shown in FIGS. 2A and 3A, the front of suit 110 can include multiple electrodes 1. In other implementations of the suit 110, for example the front of suit 50 shown in FIG. 4A, and the front of suit 50' shown in FIG. 4C, multiple electrodes 1 have specialized shapes to target musculature, as discussed below. As shown in FIGS. 4A and 4C, the front of suits 50 and 50' can include electrodes 52 and 54 that are generally rectangular and placed to target the triceps. Suits 50 and 50' can also include electrodes 56 and 58 that target the pectoralis muscles. These electrodes 56, 58 can be generally rectangular (as shown on suit 110 in FIGS. 2A and 3A), or slightly arched (as shown in FIGS. 4A and 4C). Additional electrodes can also be included to target other upper extremity and/or chest musculature. For example, electrodes 53 and 55 shown on suit 50' in FIGS. 4C and 4D can be included to target deltoids, rotator cuff, and/or upper heads of biceps and triceps. As illustrated in FIG. 4D, these electrodes 53 and 55 can extend over the shoulder to the back, and can target the upper trapezius, lower sternocleidomastoid, and/or additional sections of the deltoid.

Suit 50 can further include electrodes 60 and 62 that target the abdominal muscles. These electrodes 60, 62 can also be generally rectangular (as shown on suit 110 in FIGS. 2A and 3A), and can optionally include respective extensions 60a and 62a as illustrated in FIG. 4A and on suit 50' shown in FIG. 4C to more specifically target lateral abdominal muscles while avoiding the external obliques and serratus anterior. Suit 50 can also include electrodes 64 and 66 that target quadriceps muscles. These electrodes 64, 66 can be generally rectangular (as shown on suit 110 in FIGS. 2A and 3A) and can optionally include respective rounded lower corners 64a and 66a, as shown in FIGS. 4A and 4C, to more specifically target the full rectus femoris while adding the vastus medialis and avoiding the vastus lateralis. These shapes can be useful, for example, for activities or movements that require knee stability and/or that tend to cause unwanted leg abduction.

As further illustrated in the example implementation shown in FIGS. 2B and 3B, the back of suit 110 can include multiple electrodes 1. Similarly, multiple electrodes 1 can be included in the back of example suit 50, as shown in FIG. 4B, and example suit 50' as shown in FIG. 4D. For example, suit 110, suit 50, and suit 50' can include electrodes 68 and 70 to target the triceps. The electrodes 68, 70 can be rectangular (as shown on suit 110 in FIGS. 2B and 3B) and can include optional respective extensions 68a and 70a shown in FIGS. 4B and 4D to more fully engage the triceps proximal heads while avoiding the distal head of the deltoid. Suit 50 can include electrodes 72, 74, 76, and 78 to target back muscles including the trapezius and latissimus dorsi muscles. These electrodes 72-78 can be generally rectangular (as shown on suit 110 in FIGS. 2B and 3B) and can optionally include respective extensions, such as extensions 72a and 74a shown in FIGS. 4B and 4D, to further target a middle portion of the trapezius without activating the upper trapezius or the nearby teres major, teres minor, or infraspinatus muscles. Back electrodes 76 and 78 can remain generally rectangular, or may include various similar extensions or cutouts to particularly target the lower back. In some implementations, the back electrodes 76' and 78' can be longer, shorter, thinner, and/or wider to target a larger or smaller portion of the back muscles. Electrodes 80 and 82 on suit 50, or corresponding electrodes 80' and 82' on suit 50' or electrodes 1 on suit 110, target the gluteal muscles, while electrodes 84 and 86 (and similar electrodes 84' and 82' on suit 50' and corresponding electrodes 1 on suit 110) target the hamstrings. As with the other electrodes, the electrodes 80, 82, 84, and 86 can be generally rectangular as shown in FIGS. 2B, 3B, and 4B, or may include various extensions or cutouts such as 80a' and 82a' shown in FIG. 4D. These electrodes can also be longer, shorter, thinner, and/or wider to target a larger or smaller portion of the leg extensors and/or hip stabilizers. For example, hamstring electrodes 84' and 86' shown in FIG. 4D can be shorter and wider to target more of the hamstrings while allowing gluteal electrodes 80' and 82' to be longer for more coordinated activation of the hip muscles. Cooperating muscles can be targeted by cooperating electrodes, which can overlap in some implementations. As noted above, the electrodes have sizes, shapes, and cutouts that can particularly target the hip muscles and/or avoid unwanted movement, for example hip stability and hip abduction as discussed above.

These shapes and locations are illustrative only, and are not intended to limit the shape, size, or location of the electrodes 1. As discussed above, the electrode shape and location can be altered to target or avoid particular musculature and/or nerves, which can be used to induce or avoid particular movements, enhance stability, reduce pain, and/or mimic aberrant conditions such as weakness, fatigue, injury, and/or instability. The electrode shapes and locations can be altered between different suits of different sizes so as to cover target muscle areas or body areas for bodies of different shapes and sizes. The suits 110 may be full-body suits in some implementations, extending from neck to ankle or may extend from neck to knee, or may extend along other body lengths.

In some implementations, the electrodes 1 are removable from the suit 110. In other implementations, the electrodes 1 are integrated with the suit 110 and not removable. In still other implementations, a suit 110 can include both removable and integrated electrodes. Integrated electrodes are machine-washable along with the suit 110, and do not need replacement after use. Removable electrodes can be washable or disposable. In some implementations, removable electrodes are separately washable, while in other implementations the removable electrodes can remain attached to the suit for laundering. In some implementations, removable electrodes can be secured to the suit 110 by connecting fasteners. In some implementations, removable electrodes are attached with a mechanical connection and an electrical connection. In some implementations, the mechanical and electrical connections are provided by the same fastener. In some implementations, the fasteners are mating fasteners, for example, mating snaps, clips, hook-and-loop fasteners, pins, barrels, screws, lugs, and the like.

In many configurations, the electrodes 1 are designed to be washable, comfortable, moisture controlling, shear and friction reducing, and/or antimicrobial textiles. The electrodes 1 are electrically conductive to deliver the stimulation to the patient. In some implementations, the electrodes 1 include a layer of electrically conductive material. In some implementations, electrically conductive material is provided in or on other layers, such as the various layers discussed below. In some implementations, the electrodes 1 include absorbent material that draws in fluid, such as sweat, and allows the electrode 1 to become conductive or more conductive. In other implementations, the electrodes 1 can optionally include a gel, hydrogel, saline, or other electrolyte to enhance conductivity to the skin. In still other implementations, the electrodes 1 are dry electrodes. Dry electrodes can be advantageous because they require little to no preparation to use effectively, and dry electrodes can be applied against hairy areas such as the back, chest, and legs.

Figure 10:
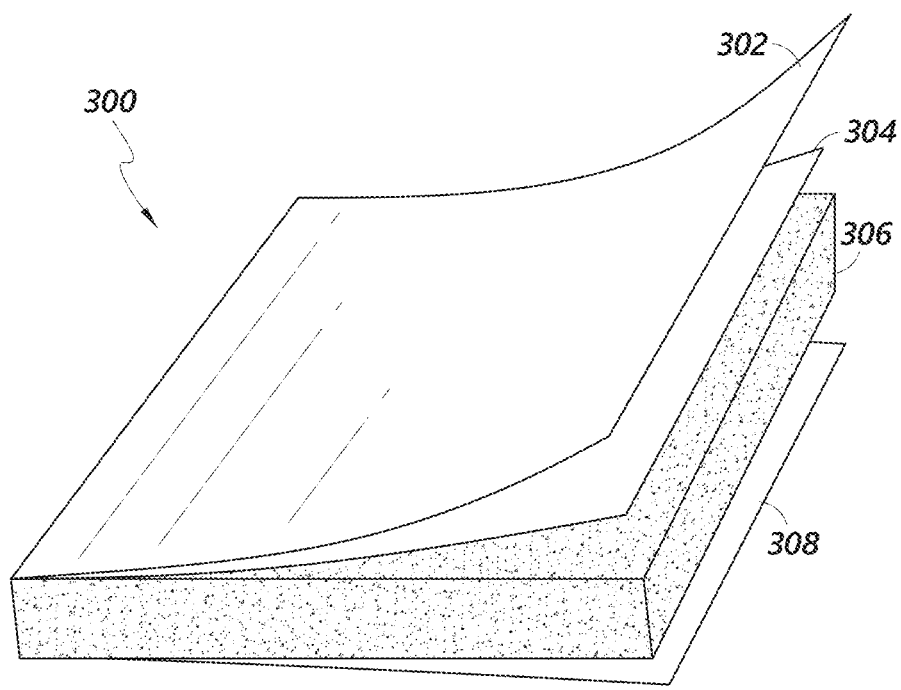
FIG. 10 illustrates a cross-section view of an implementation of an electrode of the stimulation suit of FIGS. 1-4.

FIG. 10 illustrates one suitable type of dry electrode 300, which could be implemented in any of the electrodes 1. A conductive layer 302 allows the stimulation signal to reach the wearer. In some implementations, this layer is a conductive textile or other flexible conductive material, such as conductive silicone. In some implementations, the layer is a conductive textile made from nylon and/or silk fibers embedded and/or woven with silver-plated polyurethane. The conductive layer 302 is connected to the signal pathway, as discussed below.

In some implementations, the thickness of the electrodes 1 creates a padded surface for the wearer. The layering, size, and thickness of the electrodes 1 can create a cushion for the wearer, thereby reducing unwanted surface pressure and increasing comfort. In some implementations, the padding of the electrode 1 is provided by a padding layer, such as padding 306. In some implementations, the elastic layer is a sponge having an appropriate thickness. In some implementations, the elastic layer is 0.5 mm to 50 mm thick (e.g., 1.0 mm to 20 mm thick, 2.0 mm to 8 mm thick, 0.5 mm to 5 mm thick, 5 mm thick to 10 mm thick, 8 mm thick to 20 mm thick, 10 mm thick to 40 mm thick, 25 mm thick to 50 mm thick overlapping ranges thereof, or any value within the recited ranges), as desired and/or required. In some implementations, the padding layer is an air layer, cellular fabric, or the like.

In some implementations, the padding layer performs additional functions, such as moisture absorption or shear reduction as discussed below. In some implementations, the entire electrode surface is padded. In other implementations, only portions, such as a center portion or outer portion, are padded. In some implementations, the padding thickness is uniform, while in other implementations the thickness is non-uniform, such as tapered or textured padding. Non-limiting examples of suitable padding layer materials include sponge, polyethylene (PE) and PE film, polyamide, polyester, silk, nylon, polyurethane, pure silver, and rubber.

In some implementations, breathable, absorbent, and/or wicking electrodes can be used to control skin moisture and the electrode microclimate to help maintain skin integrity and minimize discomfort. In some implementations, the electrode 300 is capable of absorbing moisture. In some implementations, the electrodes 1, 300 include a wicking material, such as a wicking material in thin film layer 304. In some implementations, the electrodes 1, 300 are designed to absorb moisture, such as sweat, while remaining operable to deliver electrical stimulation signals to the patient. In some implementations, the electrodes 1, 300 are padded with absorbent or superabsorbent material, for example as padding layer 306. As mentioned above, some electrode implementations include wicking, absorbent, and/or super-absorbent materials that draw in fluid to allow the electrode 1, 300 to become conductive or more conductive. Non-limiting examples of wicking material include porous PE or PE film, cotton, hemp, rayon, microfibers, and/or the like. Non-limiting examples of absorbent and superabsorbent materials include sponge, PE, linen, cotton, terry, bamboo, and/or the like.

In many implementations, the electrodes 1, 300 are made of material or laminates (e.g., in conductive layer 302 or in a body-contacting electrode cover) that reduce friction on the point of contact surface of the body. Such materials include, but are not limited to, nylon, silk, polyester, and combinations thereof. These materials, along with others like cotton, bamboo, and hemp, can be woven in satin, sateen, and/or the like to produce textiles that reduce friction on the skin to lessen the likelihood of discomfort. In some implementations of electrode 300, a nylon-silk surface 302 and rubber base backing 308 cooperate to decrease friction and shear. In other implementations, the skin-contacting surface has high friction, for example a tacky, adhesive, and/or non-slip surface. These electrodes 1, 300 can reduce the likelihood of sliding or migrating away from the target muscles during donning and/or use of the system. In still other implementations, the electrodes 1, 300 include hybrid surfaces with high-friction and low-friction sections.

In some implementations, the electrodes 1, 300 and/or suit fabric include antimicrobial additives or agents. These antimicrobial additives can be provided as a separate layer, or they can be embedded in any of the other layers of electrodes 1, 300 or suit 110. For example, in some implementations, the electrodes 1, 300 can be embedded with threads, flaking, and/or microparticles of silver, copper, and/or the like. The antimicrobial agents discussed here are non-limiting examples of materials selected to help prevent bacterial/microbial build up in the textiles, thereby affecting the microclimate of the wearer to help reduce odor, chafing, rashes, and/or other discomfort.

These various layers, materials, and functions can be combined to create a generally flexible and comfortable dry electrode 300 of the system 100. Dry electrode 300 can be used as any of the electrodes, including electrodes 1 and 52-86. In one particular implementation, discussed here with reference to FIG. 10, the electrode 300 can include a conductive layer 302 made of woven nylon and/or silk embedded and/or woven with silver-plated polyurethane fibers for conductivity. This fabric is electrically conductive, anti-microbial, and shear-reducing. Thin film layer 304 is a film of polyethylene that helps the layers adhere together and provides a barrier to promote wicking of moisture (e.g., sweat) as discussed above. In this particular implementation, the thin film layer 304 cooperates with the padding layer 306 to draw and trap moisture. In this example, padding layer 306 is an elastic sponge material that provides cushioning and moisture absorption. Base layer 308 in this implementation is a non-conductive, non-slip rubber backing base cloth. The base layer 308 reduces the friction, and resulting electrical noise, caused by movement between the electrode 300 and/or the suit 110 and the skin of the wearer.

Figure 11:
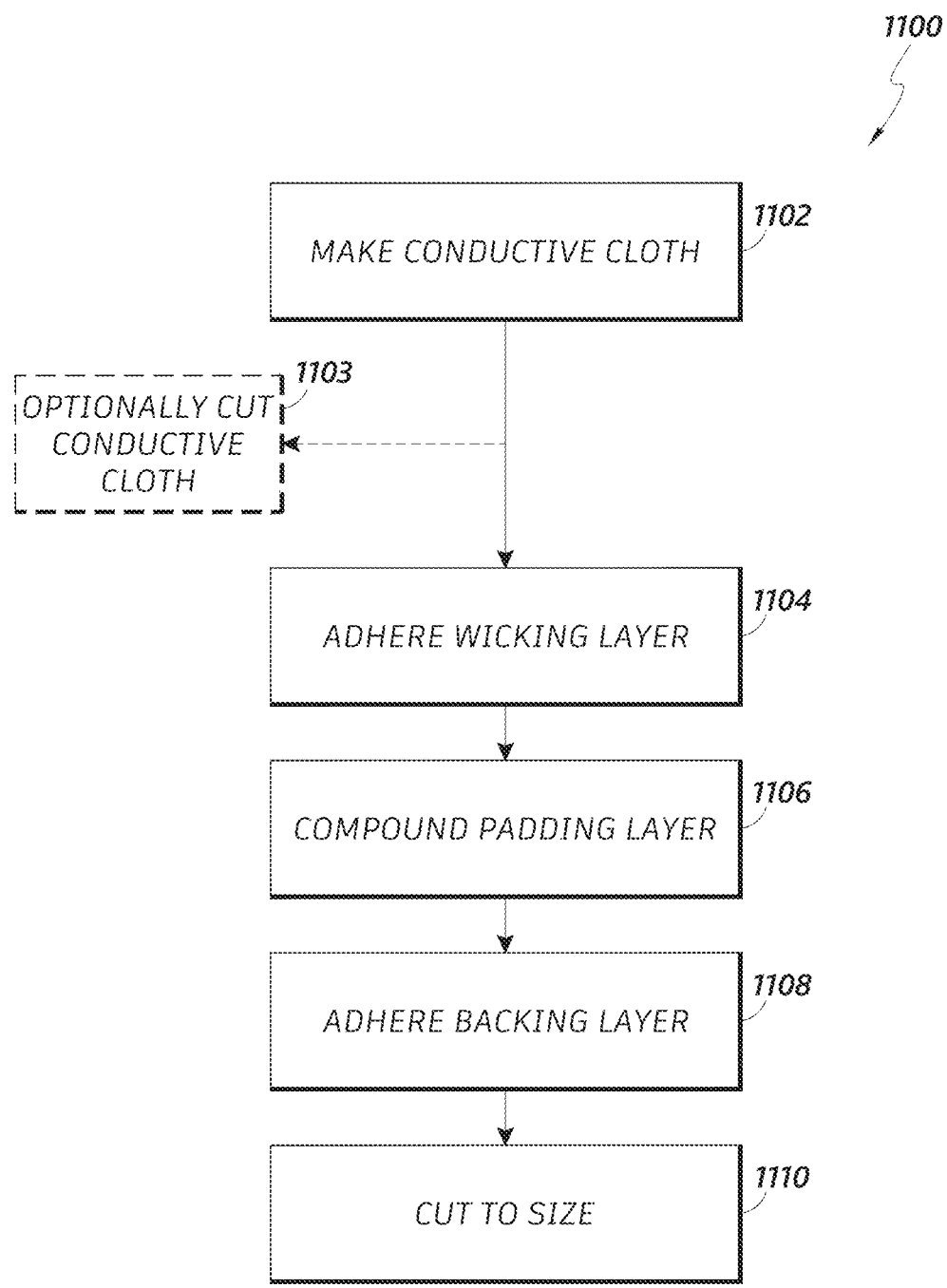
FIG. 11 illustrates an implementation of a method of manufacturing an electrode of the stimulation suit.

One example method of making close-fitting dry electrodes is illustrated in FIG. 11. Method 1100 schematically shows the steps of making an electrode 300. The backing layer 308 is used for connection and fixed on an inner side of the suit 110 (see FIGS. 3A-3B), and the conductive layer 302 is fitted to the muscles/skin of the wearer. In step 1102, the conductive cloth is made. For example, in one implementation, the conductive layer is a conductive textile with silver plating for electrical conductivity. Elastic fabric (warp-knitted fabric, weft-knitted fabric or woven fabric) is woven from nylon/silk fiber and polyurethane. In some implementations, the nylon/silk fiber is a fine fiber. Chemical silver plating is performed on the elastic fabric to obtain a silver-plated cloth for conductive layer 302. In some implementations, the silver-plated cloth filaments can be twisted to ensure better elasticity. This implementation advantageously releases silver ions, which have a strong bactericidal effect. In other implementations, the silver-plated cloth of conductive layer 302 can be manufactured by any suitable method, such as a process in which silver is first plated on the surface of nylon/silk fiber that is then woven to form conductive elastic fabric. Another layer of silver may be plated onto the elastic.

In step 1104, a thin film layer 304 is adhered onto the silver-plated cloth of the conductive layer 302 by dot-coating. In many implementations, the thin film layer 304 is a wicking film layer that can improve the absorption of sweat and allow moisture to quickly spread on the surface so that the electrical impedance is reduced quickly. In some implementations, the thin film layer 304 can also improve conductivity of the conductive layer 302 by pressing the silver particles of the conductive cloth together. This advantageously also reduces the loss of silver during washing and maintains good physical contact between the silver coils of the conductive textile 302, thereby improving washing durability.

In step 1106, a padding layer 306 is compounded onto the thin film layer 304 by flame to obtain compounded electrode cloth. In some implementations, the padding layer 306 is an elastic/sponge layer that improves the fit of the electrodes 300 to the skin of the patient. In step 1108, the backing layer 308 is adhered. In some implementations, the backing layer 308 is a non-conductive rubberized base cloth that is compounded to the sponge of the padding layer 306. In some implementations, the base layer 308 is an elastic fabric layer or a laminate of elastic fabric and non-conductive rubberized cloth. Backing layer 308 can be compounded on the padding layer, such as a foam elastic padding layer 306, by dot-coating or by flame.

In step 1110, the laminate electrode cloth obtained in steps 1102-1108 is cut according to the desired shape and size to serve as the electrode 300. In some implementations, the conductive fabric 302 is cut in step 1103, before being adhered to the thin film layer in step 1104. In this case, the laminate stack may be cut or trimmed again in step 1110, or the electrode 300 may be considered finished after step 1108. The obtained close-fitting dry electrodes 300 have the characteristics of low resistivity, washing durability, uniform electrical conductivity, comfortable fitting effect and quick sweat absorption. Optionally, according to different requirements, a piece of mesh cloth may be adhered or compounded between the thin film 304 and the base layer 308. The mesh cloth can be included in addition to or instead of padding layer 306 in step 1106. The electrodes 1 may also be manufactured using this method 1100.

Sensors

A variety of sensors (e.g., biosensors) can be included in the training and rehabilitation system 100 for several purposes. For example, in some implementations, sensors can be used to monitor biomarkers or physiological parameters of the wearers of the suit 110. In some implementations, the sensors are used to provide feedback. In some implementations, the feedback (e.g., alerts or indicators of deviations from expected parameters that are outside of a threshold range) is provided to the wearer, a practitioner (e.g., clinician, medical professional, trainer), and/or a remote location, such as a remote clinician, a medical record, and/or a monitoring station. In some implementations, the sensors are used to adjust the stimulation provided (either automatically or in response to an adjustment command initiated by the wearer or other person, e.g., health or medical practitioner or professional). In accordance with several implementations, the sensors advantageously provide diagnostic capability to an in-person or remote clinician or monitoring system. In accordance with several implementations, the training and rehabilitation system 100 facilitates diagnostic monitoring and/or intervention without requiring a person to go to a health facility or see a doctor in person. In other words, intervention may be provided via a telemedicine approach. In some implementations, remote monitoring and stimulation can be provided via remote program, such as a virtual reality, augmented reality, simulation, and/or metaverse environment.

Figure 5:
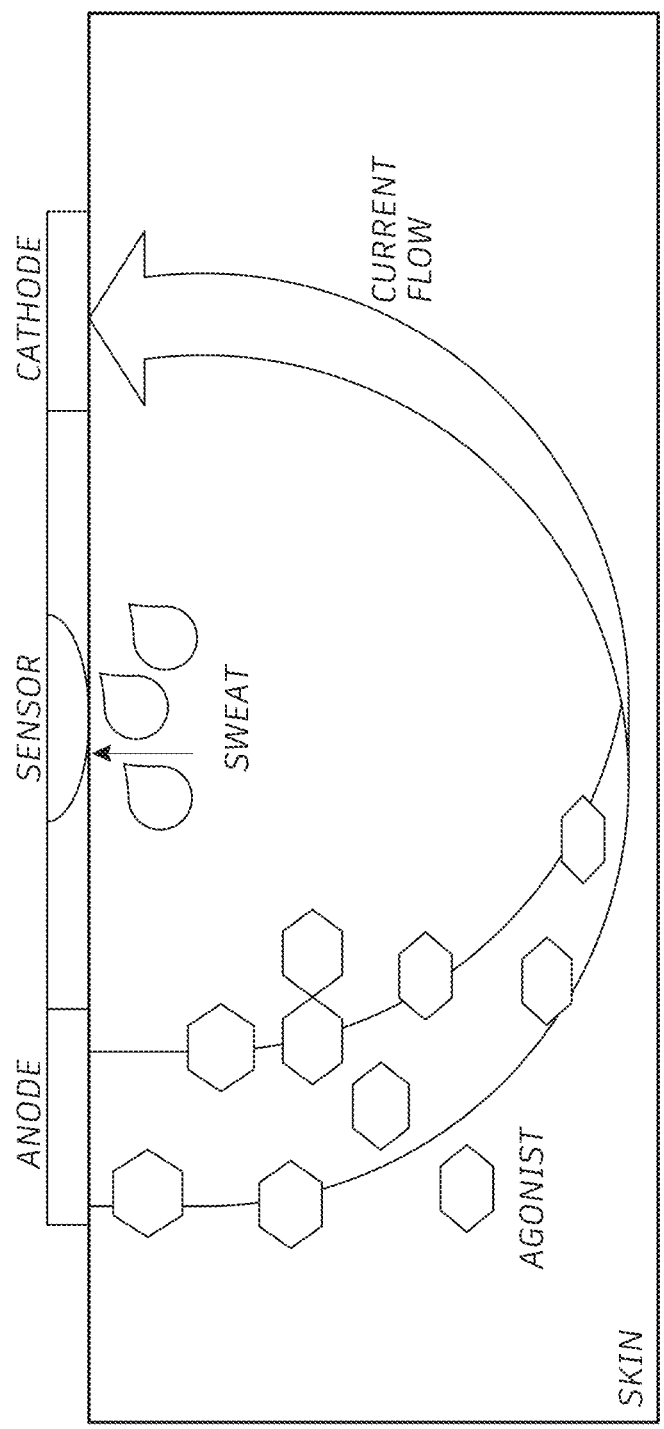
FIG. 5 is a schematic diagram illustrating operation of an implementation of a sweat sensor.

In some implementations, the suit 110 includes sweat sensors, for example sweat sensors 7A and 7B (generally, sweat sensors 7). The sweat sensors 7 can be located anywhere in the suit 110, such as at the axilla (e.g., sensor 7A) and/or the small of the back (e.g., sensor 7B). In some implementations, the sweat sensor 7 is a wetness sensor. In other implementations, the sweat sensors 7 operates as schematically illustrated in FIG. 5. This type of sensor is a sweat analysis bio-sensor that can measure components of sweat, including but not limited to analyte and electrolyte detection, such as lactose/lactate, urea, glucose, sodium, chloride and/or potassium, as well as pH and/or sweat rate. In accordance with several implementations, the suit 110 with sweat sensor(s) advantageously provides measurement of sweat rate and chemical analysis that is then analyzed by the operating software 150 to diagnose or identify potential medical conditions captured during a whole-body involuntary physical stress session (e.g., using a wearable garment that creates involuntary muscle contractions). The analysis and identification may be performed by the operating software 150 in real time or following the session.

FIG. 5 is a schematic representation of the sweat sensor operation. In this example implementation, sweat is collected through a moisture wicking electrode. The chemical passes through the anode, then to the cathode, and the data is processed by the transducer with a readable signal. The bioreceptor can be selected to target or identify an analyte of interest. The selected bioreceptor can output the analyte concentration as a physical or chemical signal with an identifiable defined sensitivity. Similarly, the transducer can be selected depending on the bioreceptor and required measurement technique. In some implementations, the sweat analysis sensor targets various types of chemical analysis with indicators cross-referenced with blood chemical analysis. In some implementations, the sweat sensor is a flexible sensor. In some implementations, the sweat sensor is a non-flexible sensor. In some implementations, the sweat sensor performs some analysis before transmitting representative data, for example a measure of the target analyte. In some implementations the sweat sensor transmits raw or unprocessed data. The sweat sensor may transmit data to the operating software 150 wirelessly (e.g., via BLUETOOTH™ or other wireless standard or transmission methodology) or via communication wires.

In some implementations, the suit 110 includes a cardiac sensor, for example heart rate sensor 10. The cardiac sensor 10 can be located anywhere in the suit 110, such as at the chest as shown in FIG. 2A, and/or in the back, collar, arm, or leg portions. In some implementations, the cardiac sensor 10 is a pulse sensor that detects pulsatile changes in blood flow to generate a heart rate measure. In some implementations, the cardiac sensor 10 is an electrical sensor that detects heart rate characteristics of an ECG or EKG signal, for example the QRS complex. In some implementations, multiple cardiac sensors cooperate to collect a heart rate and/or an ECG or EKG signal, for example a 3-lead, 5-lead, or 12-lead ECG and/or approximations and variations thereof. In some implementations, the cardiac sensor 10 is an electrode or group of electrodes. The electrode(s) may be similar to the dry electrodes described above, such as electrode 300, or the electrode(s) may be other known conductive electrodes suitable for collecting the appropriate signals from the skin. In some implementations, the cardiac sensor 10 is an optical sensor, for example a reflectance-type optical sensor. Other types of cardiac sensors are also suitable.

Sensors used with various implementations of the system 100 are described above, but the sensors can also include other sensors as well. For example, the sensors can include, but are not limited to, wet or dry electrodes, skin conductivity sensors, impedance sensors (for example skin impedance sensors), pressure sensors, accelerometers, gyroscopes, and/or other position sensors, strain gauges, thermal sensors, pH sensors, hygrometers, chemical sensors, gas sensors, piezo sensors, photodetectors, magnetometers, static charge-sensitive beds, glucose sensors (e.g., to measure glucose levels without fasting or stress testing), electromyography (EMG) sensors (for example to assess health of muscles and/or nerve cells), heart rate sensors, breathing sensors (for example, respiratory inductance plethysmography or RIP sensors), pulse oximetry sensors, acoustic sensors, microphones, audio monitors, video monitors or cameras, actigraphs, and/or the like.

In some implementations, some or all of the sensors are carried by the suit 110 as described above. In some implementations, some or all of the sensors are not carried by the suit 110 and are connected to the system 100. In some implementations, these sensors are connected via wired or wireless signal pathways to the control box 122 and/or manager device 152. For example, an ear or finger clip pulse sensor can be attached directly to the wearer and connected to the control box 122 and/or manager device 152 via wireless connection, or a video camera can be positioned in the room and connected to the manager device 152 with a wire.

In some implementations, the sensor parameter is continuously measured. In other implementations, the parameter is periodically sampled. In some implementations, sensor data is collected while stimulation is provided. In other implementations, sensor data is collected throughout a session, including pre- and post-stimulation. In some implementations, the sensors are removable from the suit 110. In other implementations, the sensors are integrated with the suit 110. In still other implementations, a suit 110 can include both removable and integrated sensors. Integrated sensors are machine-washable along with the suit 110, and do not need replacement after use. Removable sensors can be washable or disposable.

Signal Pathway and Connections

The controller connection area 130 is electrically connected to the electrodes, such as electrodes 1, 300 and/or electrodes 52-86. The controller connection area 130 is also optionally connected to sensors in the suit 110, such as sensors 7A, 7B and 10. In some implementations, the connection is made via conductive signal pathways 2. The signal pathways, such as conductive pathway 2, and the connection area 130 allow the stimulation controller 120 to communicate with the electrodes 1 and the control box 122 to communicate with any sensors (e.g., sensors 7, 10) when the control box 122 is connected at the connection area 130, and at least the electrical connection 9.

In some implementations, the pathway 2 allows two-way communication between the components, while in other implementations the communication is limited to one direction. In some implementations, the delivered signals comprise data and/or power. For example, in an implementation including sensors 7, 10, as discussed above, the signal pathway 2 can deliver stimulation signals from the control box 122 (e.g., stimulation controller 120) to the stimulation electrodes 1, power from the control box 122 to a sensor (e.g., sensors 7, 10), and sensor signals from the sensor 7, 10 to the control box 122.

In several implementations, the electrical current is transmitted through a physical signal pathway in the suit 110, such as signal pathway 2. In some implementations, the signal pathway 2 is a washable electrically conductive cabling, threading, ink, or other conductive pathway. In some implementations, the pathway 2 is sewn or placed on or within the suit 110. Preferably, the pathway 2 is machine washable with the suit 110. In other implementations, the pathway 2 is removable from the suit, to allow the suit 110 and/or electrodes 1 to be laundered. In some implementations, the signal pathway 2 is stretchable (e.g., elastic and/or serpentine).

In some implementations, the signal pathway 2 is made of conductive threading dipped in a conductive material, including but not limited to silver and/or copper, and spun.

For some implementations, preparing an elastic signal pathway is similar to preparing the conductive cloth of some of the electrodes 1, 300 as discussed above. For example, an elastic and washable signal pathway can be formed by plating chemical silver on nylon/silk fiber to form a conductive silver-plated nylon silk fiber. A plurality of these conductive silver-plated nylon/silk fiber filaments can be twisted and merged with polyurethane. In some implementations, a long wiring has a consistent length resistivity of 18 to 20 Ω/m. For many implementations, the maximum size of the signal pathway 2 is 1.10 m or less. Therefore, all leads of the signal pathway 2 can be controlled below 30Ω. This feature allows the wiring to have low energy consumption and increase the battery life of a portable device. This construction also withstands multiple washings, and maintains performance because the loss of silver is low.

In some implementations, the signal pathway 2 includes a connection line for each component (for example, each electrode 1 and sensor 7, 10). In other implementations, the signal pathway 2 alternatively or additionally includes a bus or rail, to which each component is connected. In some implementations, some or all components are permanently connected to the signal pathway 2. For example, the suits 110 and 50 illustrated in FIGS. 1-4 may include embedded electrodes 1 and/or sensors, such as sensors 7, 10 as described above, and the stimulation electrodes 1 and sensors 7, 10 may be permanently connected to the signal pathway 2. In other implementations, some or all of the components are attached with releasable connections. For example, the stimulation electrodes 1 and/or sensors 7, 10 can be releasably connected to the pathway 2 via snap, clip, magnet, and/or other connectors. In some implementations, the electrode 1 and/or sensor 7, 10 can be permanently or releasably connected via an adapter to make a suitable electrical connection.

Figure 6:
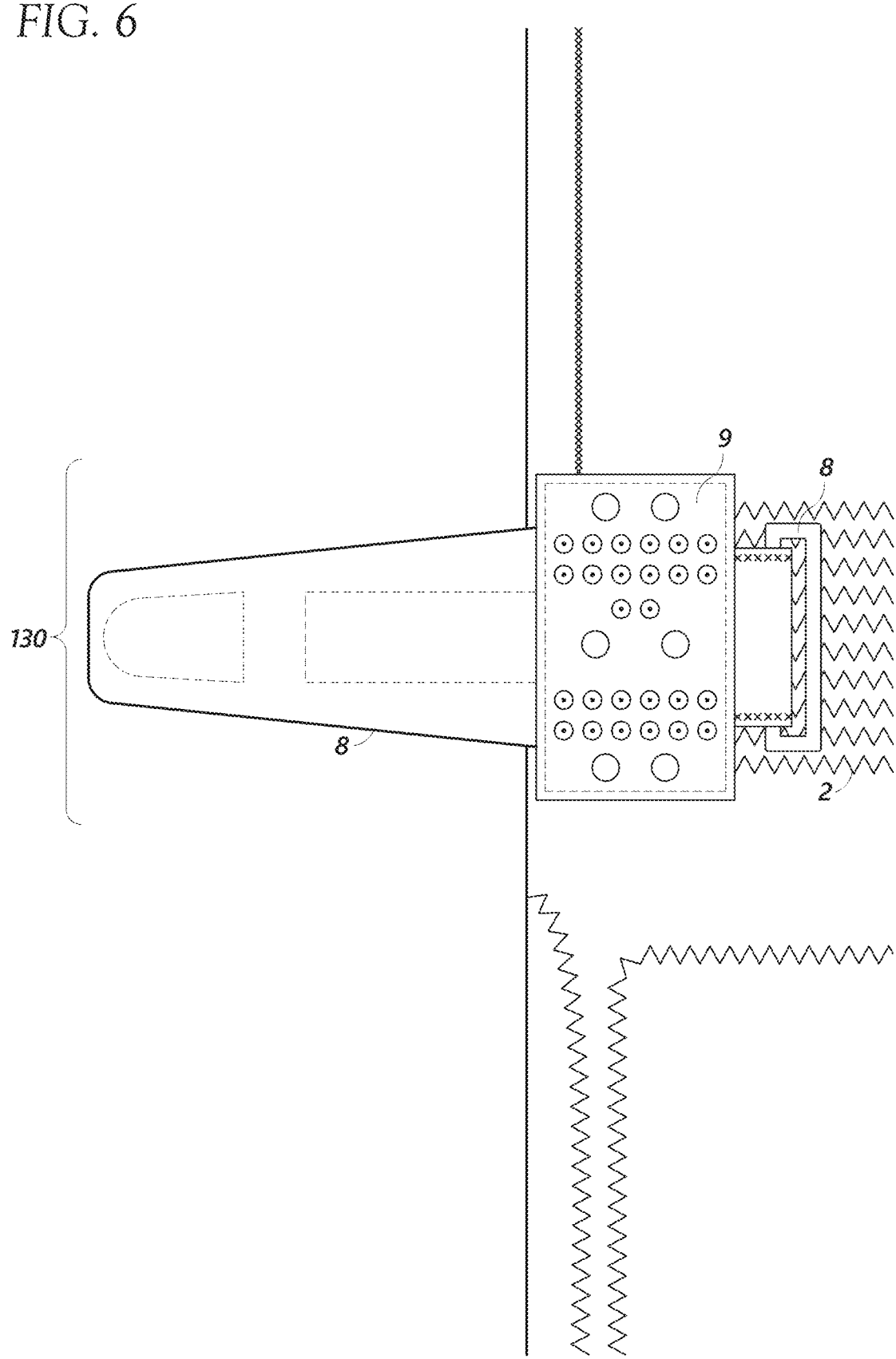
FIG. 6 illustrates an implementations of a connection between the wearable stimulation suit and a control box of the training and rehabilitation system.
Figure 9:
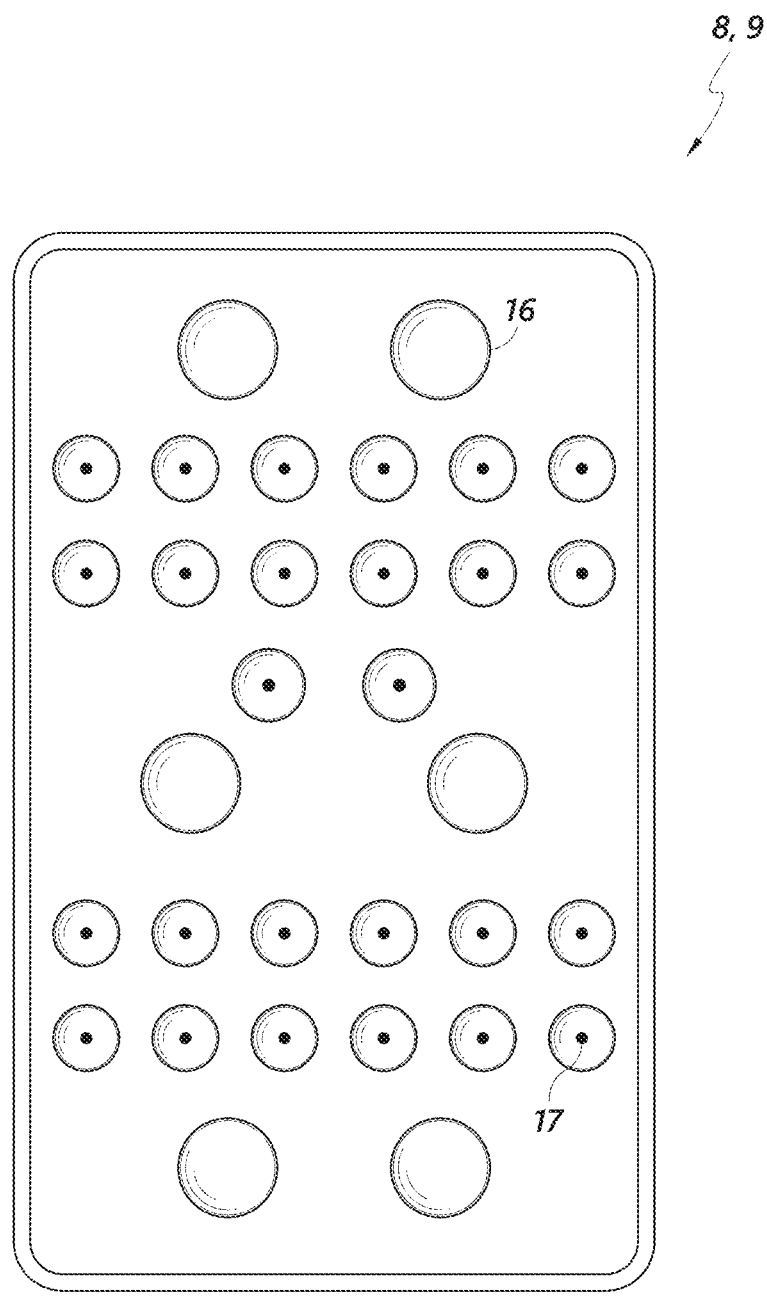
FIG. 9 illustrates an implementation of a mechanical and electrical connection between the wearable stimulation suit and the control box.

The other end of the signal pathway 2 connects to the stimulation controller 120, or control box 122, at controller connection area 130. The controller connection area 130 includes both a mechanical connection 8 and an electrical connection 9 for at least the stimulation controller 120. In some implementations, such as the connection shown in FIGS. 6 and 9, the controller connection area 130 includes a magnet plate. In other implementations, the connection is a rail or clip as shown in FIGS. 12-18, which provides both mechanical connection 8 and electrical connection 9. In still other implementations, the controller connection area 130 is a plug or clip for an electrical connection 9, and a mechanical connection 8 is provided separately. In some implementations, the mechanical connection 8 is a strap or band of elastic, hook-and-loop, buckle, drawstring, clip, shelf, and the like, such as buckled hook-and-loop 8 shown in FIGS. 2A, 2B, 4A, 4B, and 6 and/or mating straps 1804a and 1804b with optional hook-and-loop closure 1805 shown in FIGS. 17A-C. In other implementations, the mechanical connection includes a pocket. In some implementations, the controller connection area 130 includes an adapter. In some implementations, multiple electrical connections 9 and/or mechanical connections 8 are provided in connection area 130. In some implementations, the skin-facing side of the connection area 130 includes a cover 9A (see FIG. 3A). In some implementations, the cover 9A is a soft material covering the rigid components of the connection area 130 discussed below.

In some implementations, such as the examples illustrated in FIGS. 12-18, the controller connection area 130 on the suit 110 provides both a mechanical and electrical connection. As shown in FIG. 12A, the connector 1200 includes an interior portion with an inner or bottom plate 1222 and an interior or lower printed circuit board (PCB) 1206. An exterior portion includes a reinforced outer or upper plate 1202, an external cover 1201, and an exterior PCB 1210.

Outer plate 1202 in this example is a reinforced acrylonitrile butadiene styrene ("ABS") plate. In some implementations, the outer plate 1202 is a shaped rail, for example a T-shaped rail. In other implementations, the outer plate 1202 is a smooth or textured skid plate. The outer plate 1202 can help align the electrical connectors, provide mechanical stability for the connection, and improve durability of the suit 110. The outer plate 1202 includes a cover 1201 that protects and secures the electrical connector 1216 and the associated outer PCB 1210. In some implementations, the cover 1201 is shaped to provide a mechanical connection 8 for the control box 122, thereby helping secure the control box 122 when the control box 122 is connected to the connection area 130. The outer plate 1202 also includes a clip 1232 that fits into a mating slot 1242 in the inner plate 1222 to secure the end of the outer plate 1202.

Inner plate 1222 can be made of similar acrylonitrile-butadiene-styrene (ABS) plastic or another plastic or polymeric material. In some implementations, the inner plate 1222 is made of the same material as outer plate 1202. In other implementations, the inner plate 1222 is made of a different material, for example a more flexible material. In some implementations, the inner plate 1222 includes an opening or recess for the inner PCB, such as PCB 1206. The space can include a support 1208 to hold the inner PCB 1206.

Figure 12A:
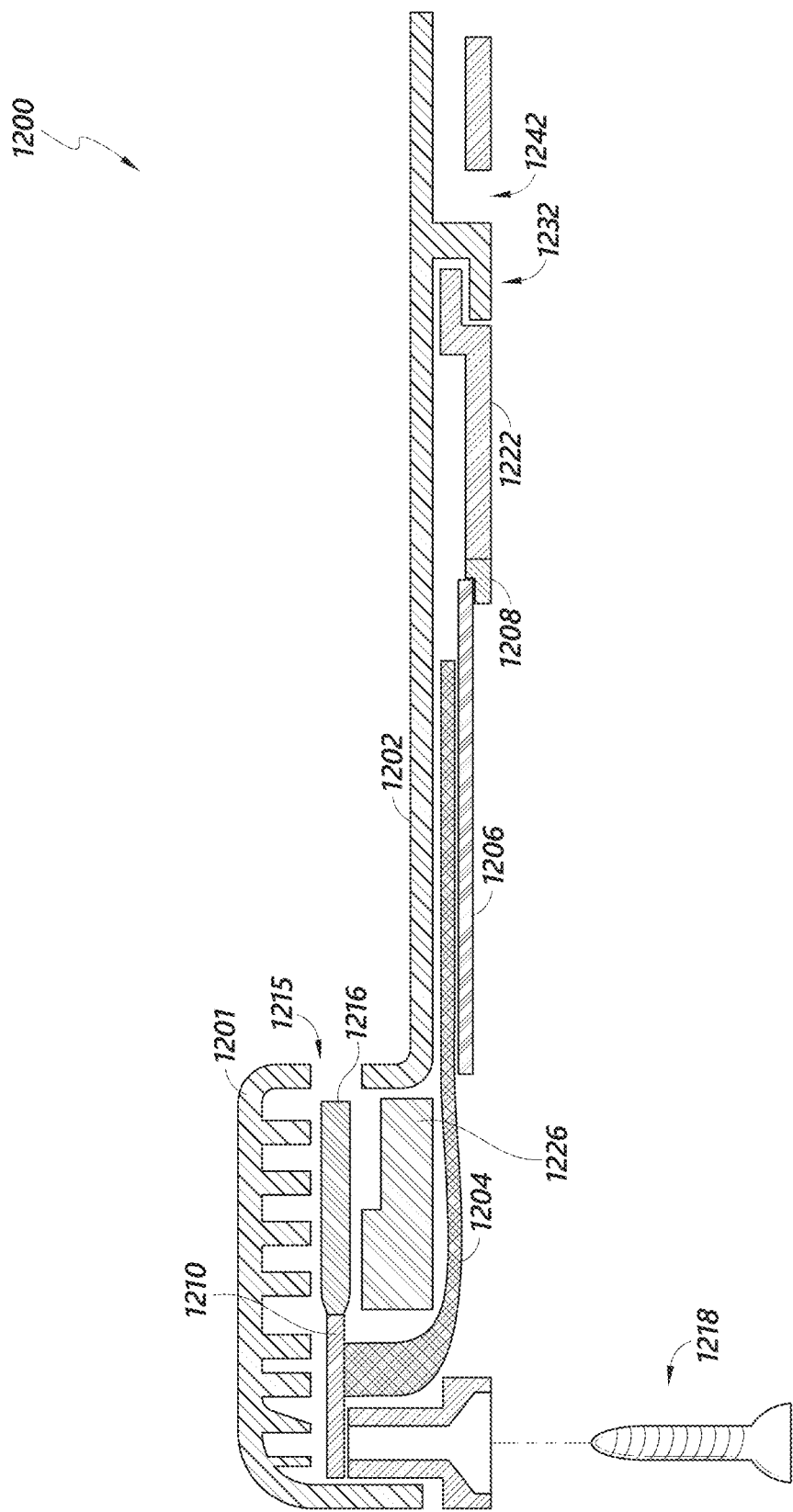
FIG. 12A illustrates a section view of an implementation of a control box connection for the stimulation suit.
Figure 12B:
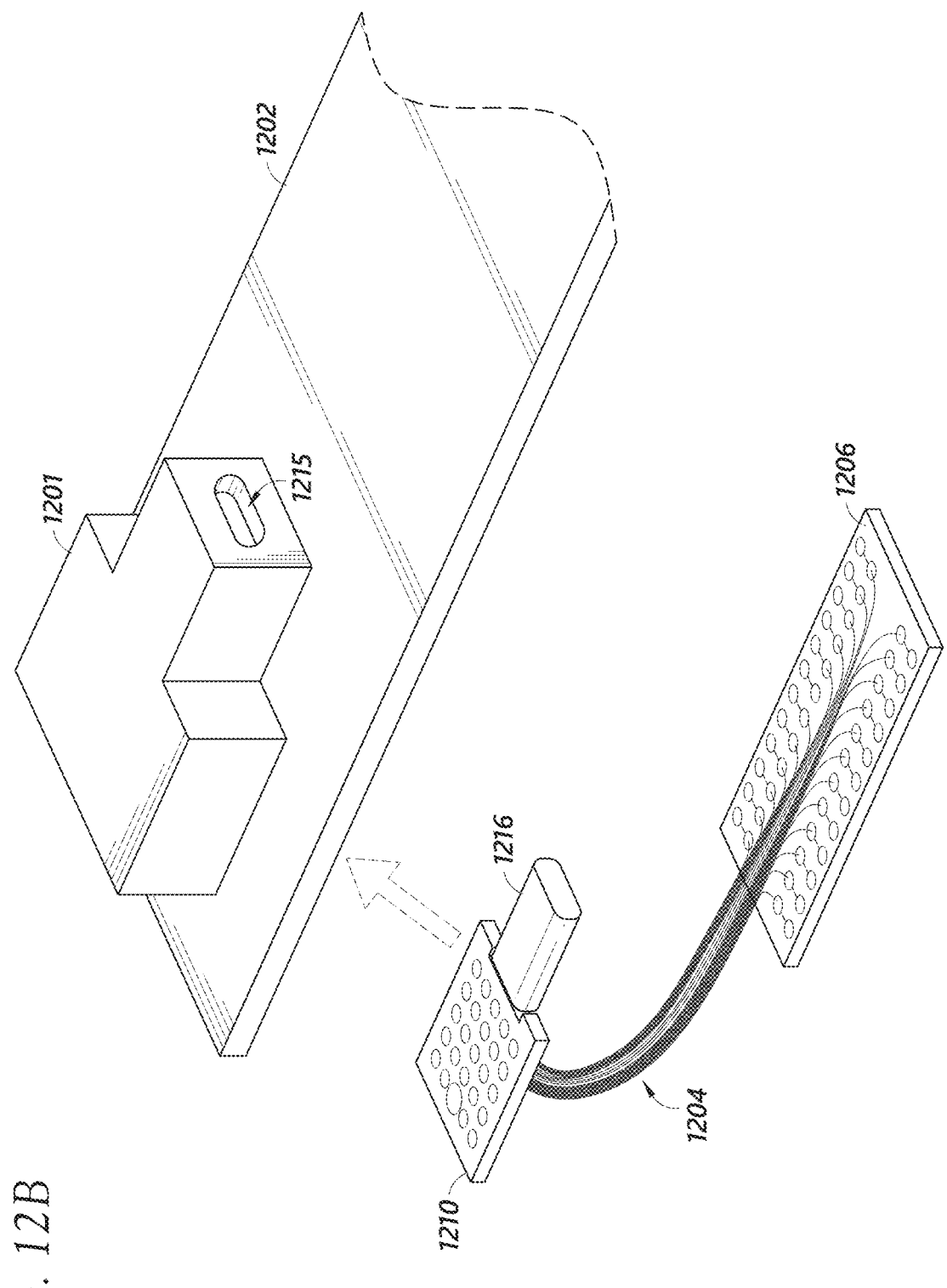
FIG. 12B illustrates an exploded view of a portion of the implementation of the control box connection of FIG. 12A

The inner plate 1222 can also include a housing 1226 for routing, containing, and protecting the wires, such as wires 1204 and outer PCB, such as PCB 1210. Housing 1226 includes a cavity for holding the outer PCB and an opening 1215 or other recess for the connector, such as connector 1216. In some implementations, the housing 1226 extends outward from the inner plate 1222 to connect with the mating housing, for example cover 1201, of the outer plate 1202. In other implementations, the cover 1201 of outer plate 1202 extends inward to mate with housing 1226 of outer plate 1202. In still other implementations, the mating housings 1201/1226 both extend toward each other, as illustrated in FIG. 12A. The cover 1201 and housing 1226 individually or cooperatively form opening 1215 to allow protected access to the connector 1216.

Part of the housing 1226 can further include a through-hole, for securing the inner plate 1222 to the outer plate 1202, for example with screw 1218 or other fastener. In addition to the screw attachment 1218, the inner plate 1222 can include slot 1242, to mate with a clip 1232 and secure the end of the plates 1202 and 1222 together.

Figure 13A:
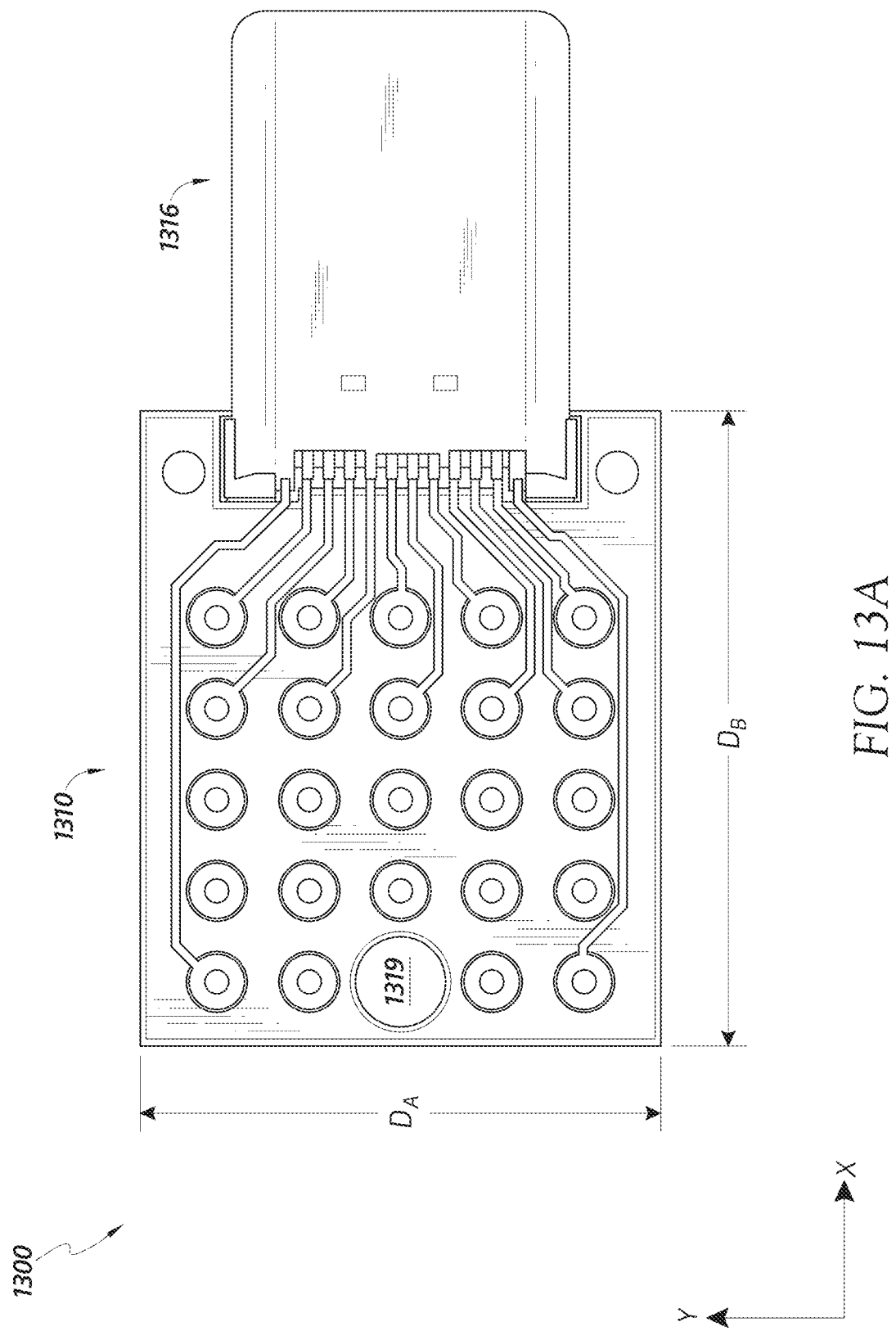
FIG. 13A illustrates an implementation of an outer printed circuit board of the control box connection of FIGS. 12A-B.
Figure 13B:
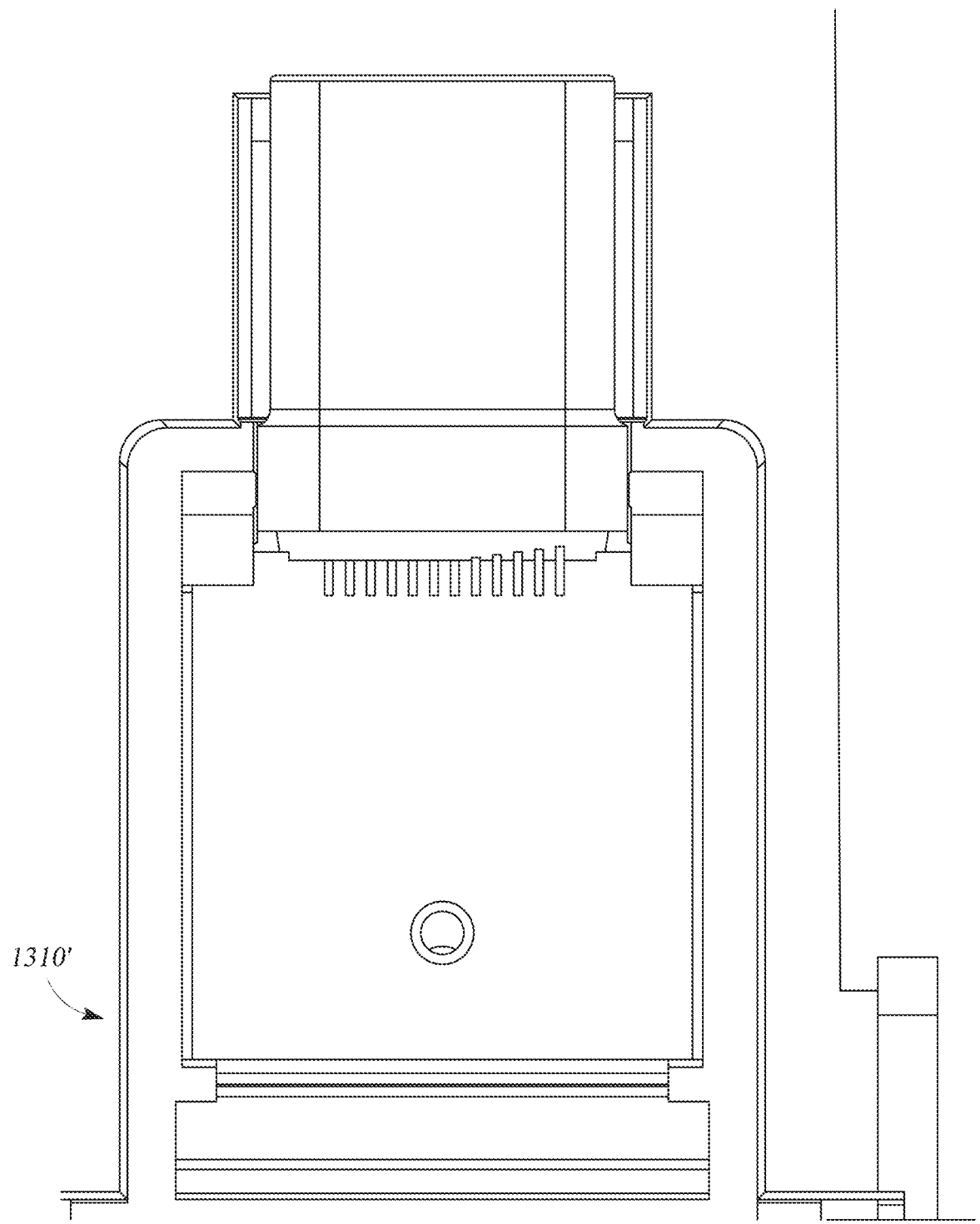
FIG. 13B illustrates an implementation of an outer printed circuit board of the control box connection of FIGS. 12A-B.

The electrical connector 1216 is attached to the exterior PCB 1210. FIG. 13 illustrates one example assembly 1300 including the exterior PCB 1210. In example assembly 1300, USB-C connector 1316 connects to the board 1310. In this example, the external PCB 1310 has dimensions DA and DB of 12.4 mm and 15.2 mm respectively, although any suitable dimensions can be selected as appropriate. For example, some embodiments, such as board 1310' shown in FIG. 13B, can have different dimensions and/or shapes with notches, holes, and the like for better fit and/or alignment within the assembly.

The external board 1310 can include a through-hole 1319 to align and secure the board 1310 in place inside the housing. For example, a fastener, such as screw 1218, optionally fits through hole 1319 to hold external board 1310 in place under the cover 1201.

Figure 14C:
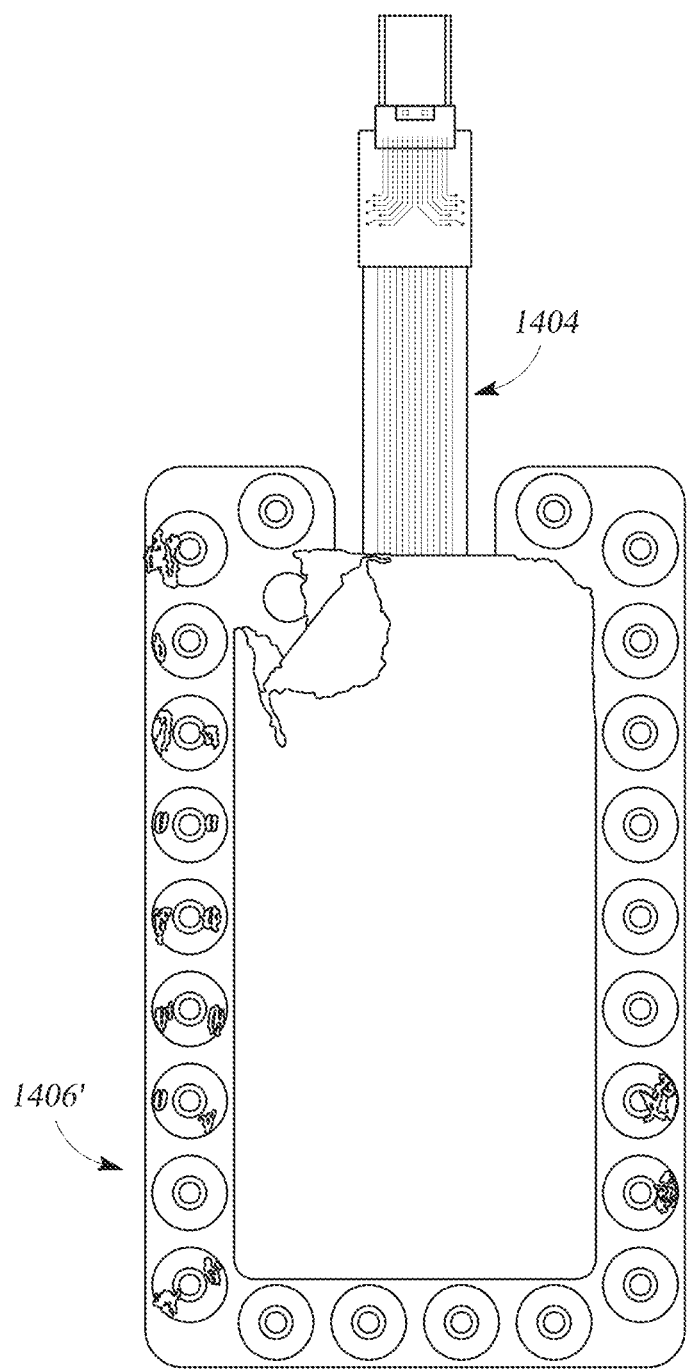
FIG. 14C illustrates an implementation of an inner printed circuit board of the control box connection of FIGS. 12A-B.

The inner PCB 1206 is connected to the exterior PCB 1210 via flexible wires 1204. In some implementations, the inner PCB (e.g., 1206) includes twenty-four connections, as illustrated in example inner PCB 1406 of FIG. 14A. In some implementations, the inner PCB 1206 is a two-sided board, as shown in example inner PCB 1406 of FIGS. 14A-B. The example implementation of FIGS. 14A-14B, inner PCB 1406 has dimensions $D_{10}$ and $D_{11}$ of 50.0 mm and 19.0 mm, respectively, and a thickness $D_{12}$ of 1.0 mm. In other implementations, the inner PCB size, number of connections, and layout can vary as appropriate. For example, on suits 110 with a small number of electrodes 1 and/or sensors 7, 10, the inner PCB can be smaller, such as the length $D_{10}$ of 25 mm and twelve double-sided connections, or a width $D_{11}$ of 10 cm and a length $D_{11}$ of 50 mm with twelve single-sided connections. In some implementations, the inner PCB includes the same twenty-four double-sided connections on the same size board as inner PCB 1406 of FIG. 14A, but some connections are not used. In some implementations, the inner PCB 1406' can include connections at the edges of the board, as shown in FIG. 14C, and can also include a flat or ribbon cable 1404 for connection to the other components.

Figure 15:
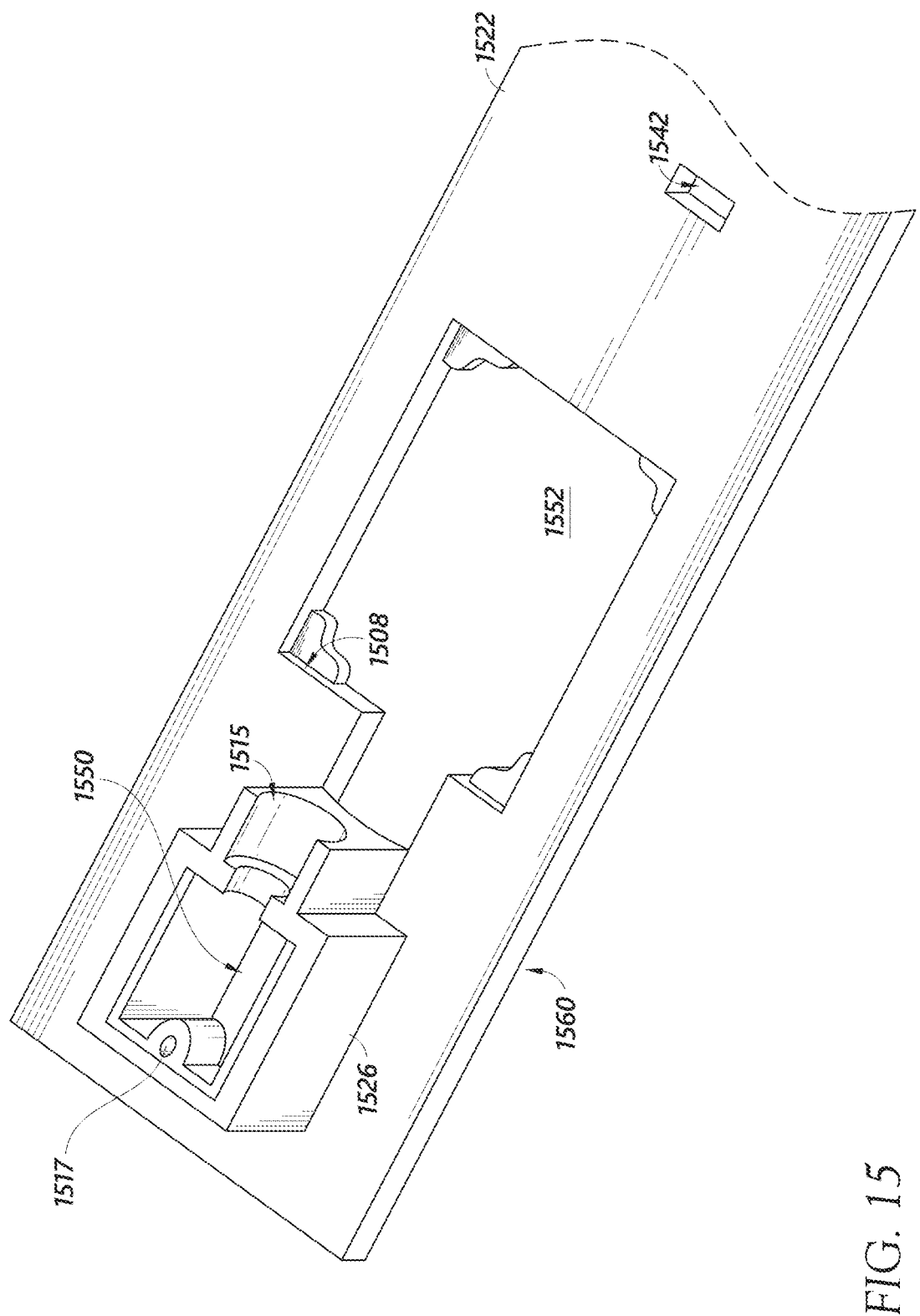
FIG. 15 illustrates an implementation of an inner plate of the control box connection of FIGS. 12A-12B.

FIG. 15 illustrates another implementation of an inner or lower plate of a controller connection area 130. Various elements of inner plate 1522 can be the same as or similar to the lower plate 1222 in some or all respects. For example, inner plate 1522 can include a slot 1542 similar to slot 1242 that mates with clip 1232. Inner plate 1522 can also include an opening or recess 1552 for an inner PCB, such as PCB 1206 or 1406. The opening 1552 can optionally include a clip or notch 1508, similar to support 1208, to hold the inner PCB 1206, 1406. The inner plate 1522 can also include a housing 1526 for routing, containing, and protecting the wires, such as wires 1204, and an outer PCB, such as PCB 1210 or 1310. As illustrated, housing 1526 can include a cavity 1550 for holding the outer PCB and a recess 1515 for the connector, such as connector 1216. Housing 1526 can further include at least one hole 1517 to help secure inner plate 1522 to an outer plate, for example outer plate 1202. Hole 1517 can be used to hold a mating alignment pin, a screw (such as screw 1218), or other fastener. In accordance with several implementations, the thickness 1560 of the inner plate 1522 is small so the inner plate 1522 is sufficiently flexible. For example, the thickness 1560 can be approximately 2 mm, although other dimensions are also suitable, depending on the desired levels of rigidity, comfort, and materials.

Figure 16C:
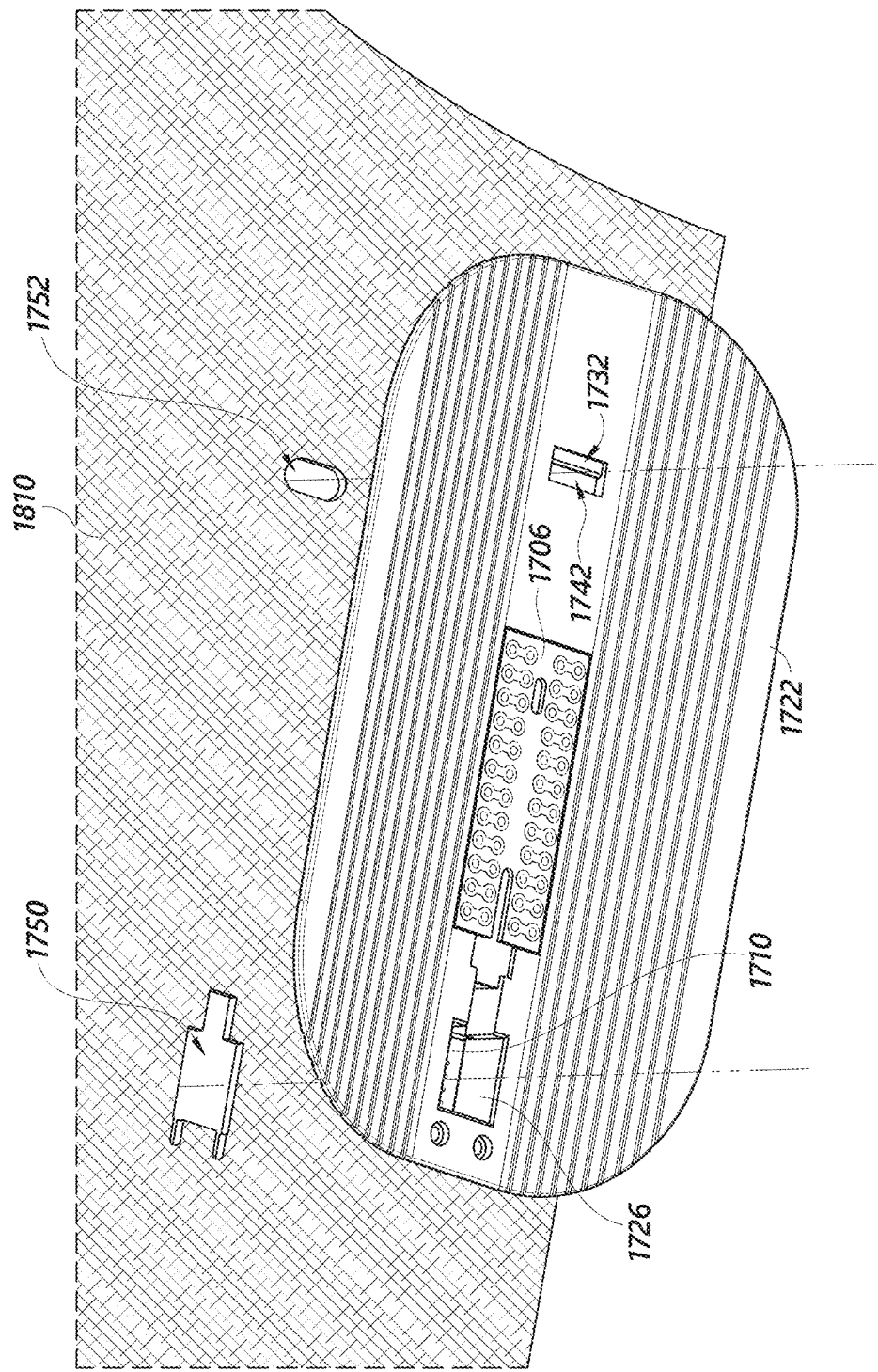

FIGS. 16A to 18B illustrate another implementation 1700 of connection area 130 of suit 110. Various elements of connection 1700 can be the same or similar to the connection elements of FIGS. 12-16 in some or all respects. FIG. 16A illustrates a top or external view of a portion of the connection 1700, and FIG. 16B shows a sectional view taken along line FIG. 16B-FIG. 16B. A bottom or internal view of the same connection 1700 is illustrated in FIG. 16C.

Outer plate 1702, including clip 1732, opening 1715, and cover 1701 can be similar to outer plate 1202, including clip 1232, opening 1215, and cover 1201. Outer plate 1702 can also include securing groove 1734 to optionally mate with a retention pin on the back of a control box 122. Internal circuit board 1706, external circuit board 1710 with electrical connector 1716, and the connecting wires (not shown) can be similar to internal circuit board 1206 or 1406, external circuit board 1210 or 1310 with electrical connector 1216 or 1316, and connecting wires 1204.

Inner plate 1722, including retention slot 1742 and housing 1726 can be similar to inner plate 1222 with retention slot 1242 and housing 1226. Clip 1732 can releasably snap into slot 1742 through hole 1752 in suit 1810. The clip 1732 and slot 1742 cooperate to secure outer plate 1702 to inner plate 1702 and sandwich the circuit boards 1706 and 1710 and the suit 1810 in place. Housing 1726 of the inner plate 1722 and cover 1701 of the outer plate 1702 mate to enclose the external circuit board 1710 and electrical connector 1716. The mating housing 1726 and cover 1710 cooperate to protect the circuitry (e.g., internal circuit board 1706, external circuit board 1710, and the connecting wires) as they cross from inside the suit 1810 to outside the suit 1810 through hole 1750.

As above, housing 1726 and cover 1701 may individually or collectively form opening 1715 to access the electrical connector 1716. In the illustrative connector 1700, cover 1701 forms the opening 1715. The housings 1726 and cover 1701 can be nested or partially nested. For example, cover 1710 fits over at least a portion of housing 1726. The cover 1710 and housing 1726 can be held with a screw, such as screw 1218, or other means of securing the parts, such as friction fit, clip, pin, adhesive, and/or other suitable connector(s). In some implementations, multiple pins, clips, and/or screws can secure the housing 1726 and cover 1710. As above, in some implementations, external circuit board 1710 can include a through-hole (such as hole 1319) for securing and/or aligning the board 1710.

Figure 17A:
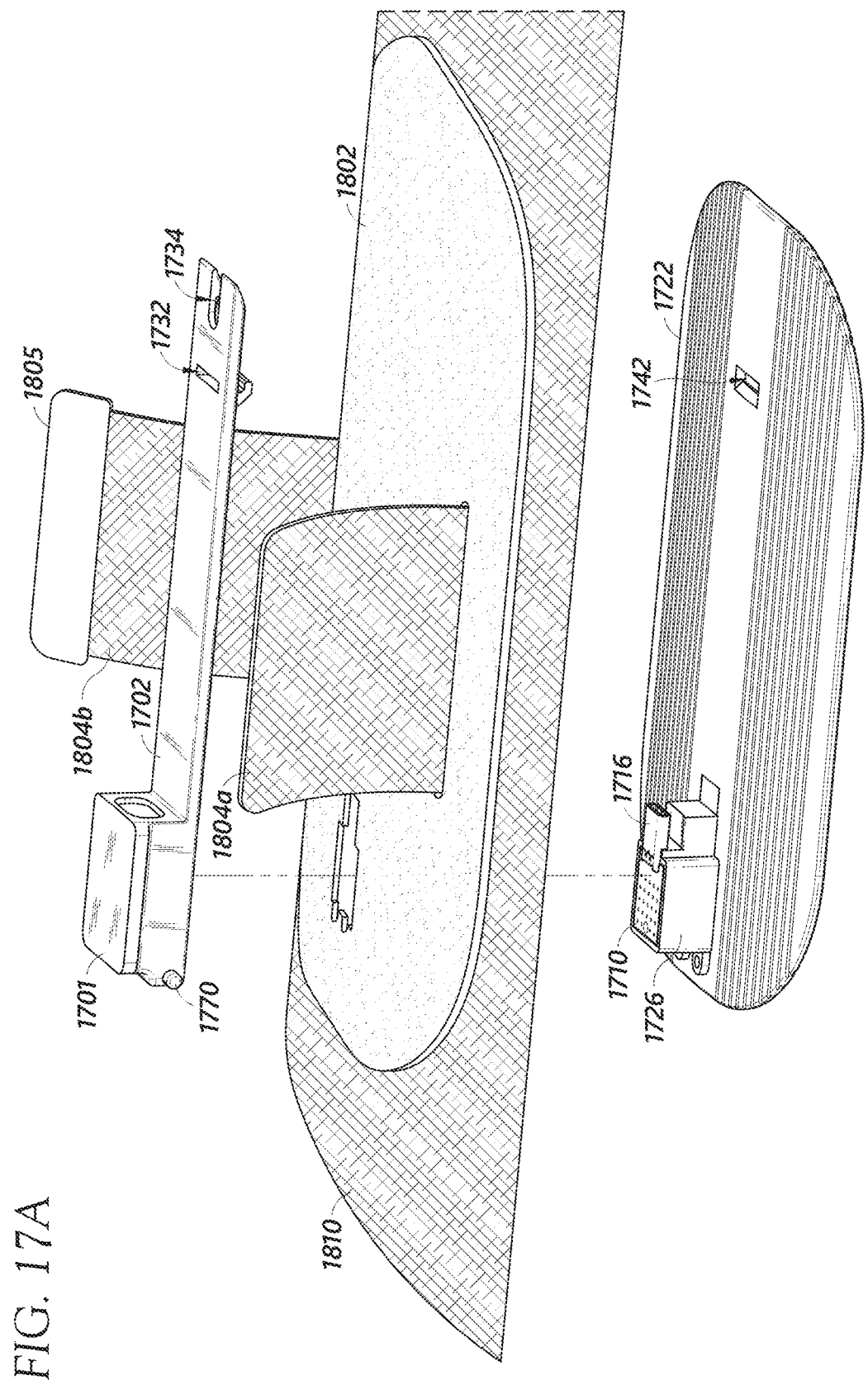
FIGS. 17A, 17B, and 17C illustrate another implementation of a control box connection between the stimulation suit and the control box.
Figure 17B:
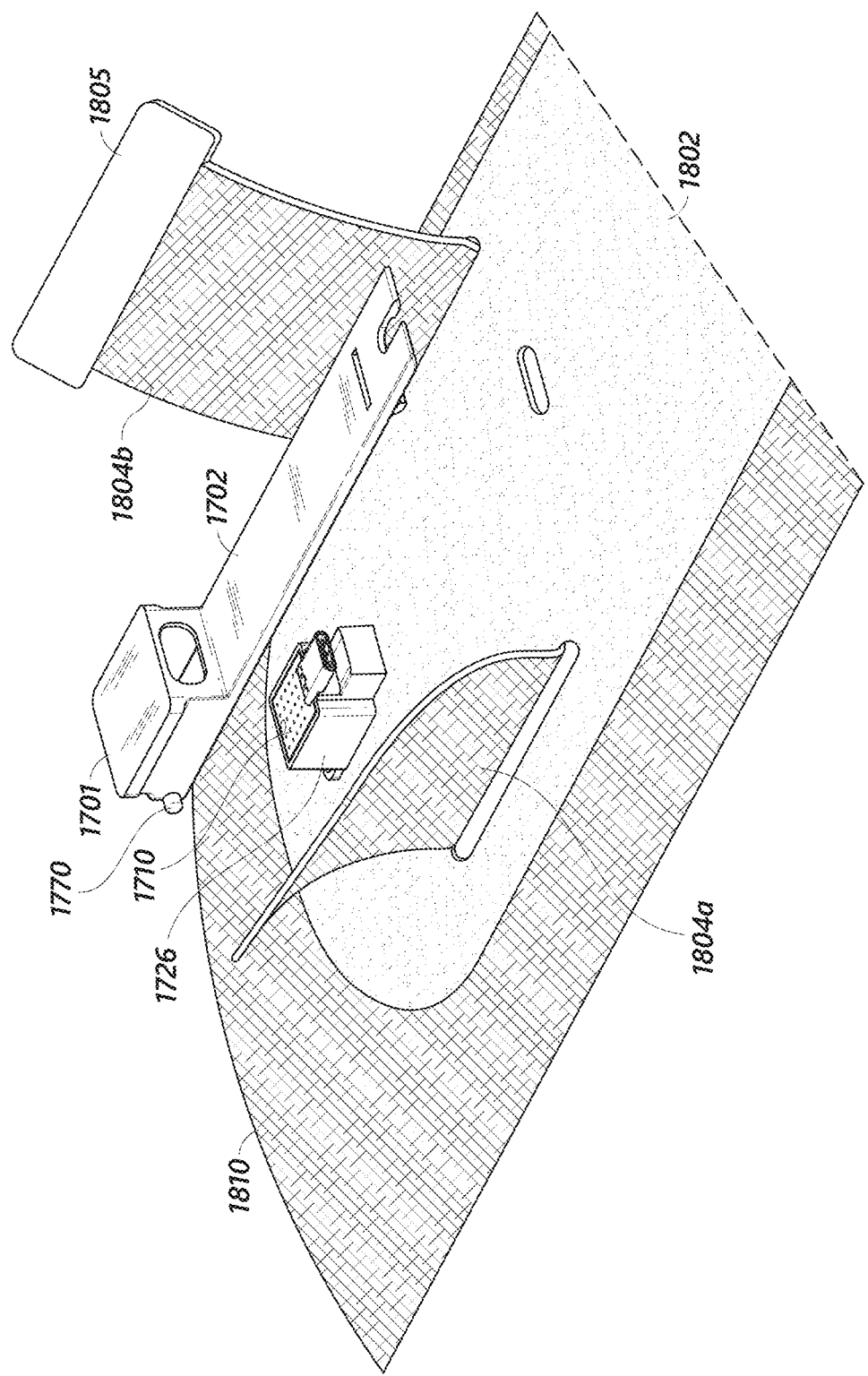
Figure 17C:
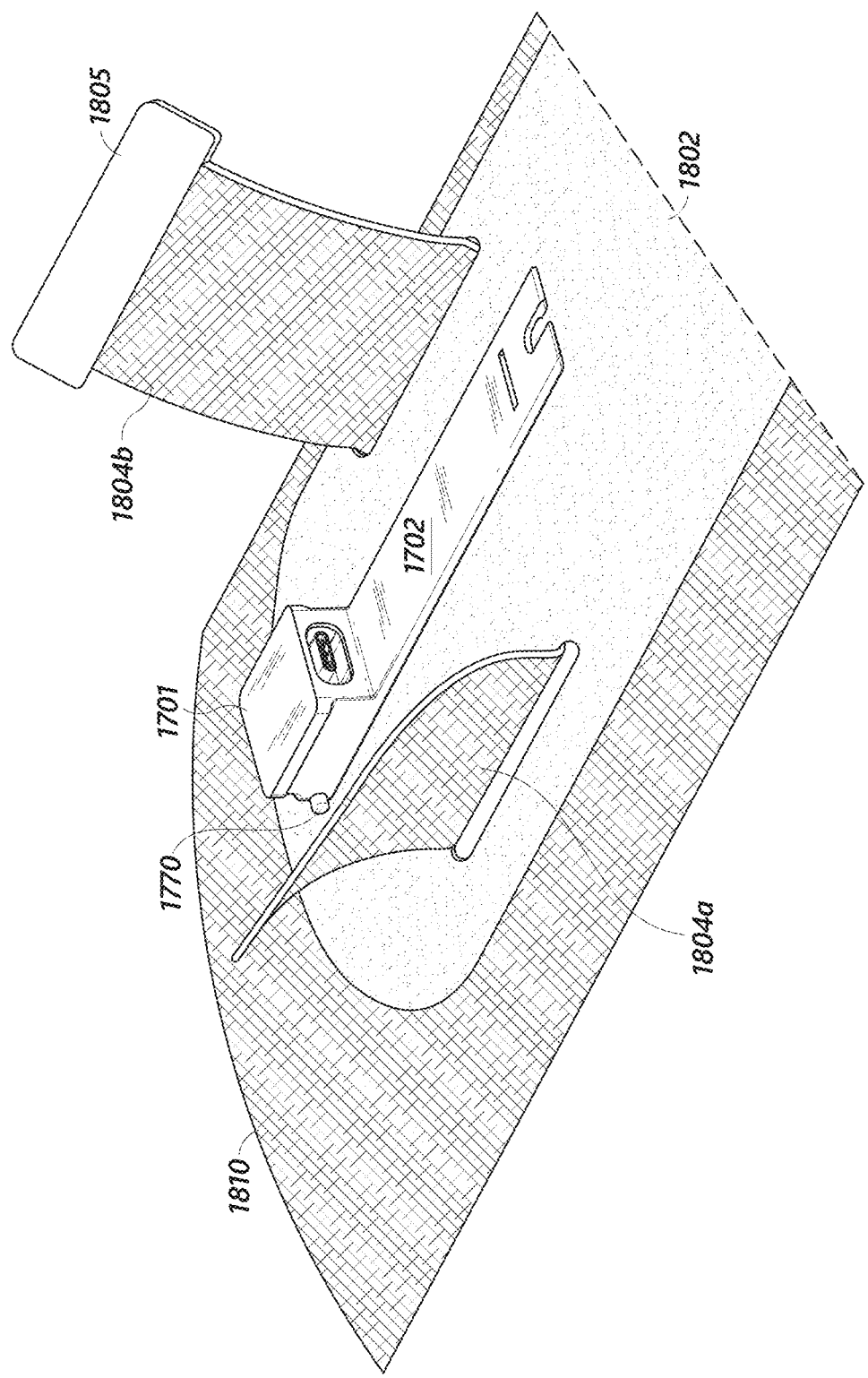

As shown in FIGS. 17A-C and discussed above, outer plate 1702 and inner plate 1722 can connect to each other with the suit 1810 in between. The outer plate 1702 provides a mechanical connection 8 for the control box 122, for example at both securing groove 1734 and cover 1701. An electrical connection 9 is provided at the same connection area 130, for example via electrical connector 1716. An additional mechanical connection 8 can optionally be provided via securing straps 1804a and 1804b. Mating straps 1804a and 1804b can be tightened over or around the control box 122 and fastened together, for example via hook-and-loop attachment 1805. Other additional mechanical connections 8 are also suitable, for example a hook-and-loop strap with buckle as shown in FIGS. 2A, 2B, 4A, 4B, and 6, an elastic band, and/or a pocket.

Figure 18A:
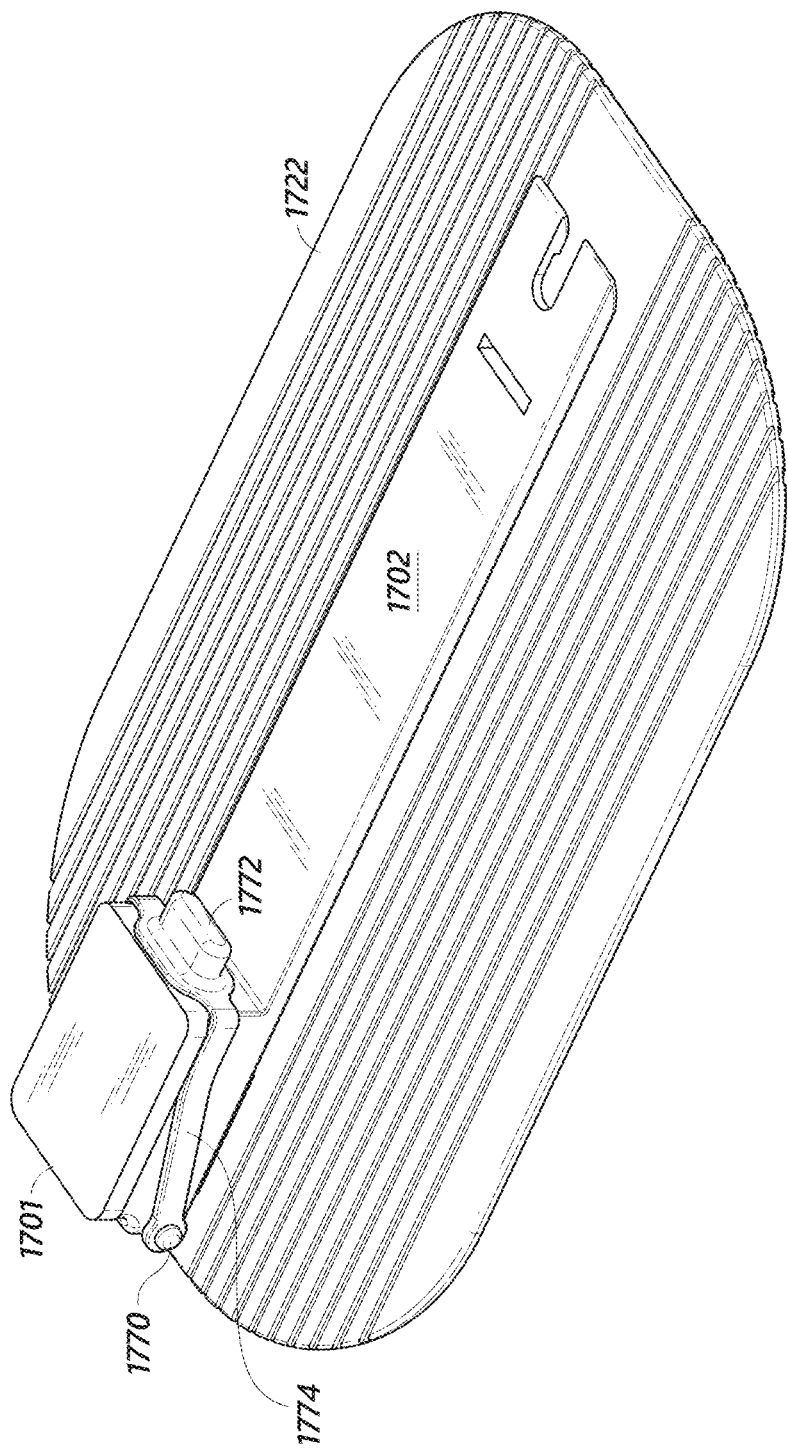
FIGS. 18A and 18B illustrate an implementation of a connection seal of the control box connection.
Figure 18B:
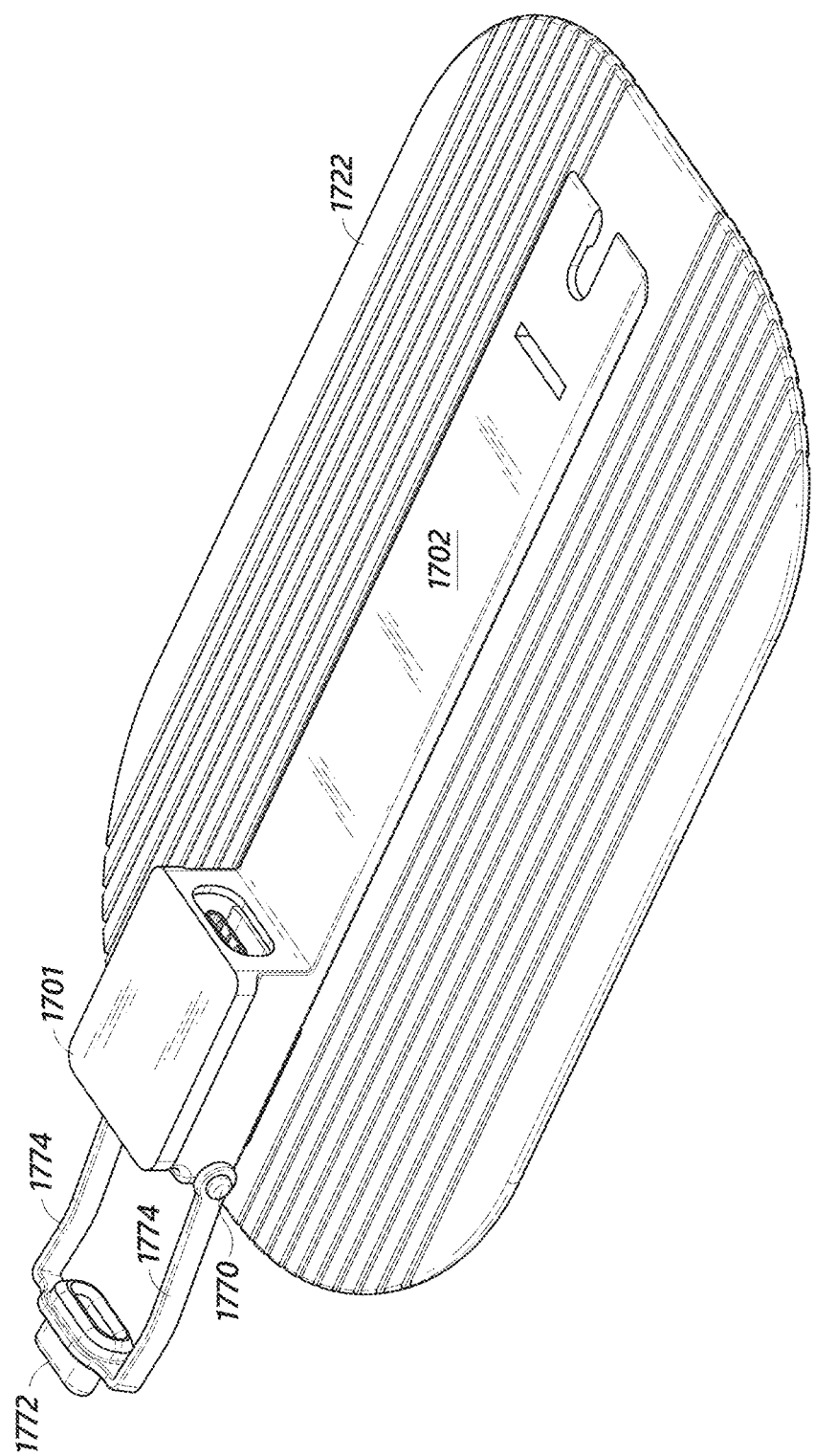

In some implementations, the outer plate 1702 further includes a connection cover 1772. The connection cover 1772 can be secured over the electrical connection 1716, which is similar to connections 1216 and/or 1316 in some or all respects as discussed above. The connection cover 1772 can be secured to the suit 110, 1810. In some implementations, the connection cover 1772 is secured to the outer plate 1702 at pins 1770. As shown in FIG. 18A, when the suit 110, 1810 and/or the connection area 130 is not in use, for example during laundering or if the control box 122 is connected to a different connection area 130 on the other side of the suit, the cover 1772 fits over the connection 1716 to form a seal. In some implementations, the seal is a dustproof and/or watertight seal. As shown in FIG. 18B, the cover 1772 pivots on pins 1770 to expose the connection 1716. In some implementations, the cover 1772 moves to a flattened position and does not interfere with the connection to the control box 122. The cover 1772 can also include arms 1774, which can function as hinge arms (with pins 1770) and/or tethers in some implementations.

Figure 18C:
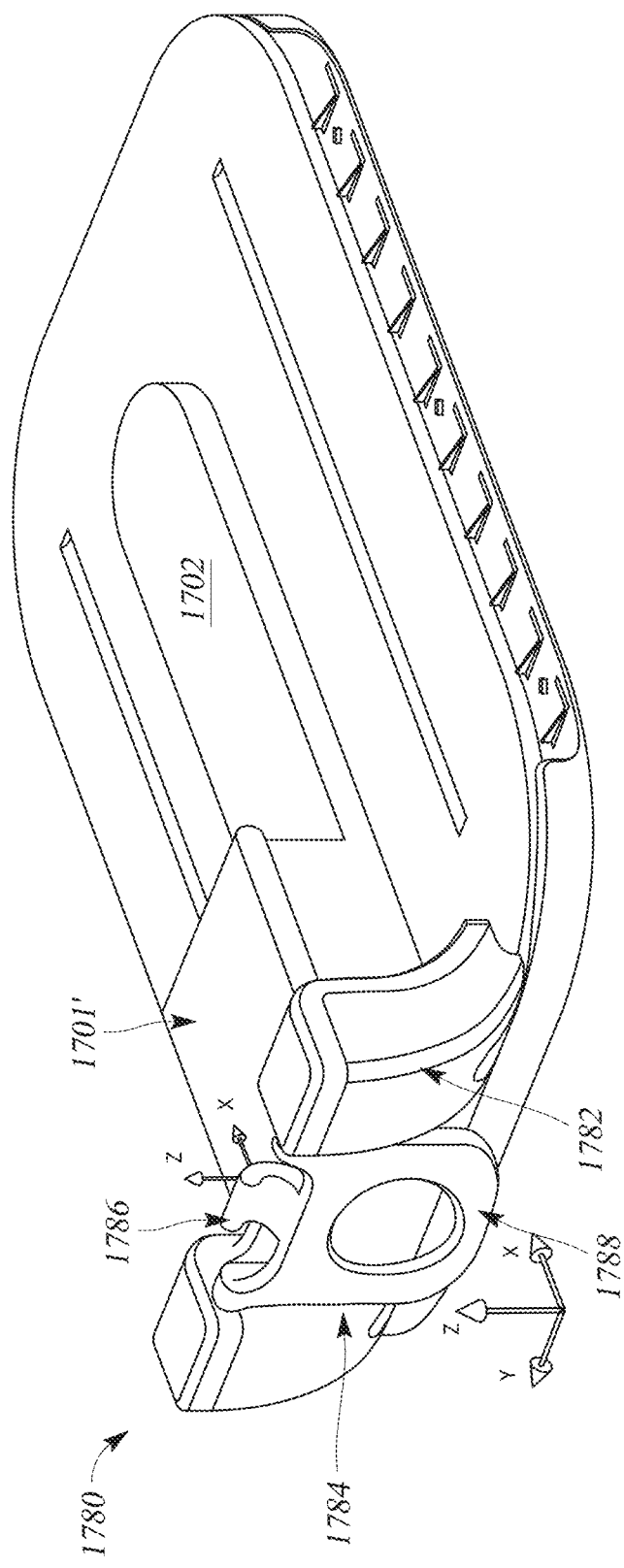
FIGS. 18C, 18D, and 18E illustrate an implementation of a connection lock of the control box connection.
Figure 18D:
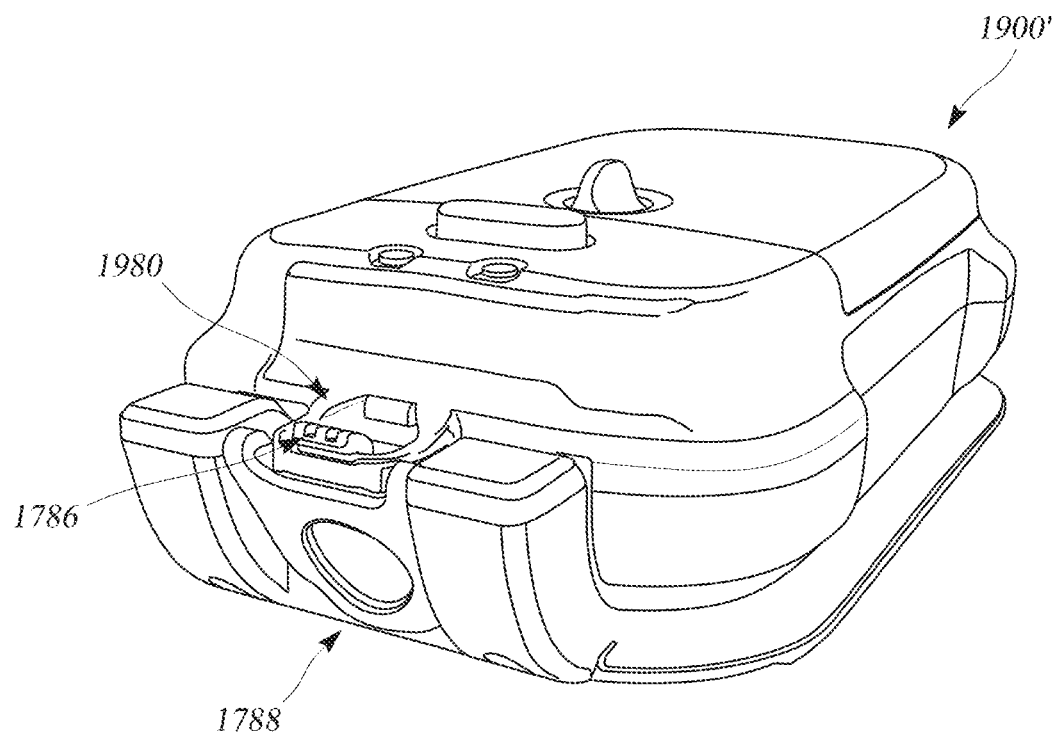
Figure 18E:
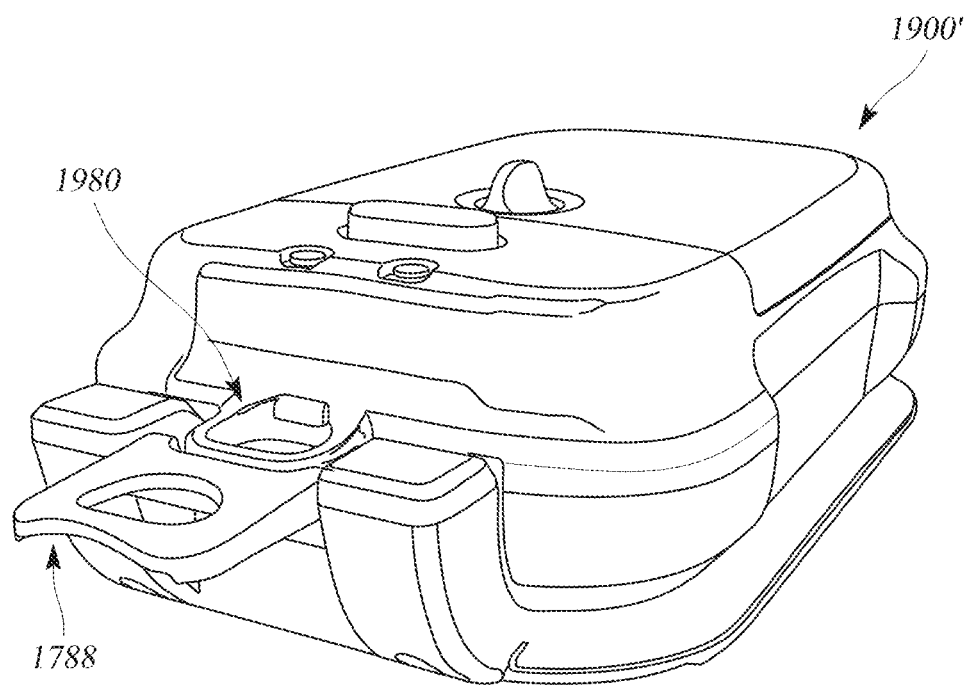

In some implementations, the outer plate 1702 can include a connection lock 1780. As illustrated in FIGS. 18C-E, connection lock 1780 can include a stop 1782 for receiving the back of a control box, for example control box

1900' as illustrated. The stop 1782 can include a latch 1784 with a securing mechanism 1786 and a release 1788. Control box 1900' can include a locking loop 1980, and is otherwise identical to control boxes 122, 1900. When a control box 1900' is engaged over the outer plate 1702 and cover 1701' to form the connection, as discussed above, the locking loop 1980 can engage with the latch 1784. In some implementations, the locking loop 1980 can engage with the securing mechanism 1786, which can be locked in place by pressing or rotating release 1788 down against the stop 1782 to fully raise and lock the securing mechanism 1786. As illustrated in FIG. 18D, when the release 1788 is locked against the stop 1782, the securing mechanism 1786 can lock the locking loop 1980 (and thereby the control box 1900') in place. As illustrated in FIG. 18E, raising the release 1788 can rotate the securing mechanism 1786 down and away from the locking loop 1980 to allow the control box 1900' to be removed.

In some implementations, seating the control box 1900' against the stop 1782 partially or fully engages the latch 1784. In some implementations, the latch 1784 can include a cam arranged to increase friction against the control box 1900' and improve stability of the connection. In some implementations, the latch 1784 can include multiple latches, levers, hooks, or other releasable engagement mechanisms. In some implementations, the mating locking loop 1980 can be a circular loop as shown in FIGS. 18D-18E, although other shapes such as D-rings, ovals, slots, tabs, etc. may also be suitable. Similarly, release 1788 can include a circular loop or pull ring as shown in FIGS. 18C-18E, but other configurations, such as buttons, levers, tabs, etc. may also be used.

In the examples illustrated in FIGS. 12-18, the electrical connectors 1216, 1316, and 1716 are each a USB-C connector, although other standard connectors are also suitable. For example, the electrical connector 416 could be USB-A, mini-B USB, micro USB, FireWire, Lightning, RJ-11, RJ-45 and other suitable connectors.

In some implementations, such as suits 110 and 50, the connection area 130 is located on one side of the suit. In other implementations, the suit 110, 50 includes multiple connection areas 130 with associated signal pathways 2, where one connection area is on one side of the suit and another connection area is on the other side of the suit (e.g., connections and pathways on the left and right sides). In these implementations, the control box 122, including at least stimulation controller 120, can be connected to the first or second connection area 130 to allow the stimulation controller 120 to be conveniently located on either side of the body.

As discussed above, the control box 122, including stimulation controller 120, is generally physically connected to the electrodes 1 and any sensors 7, 10 (permanently or via releasable connector). Optionally, these components can be wirelessly connected. Appropriate wireless protocols include infrared (IR), Bluetooth™, WiFi, Zigbee, and RFID. In some wireless implementations, transmission can occur in frequency bands such as the Industrial, Scientific, Medical (ISM) bands, which include 900 MHz, 2.4 GHz, 5.2 GHz, and 5.8 GHz. In some implementations, all the components are connected wirelessly. In other implementations, a portion of the components are connected wirelessly. In still other implementations, some or all of the components use both wireless and wired connections. In implementations where wireless communications are used, the connected components, for example wireless sensors 7, 10, further include a transmitter, receiver, or transceiver and an appropriate power source. In some implementations with wireless electrodes, the electrodes 1 may include an integrated power source and signal amplification or an integrated signal generator. In some implementations with wireless sensors, the sensors (e.g., sensors 7, 10) may have integrated amplification, A/D converters, and/or memory cells for calibration, allowing for some signal conditioning directly on the sensor before transmission.

Control Box

The control box 122 includes a stimulation controller 120 that is attached to the suit, for example suit 110, 50, or 1810, at a connection area 130. The stimulation controller 120 provides electrical stimulation signals to the electrodes 1 over the signal pathway 2. In some implementations, the stimulation signal includes the frequency, pulse width, wave form (length and amplitude), duration, time period (rest) between signals, and/or duty cycle to each electrode 1 sent via the signal pathway 2 and electrical connection 9. In several implementations, the signal is sent every 12-350 milliseconds, but transmissions are not limited to that time span. In accordance with several implementations, the stimulation controller 120 can be detachably connected to the signal pathway 2 and suit 110, and can be moved from suit to suit as discussed above. The electrical stimulation signals provided to the electrodes 1 advantageously cause a contraction of the target musculature and/or nerve stimulation.

In some implementations, the stimulation controller 120 is housed in a tablet/pad, laptop, desktop computer, cell phone, smartphone, or other portable computing device and connected to the electrical connection 9 at the connection area 130 and signal pathway 2 of the suit 110. In many implementations, the stimulation controller 120 is housed in a control box, such as box 122 in FIGS. 7-8 or box 1900 in FIGS. 19A-E. In many implementations, the control box 122 includes a transceiver to communicate with the software 150 (e.g., communications interface module or unit) on manager device 152. In many implementations, the transceiver is a wireless transceiver. Appropriate wireless protocols include infrared (IR), Bluetooth™, WiFi, Zigbee, and RFID. In some wireless implementations, transmission between the control box 122 and the software 150 (e.g., communication interface of the computing or processing device implementing or executing the software 150 stored in memory or non-transitory computer-readable storage medium) can occur in frequency bands such as the Industrial, Scientific, Medical (ISM) bands, which include 900 MHz, 2.4 GHz, 5.2 GHz, and 5.8 GHz.

In some implementations, the control box 122 optionally includes user interface elements, such as buttons, switches, lights, speakers, displays, and other input and feedback devices. Some interface elements may be inside the control box 122, while others are on the external surface. In some implementations, the control box 122 includes a power switch and power indicator LED. In some implementations, the control box 122 optionally includes a location switch that can be used to indicate if the stimulation controller 120 is connected from the left or right side of the suit, if the stimulation controller 120 is connected at a home, an athletic facility, a rehabilitation setting, etc. In some implementations, a switch can be used as an emergency stop.

For example, control box 122 can include user interface elements, such as a switch and/or indicator light. In some implementations, the switch is a power switch 11. In some implementations, multiple switches are included for power on/off, stimulation start/stop, event marking, assistance request, and the like. In some implementations, the switch is a pushbutton switch, although other switches, such as momentary, rocker, blade, and slide switches are appropriate. In some implementations, indicator lights 12 are LED lights. In some implementations, indicator lights 12 are LED lights that indicate power on/off states, battery charge status, connectivity status, and/or error conditions. In the implementation illustrated in FIGS. 19A-E, control box 1900 includes button 1902 and lights 1904 that may be similar to switch 11 and lights 12 in some or all respects. In some implementations, the control box 122, 1900 can include an integrated switch 11 and light 12, for example an illuminated or backlit switch.

The control box 122 may include a power source connected to the stimulation controller 120. In some implementations, the power source is also connected to a user interface, signal acquisition unit, and/or transmitter. In some implementations, the power source is a DC power supply such as a battery. In some implementations, the battery includes a main battery and a backup battery. In some implementations, the battery is rechargeable. In this case, the control box may also include a charging circuit and/or the system 100 may include a charging cable or station. In some implementations, the battery is located in a battery housing and is optionally removable or accessible via an openable cover of the controller box.

Figure 7:
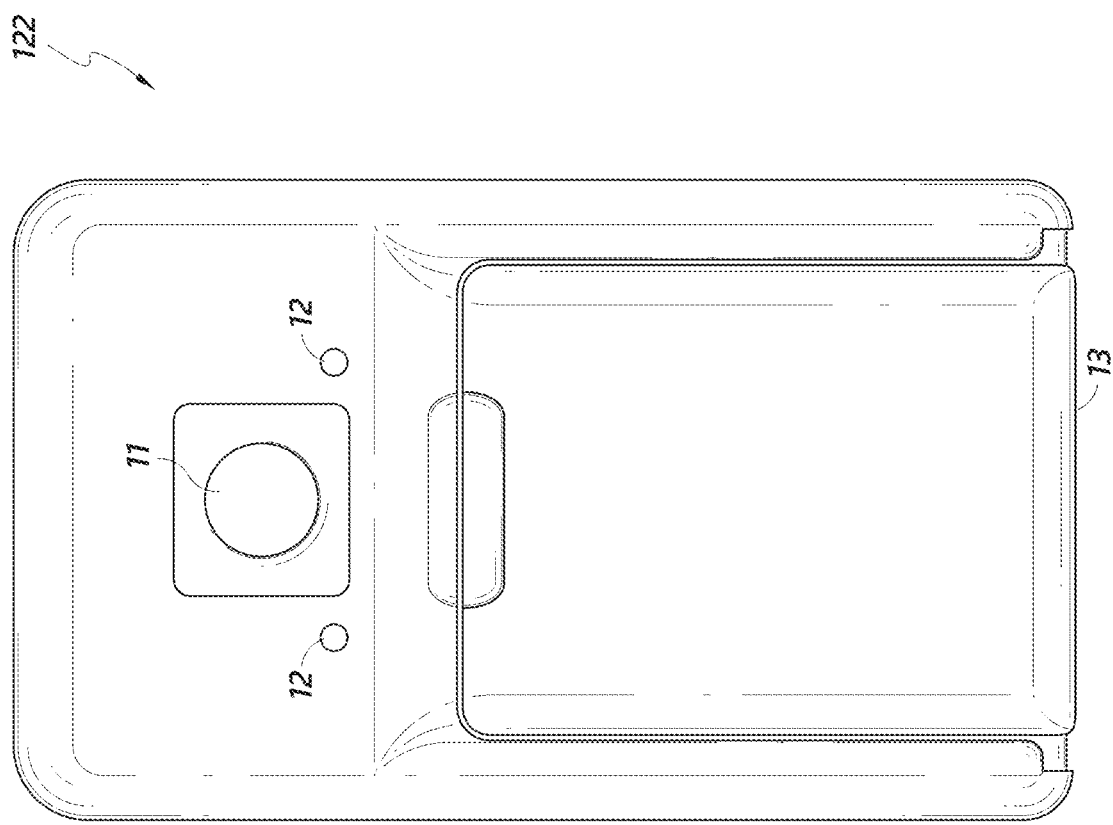
FIG. 7 illustrates an implementation of a control box of the training and rehabilitation system.
Figure 8:
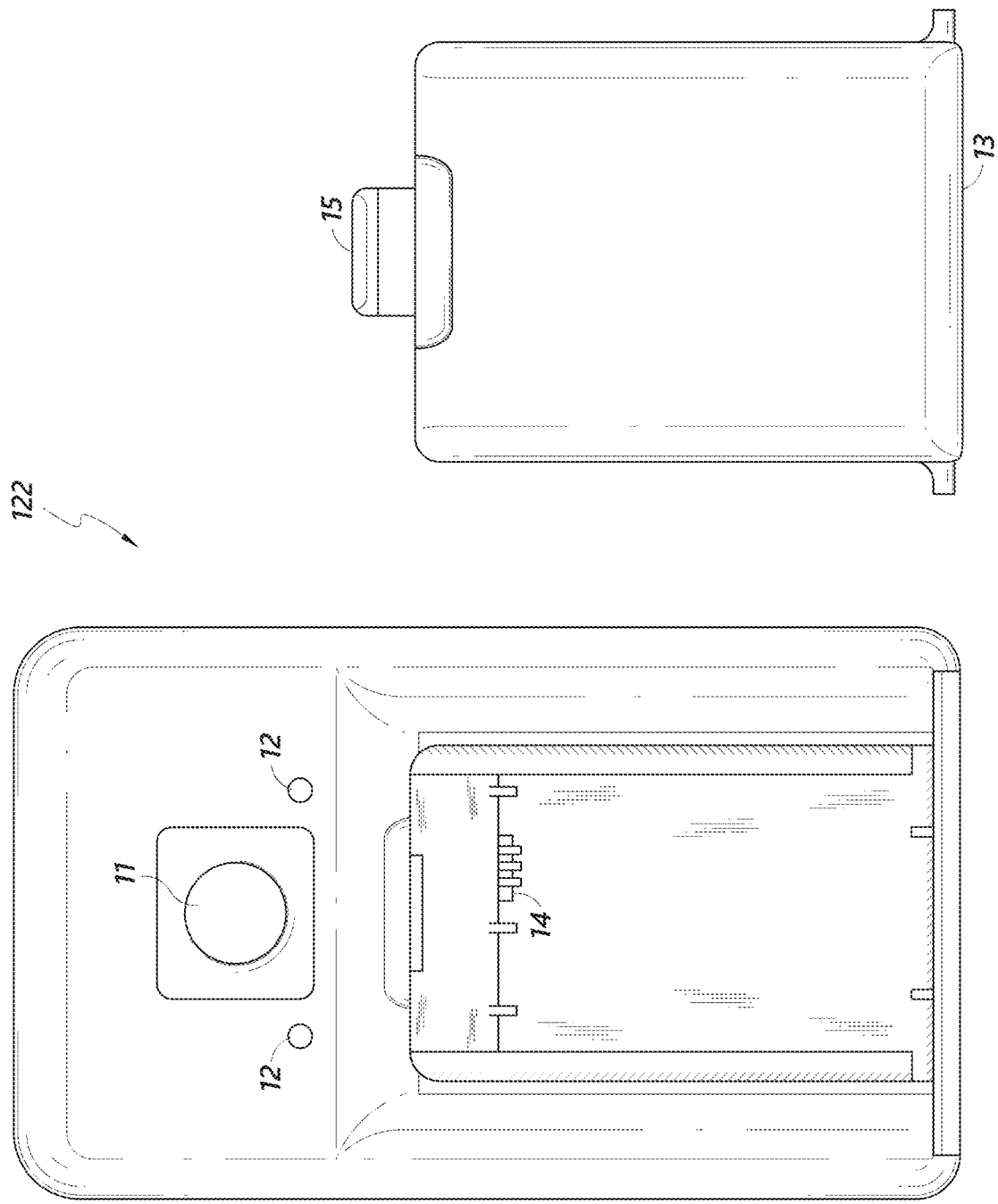
FIG. 8 illustrates the control box of FIG. 7 with the battery cover opened.

With reference to FIGS. 7-8 and 19, control box 122, 1900 includes a power source. In some implementations, the power source is a battery. In some implementations, the power source is a removable battery, such as a removable and rechargeable battery. In some implementations, the battery is a 7.4 V DC rechargeable lithium battery 12. In some implementations, the battery is a set of AA, AAA, C, or other size alkaline or nickel-cadmium batteries. In some implementations, the battery 12 is contained in a compartment with a cover 13. In some implementations, the cover 13 is a removable cover with a retention clip 15. In other implementations, such as the example shown in FIGS. 19A-E, battery 1908 in control box 1900 is secured with a sliding battery cover 1906.

In many implementations, the control box 122 includes a connection port for connecting the signal pathway, for example signal pathway 2, to the stimulation controller 120 and optionally to other elements inside the control box 122 (e.g., a signal acquisition unit). In some implementations, such as those discussed above, the signal pathway 2 is integrated into the suit 110, and the electrical connection 9 includes a male/female connection port sewn into or otherwise attached to the suit 110. The mating male/female connection port is provided on the control box 122. As noted above, in some implementations, the connection port provides both an electrical connection for the stimulation controller 120 and a mechanical connection for the control box 122. In some implementations, the connection area 130 includes a magnetic connection plate, such as connection plate 9 illustrated in FIG. 9. The connection plate 9 can include both metallic leads 17 for the electrical connection and magnet connectors 16 for the mechanical connection 8. In this case, the control box 122 includes appropriate mating metallic and/or magnetic or ferromagnetic connections.

Figure 19A:
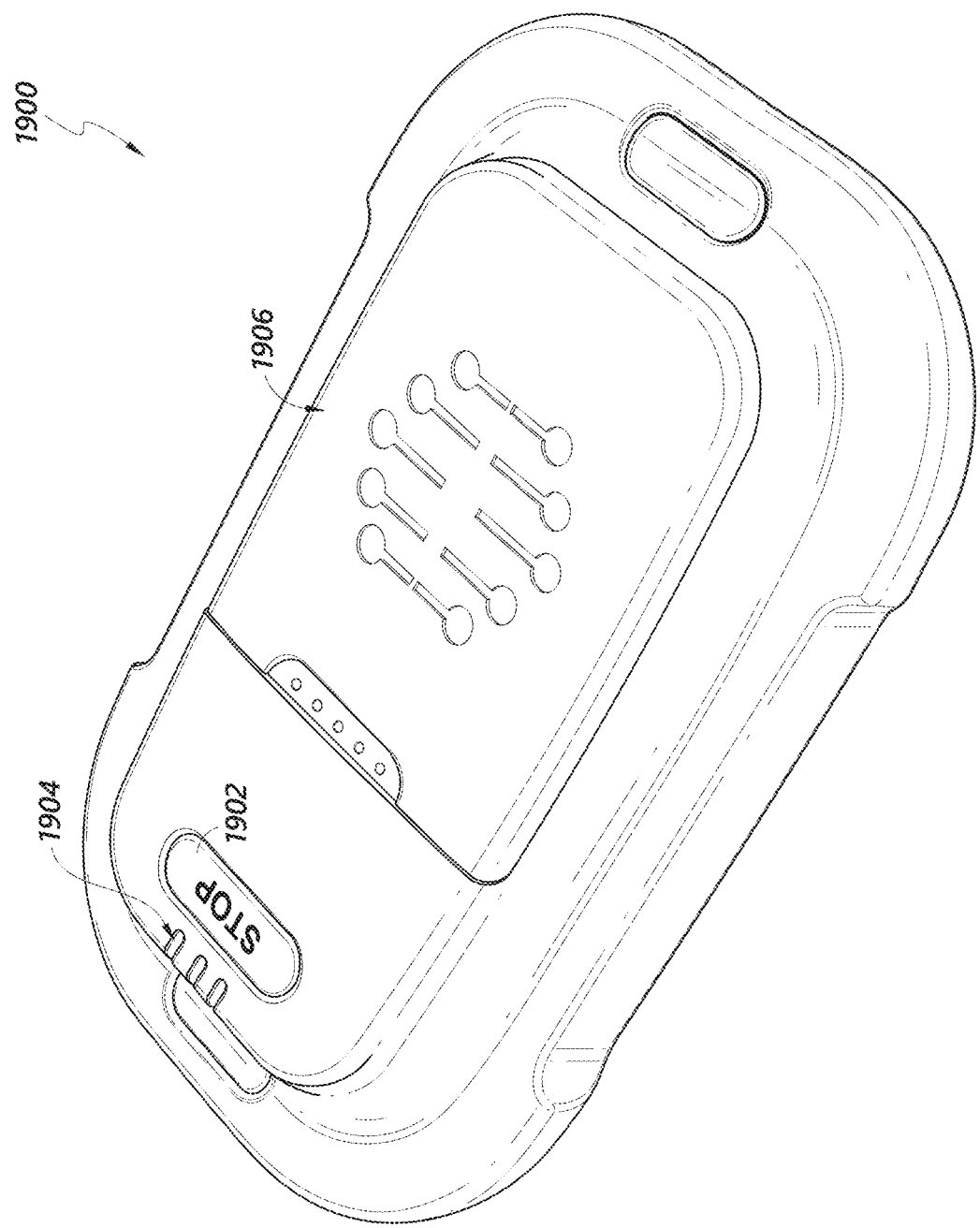
FIGS. 19A, 19B, 19C, 19D, and 19E illustrate an implementation of a control box.
Figure 19B:
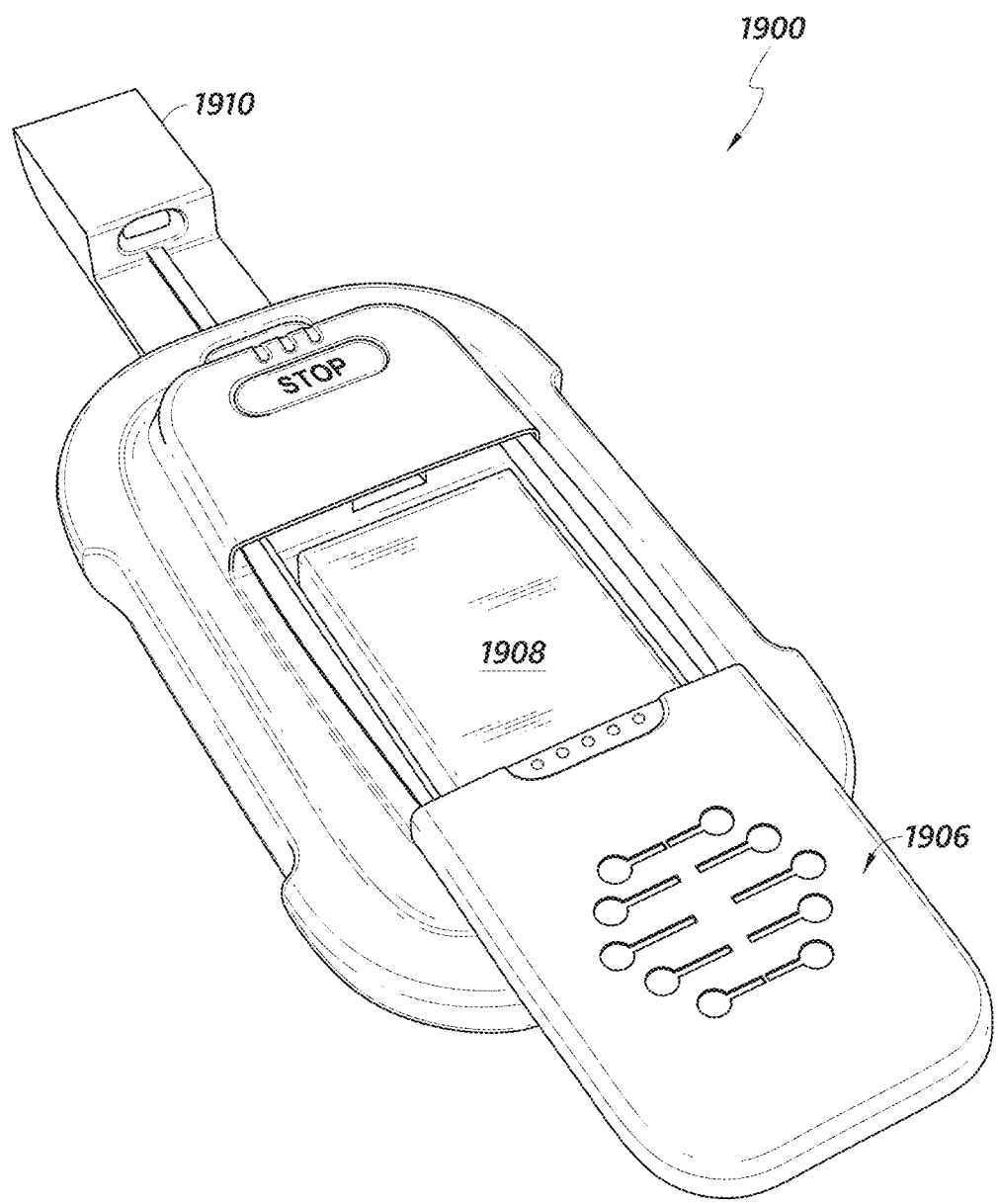
Figure 19C:
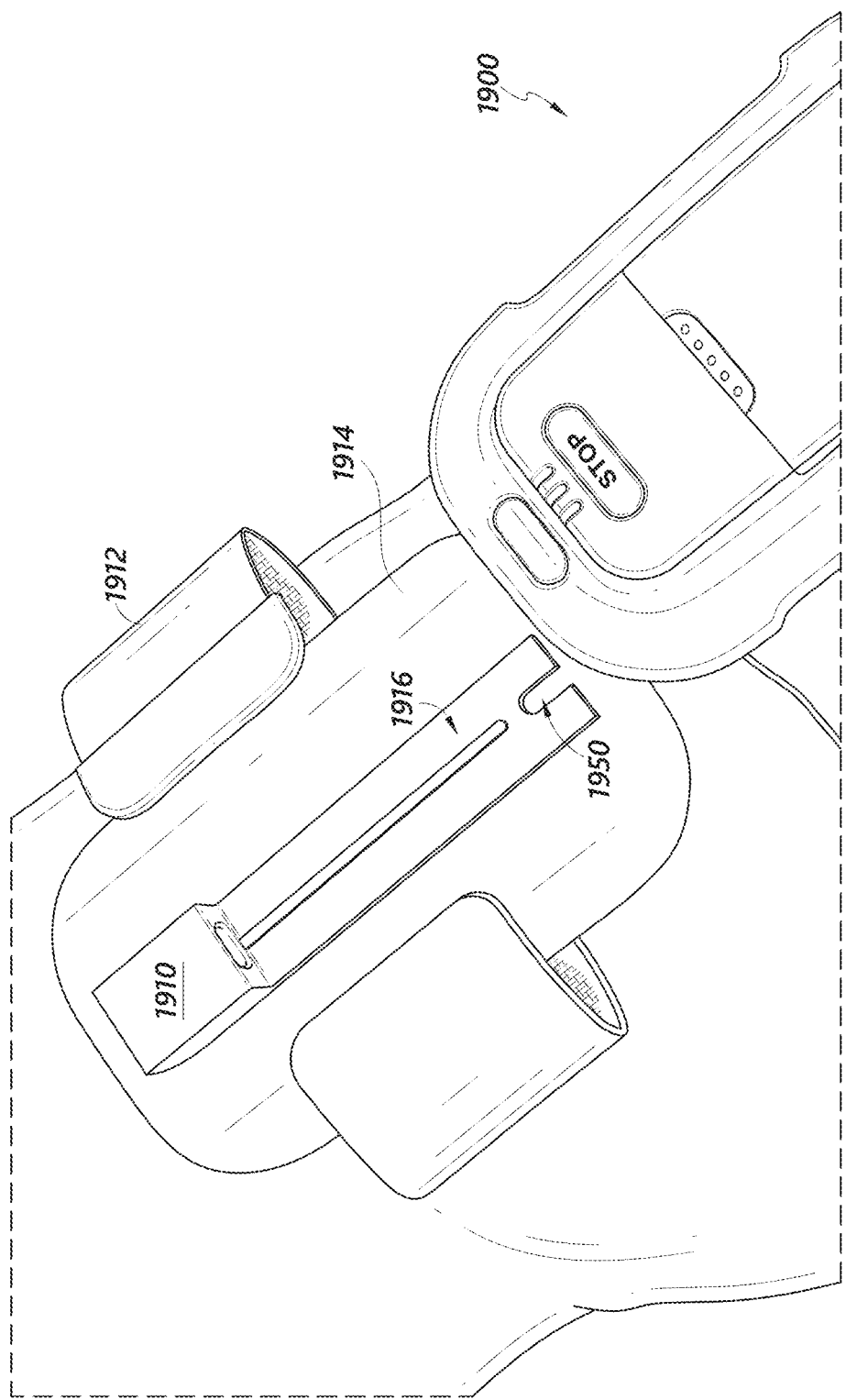
Figure 19D:
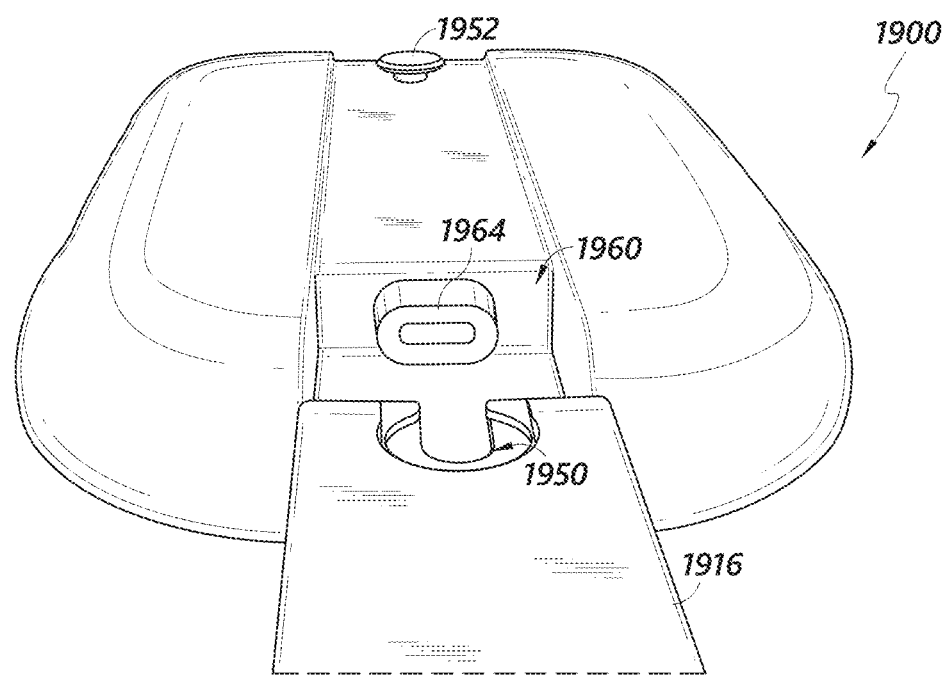
Figure 19E:
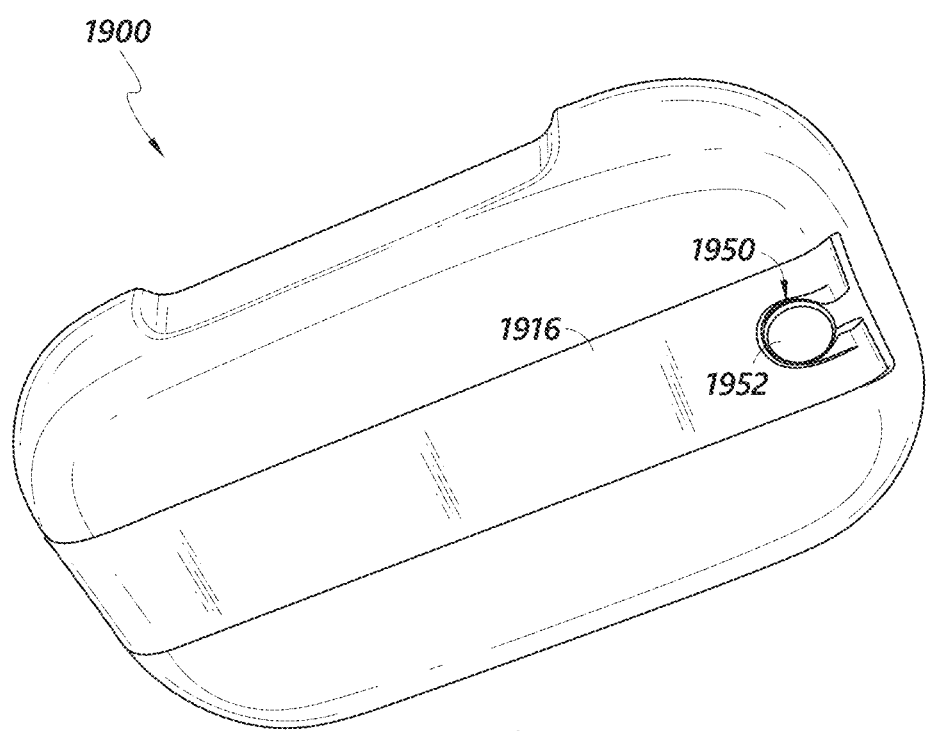

As shown in FIGS. 19C-19E and discussed above with respect to FIGS. 12-18, the control box 1900 is releasably attached to the suit 110 at a connection area 130. In this example, the connection area 130 includes an upper plate 1916 with a housing 1910 containing the electrical connector, securing straps 1912, and a reinforcement or support plate 1914. These features can be similar to the corresponding plates, straps, and connectors discussed above in some or all respects. In some implementations, upper plate 1916 includes an alignment rail used to slide in a mating slot or groove on the back of control box 1900. In this implementation, the upper plate 1916 includes at least one securing shape, such as shaped cover 1910 and securing notch 1950. As illustrated in FIGS. 19C-E, the back of control box 1900 includes mating securing shapes, such as post 1952 and recess 1960. When the control box 1900 is connected to suit 110 at the connection area 130, the upper plate 1916 mates with the back of the control box 1900. In some implementations, securing notch 1950 mates with post 1952 and shaped cover 1910 mates with at least part of recess 1960. These features cooperate to provide at least part of the mechanical connection 8. Additional mechanical connection 8 can be provided by securing straps 1912 over the control box 1900 after it is connected at the connection area 130. The electrical connector inside the shaped cover 1910 (for example, electrical connectors 1216, 1316, 1716) mates with connection port 1964 on the back of the control box 1900. In some implementations, connection port 1964 is located at least partially inside recess 1960 to allow connection port 1964 to connect with the electrical connector 1216, 1316, 1716 to make electrical connection 9 when cover 1910 mates with recess 1960. In some implementations, recess 1960 includes a deep recess for the connection port 1964 that is shaped for the cover 1910, and a shallow recess for upper plate 1916. As illustrated in FIGS. 19D-E, the different areas of the recess 1960 allow the upper plate 1916 to mate with the back of the control box 1900 and provide a flush or smooth surface against the body of the wearer of suit 110.

These connectors are illustrative, and not intended to limit the system 100 to those methods of connection. As noted above, additional suitable connectors include a hook-and-loop strap, a tie down, or a pocket to securely fasten the control box 1900 to the signal pathway 2 and/or suit 110. Other connection implementations include a snap, zipper, button, or variations thereof. The control box 1900 may include mating connections (e.g., snaps, zipper halves, buttonholes, etc.) and/or cooperating hooks, clips, loops, tabs, and the like to secure the control box 1900 to the suit 110 at the connection area 300. These mating features can be provided in addition to or in place of mating features securing notch 1950 and post 1952 and/or mating features recess 1960 and cover 1910. As noted above, in some implementations, the electrical and mechanical connections are separate. In other implementations, the electrical and mechanical connections are integrated or cooperating, such as a conductive metal snap or the conductive magnetic plate connection mentioned above. In some implementations, the electrical connection, mechanical connection, or both, are permanent. In other implementations, the connections are releasable to allow repeated connecting and disconnecting.

In several implementations, the system is modular, and the control box 122, 1900 can be disconnected and moved. In some implementations, such as those discussed above with respect to the signal pathway, the control box 122, 1900 can be moved from a connection port on one side of the suit 110 to a connection port on the other side of the suit 110 (for example, from the right hip to the left hip). In some implementations, the control box 122 can be moved from a first suit (for example suit 110 and the associated signal pathway 2) to another suit. In this way, the first suit can be replaced with an identical (e.g., clean or new) suit 110, or replaced with a different suit having different electrodes, electrode locations, and/or a different suit having a different size, such as suit 50. For example, a wearer can use the control box 122 with multiple identical suits 110 worn on different days, or use the control box 122 with a first suit 110 that is later replaced with a second larger suit as the wearer gains muscle mass.

Operating Software

The control box 122, including at least stimulation controller 120, and smart suit 110, including at least electrodes 1, are operated via operating software 150. In some implementations, the software 150 is stored in the control box 122 and is programmed to perform a pre-set stimulation pattern via the stimulation controller 120 and electrodes 1. In many implementations, the operating software 150 is remote software 150 stored on a manager device 152. As mentioned above, in many implementations, the control box 122 is wirelessly connected to the manager device 152. In several implementations, the control box 122, and thereby the stimulation controller 120, is wirelessly connected via Bluetooth connection to the operating software 150. In several implementations, the software 150 is written to operate the stimulation controller 120 and the suit 110 with electrodes 1 with a manager device 152, such as a tablet/pad, laptop, desktop computer, cell phone, or other portable computing device. The manager device 152 may be configured to display a graphical user interface to facilitate user interaction via a touchscreen display or via commands using a user interface device (e.g., keyboard, mouse, trackpad, switches, buttons and/or the like). The software 150 provides the platform to deliver a more efficient muscle training and/or rehabilitation than traditional training and/or rehabilitation methods. In many implementations, the software 150 operates on both Apple and Android platforms, but it is not limited to them. The software 150 is designed to be easy to use, and allows the practitioner to have all of their clients' (wearers') information at their fingertips, capturing the training data to provide necessary information to monitor each client's progress.

The software 150 operates to control the stimulation delivered by the stimulation controller 120 and to manage the other components (such as data from sensors 7, 10 and feedback as discussed above) in control box 122 and provide data to the practitioner. In many implementations, the software 150 provides a HIPAA compliant telemedicine platform for communication with the practitioner, transmission of data, and interactive controls of the session. In some implementations, the software 150 includes artificial intelligence (AI) analysis of sensor data, for example, data from sensors 7, 10. In some implementations, AI analysis of sensor data is used to automatically adjust or suggest changes to the stimulation patterns or other session features. The sensor data may be gathered from multiple wearers of various demographics over time and used to train data sets that can be used to improve the AI analysis. For example, sweat sensor analysis e.g., from sweat sensor 7, can be used to deliver the optimal wave forms and frequency ranges of stimulation to the electrodes 1 in the suit 110 of an individual user. In some implementations, AI analysis of sensor data is used to identify pre-cursors of potential medical conditions. In some implementations, two-way communication between the software 150 and the control box(es) 120 is continuous, and sensor analysis is ongoing throughout a session. In some implementations, the software 150 creates (e.g., is programmed to create upon execution of stored instructions on a computer-readable storage medium) an electronic medical record. For example, an electronic medical record can be generated at the conclusion of a physical therapy session. In some implementations, a session record is sent to the client and/or practitioner. In some implementations, a session record is sent to a remote server. In some implementations, clients, practitioners, and other authorized individuals or groups can remotely access stored session records.

In some implementations, the system 100 operates as a wearable closed-loop cognitive and biophysical assessment and augmentation system for operation in controlled training environments and/or extreme operational environments and can provide real-time biophysical parametric measurement and physical and cognitive assessment and evaluation. The assessments can include analysis and detection of stress and fatigue, optionally powered by artificial intelligence (AI) algorithms. During training applications, the system 100 can communicate measurement and assessment data securely to simulators, learning management systems (LMSs), other session participants (for example, squadmates, teammates, training partners, and the like), and real or virtual instructors to improve training effectiveness. Data can be securely communicated to the electrodes 1 and/or feedback on the suit 110 (e.g., via the control box 122 and signal pathway(s) 2) to mitigate fatigue and stress, enhance operational performance, and/or help reduce fatigue- and stress-related mishaps.

Figure 20:
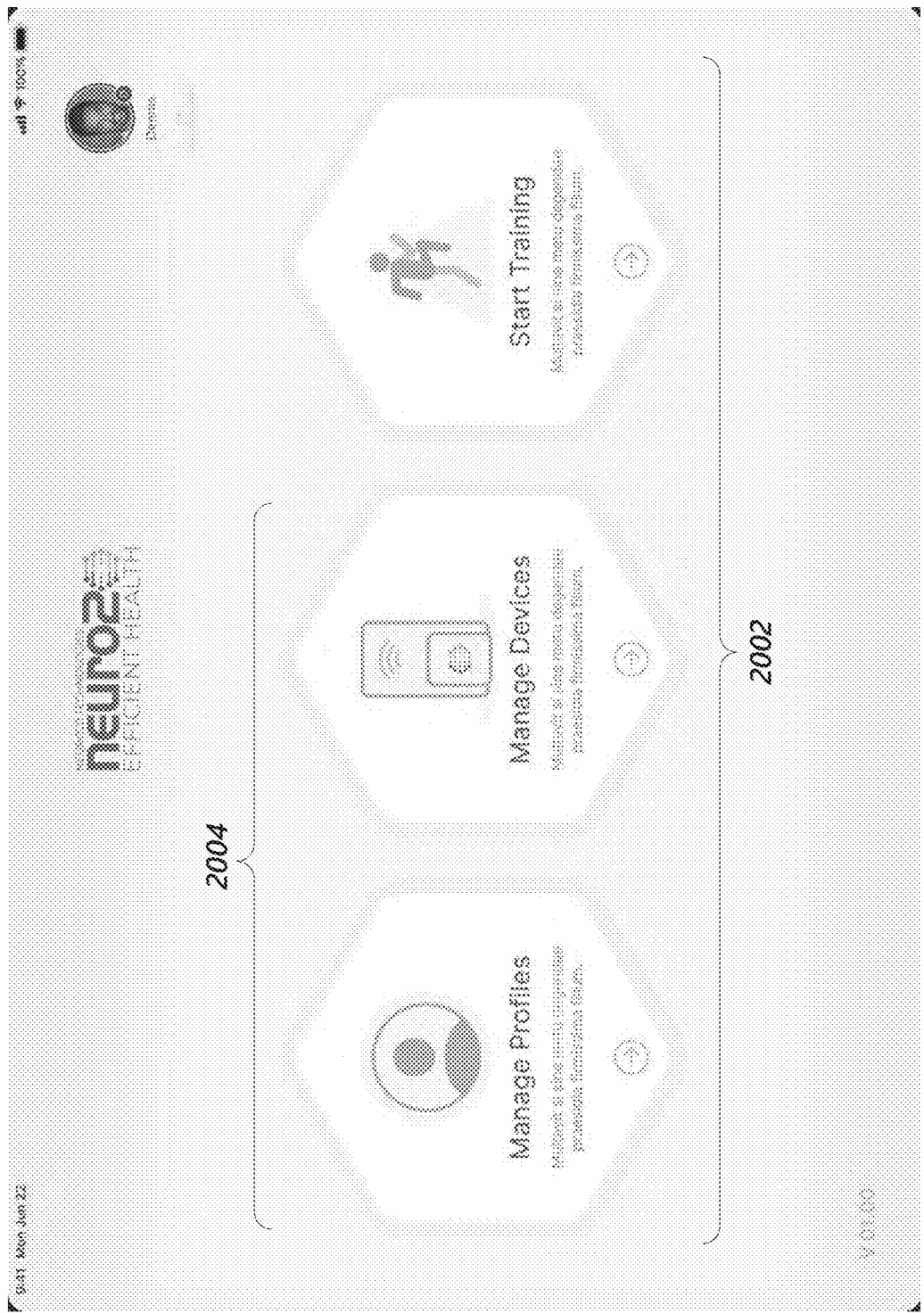

An example implementation of software 150 (e.g., software platform) is illustrated in FIGS. 20-38. After a user successfully logs into the system, options 2002 are presented according to the type of account, as shown in FIG. 20. For example, a practitioner (e.g., manager, trainer, clinician, etc.) account can include access to all options 2002, including management of profiles and devices, as well as initiating training sessions. A client account (for a wearer of the suit) can allow access to a limited set of options that exclude practitioner-only options 2004. Other account types, for example very limited demonstration accounts or technical support administrative accounts, can be shown an appropriate scope of options.

Figure 21:
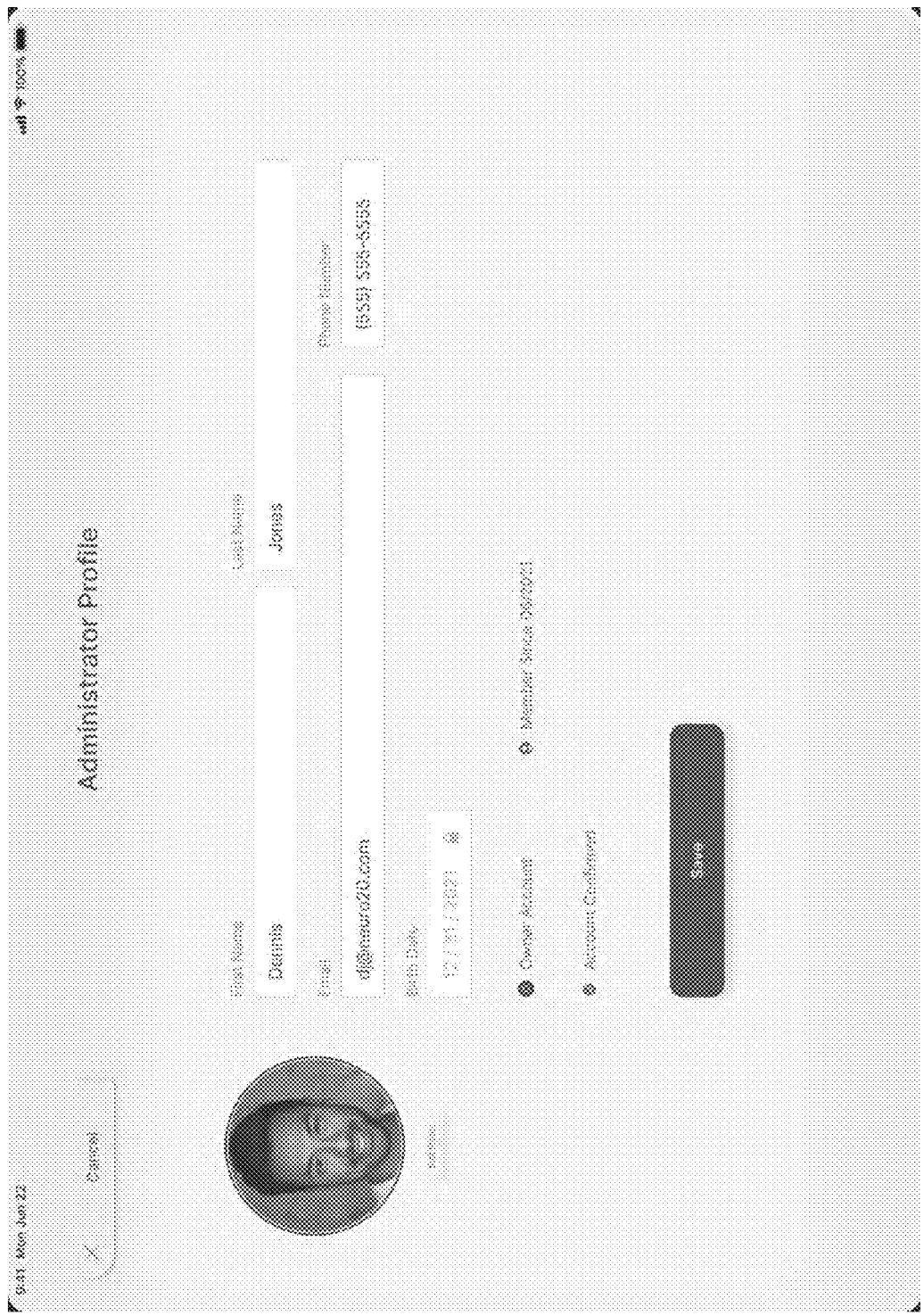
FIG. 21 illustrates an implementation of the platform software practitioner profile.
Figure 22A:
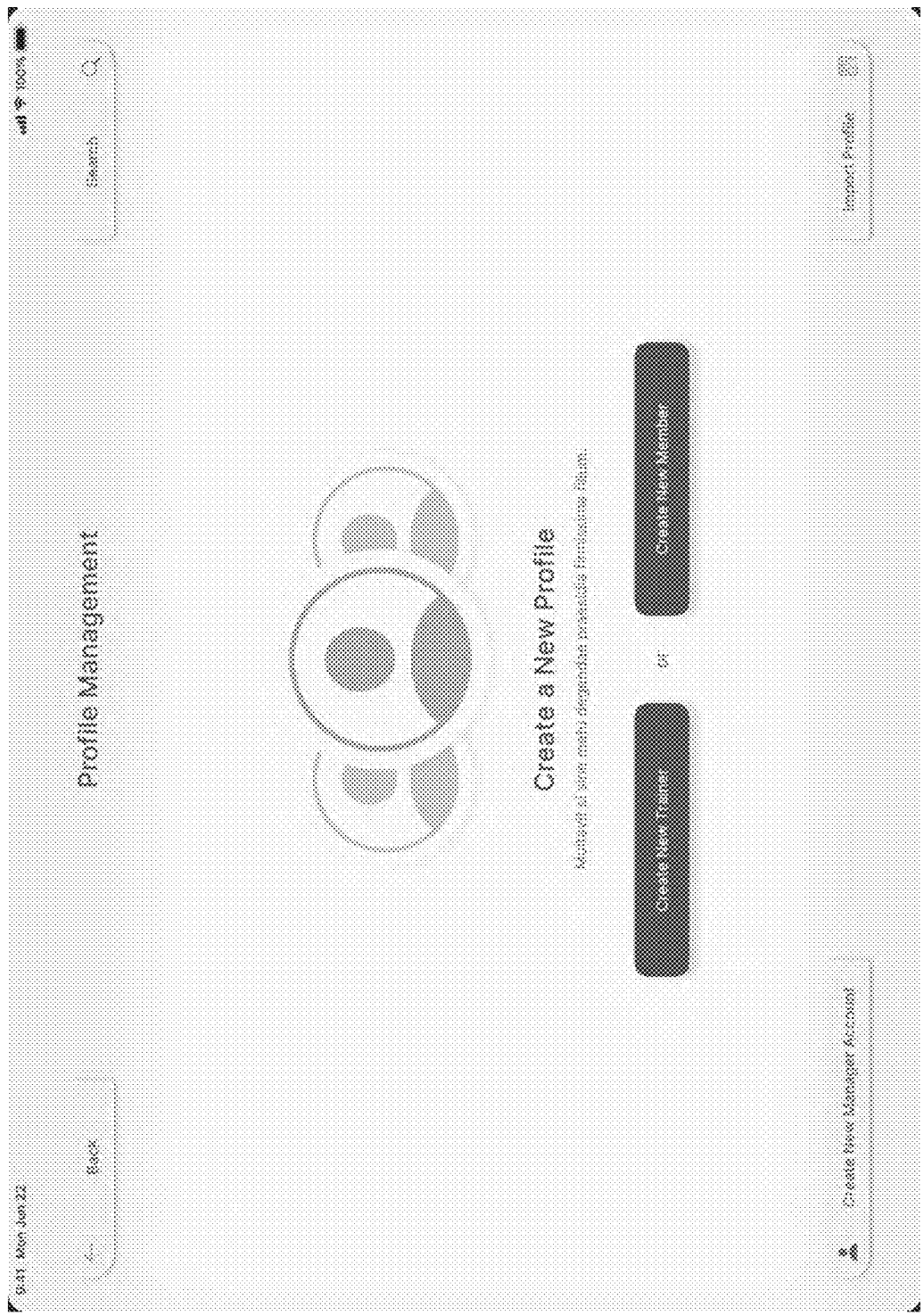
FIGS. 22A and 22B illustrate an implementation of the platform software new profile entry function.
Figure 22B:
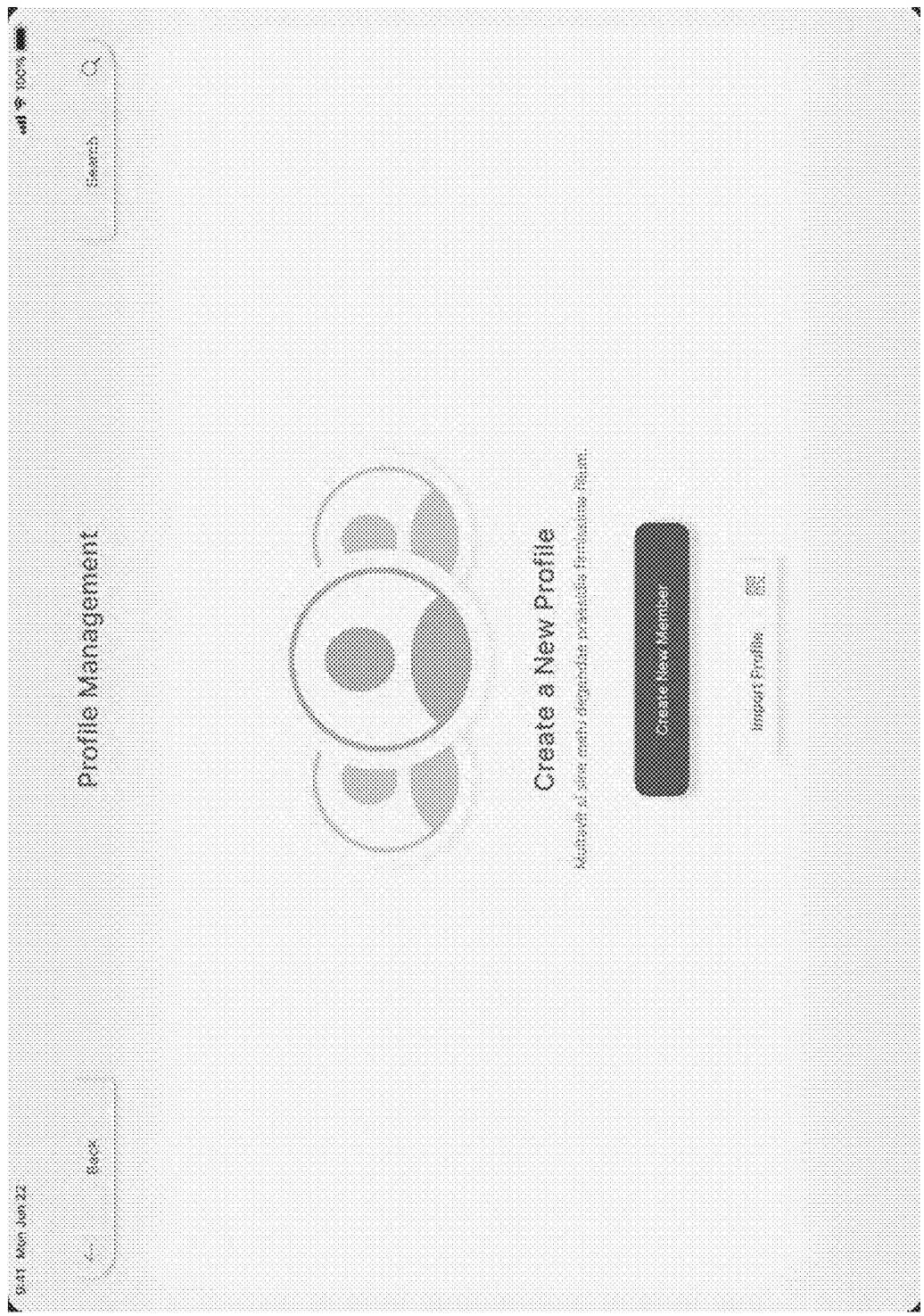

Users who have successfully logged in can also access and update their profiles, as shown in FIG. 21. This feature can allow a user to change preferred contact information, payment methods, profile photos, licenses, certifications, credentials, and other information. A practitioner account or other account with appropriate permissions can also create new accounts, particularly new client accounts, as shown in FIGS. 22A-B. New user information can be entered directly, scanned into the system (for example via bar code, QR code or other machine-readable or optical code), or imported after being created and saved elsewhere (for example, via weblink or email invitation, personnel or membership databases, kiosk registration, etc.). As shown in FIG. 22A, users with high level permissions can create additional manager accounts, trainer or practitioner accounts, and member or client accounts. As shown in FIG. 22B, users with insufficient permissions or users that are not successfully logged into the system can only create new client or member accounts.

Figure 23:
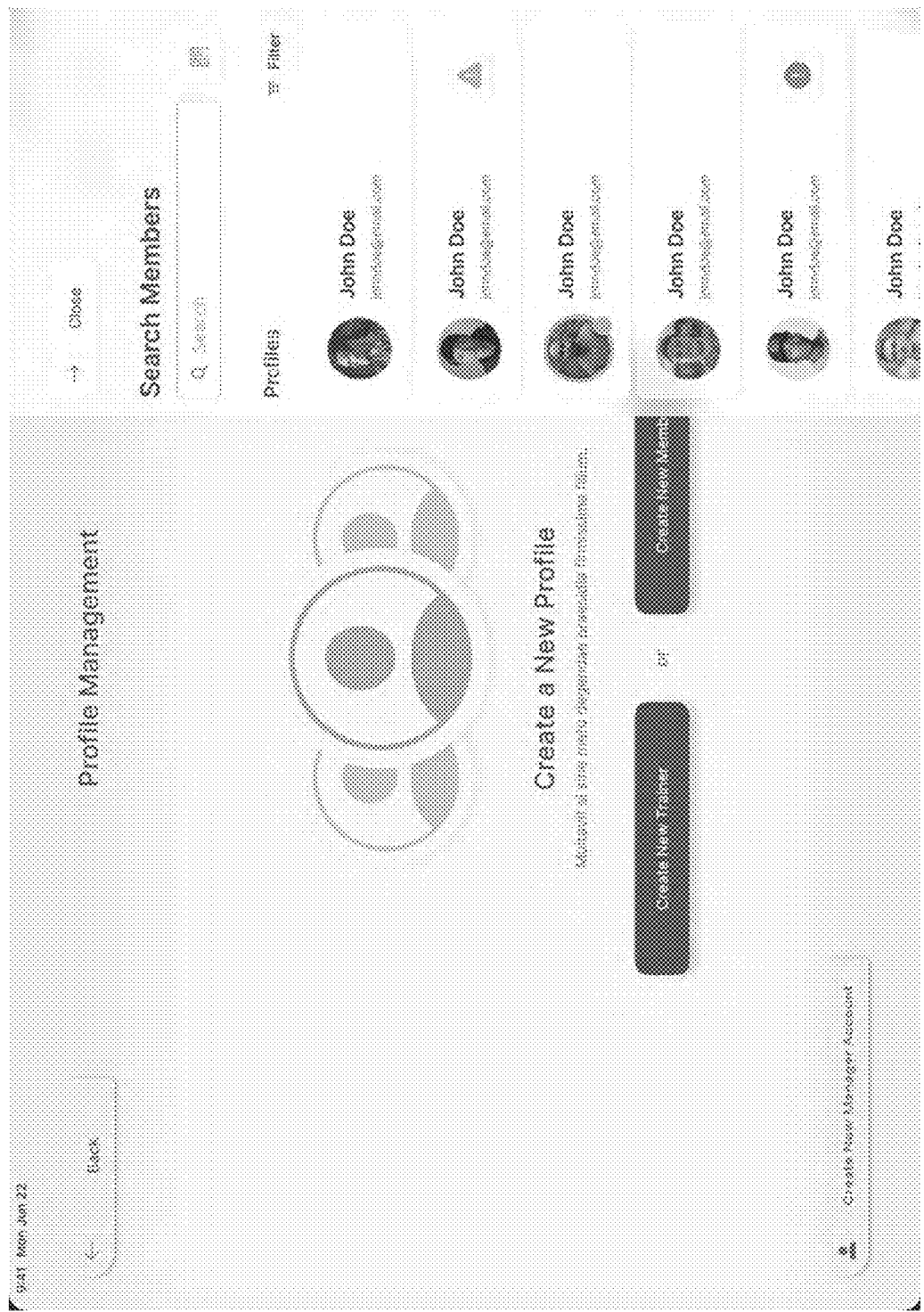
FIG. 23 illustrates an implementation of the platform software profile search.

As shown in FIG. 23, the system allows searching of member accounts. In some implementations, incomplete accounts can be searched and finalized. In some implementations, authorized users are able to monitor, update, or otherwise manage accounts. For example, individual client members can manage their own accounts, while practitioner members can manage all accounts or a subset of accounts. For example, in some implementations, a practitioner member may be authorized to manage all member accounts, while in other implementations or for other authorization levels, the practitioner member may have access only to client accounts associated with a particular facility (e.g., a gym, rehabilitation center, athletic facility, simulation facility, virtual reality environment, etc.) or his/her own clients.

Figure 24A:
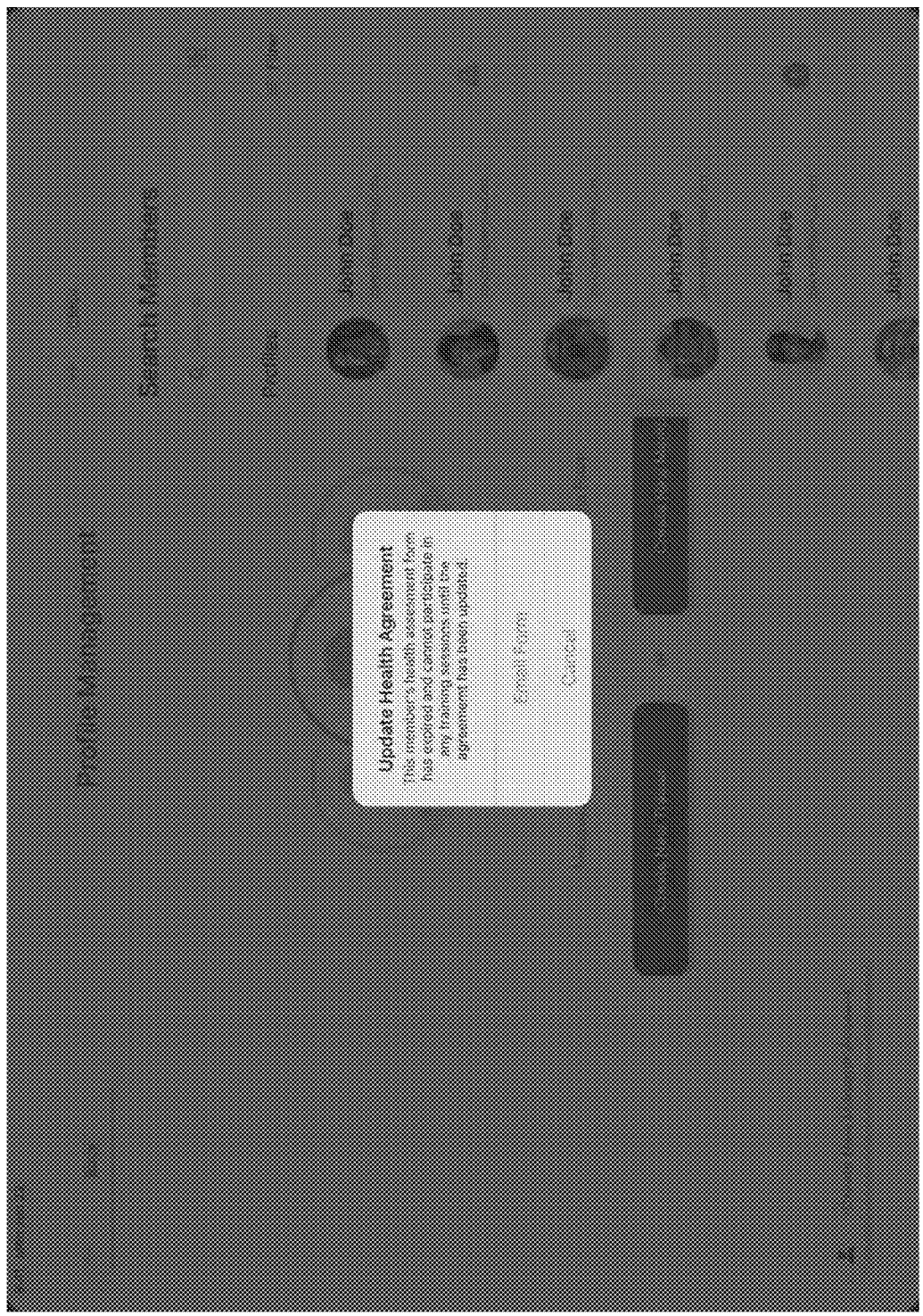
FIGS. 24A and 24B illustrate an implementation of the platform software check for a current health agreement.
Figure 24B:
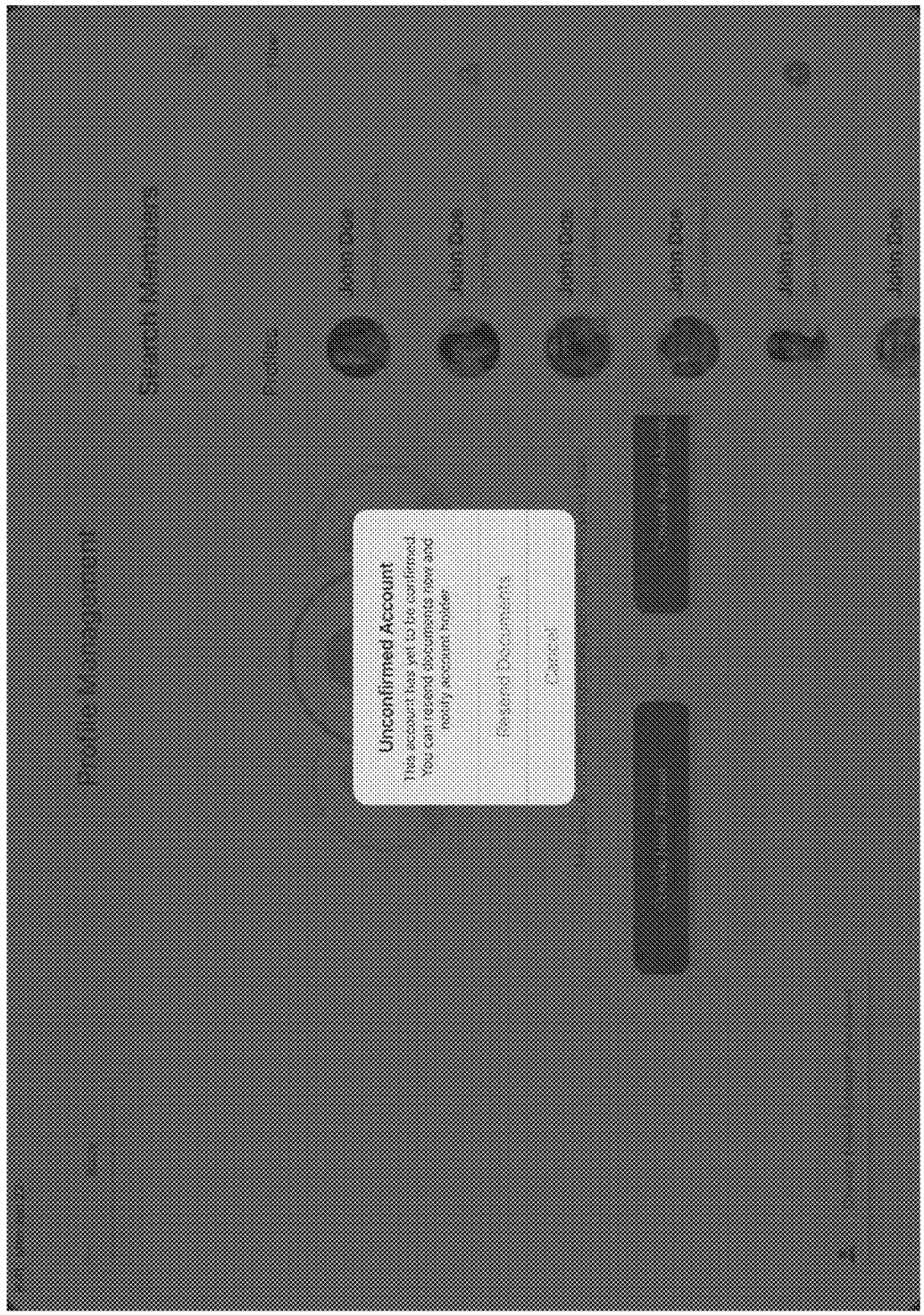

In some implementations, a health agreement is required to finalize an account, such as before a client member can use the wearable system. In some implementations, the health agreement may ask a client member to verify a particular injury and/or diagnosis, confirm clinician and/or insurance details, certify that he/she is in good health or otherwise able to participate, acknowledge privacy notices, and/or other administrative and health related forms and information. As shown in FIG. 24A, the software 150 can verify and request missing information automatically. As illustrated in FIG. 24B, the software 150 can optionally provide (display, email, text message, etc.) any missing agreements and/or flag any missing information, such as missing contact information. In some implementations, users are required to periodically update or re-confirm an existing health agreement.

Figure 25A:
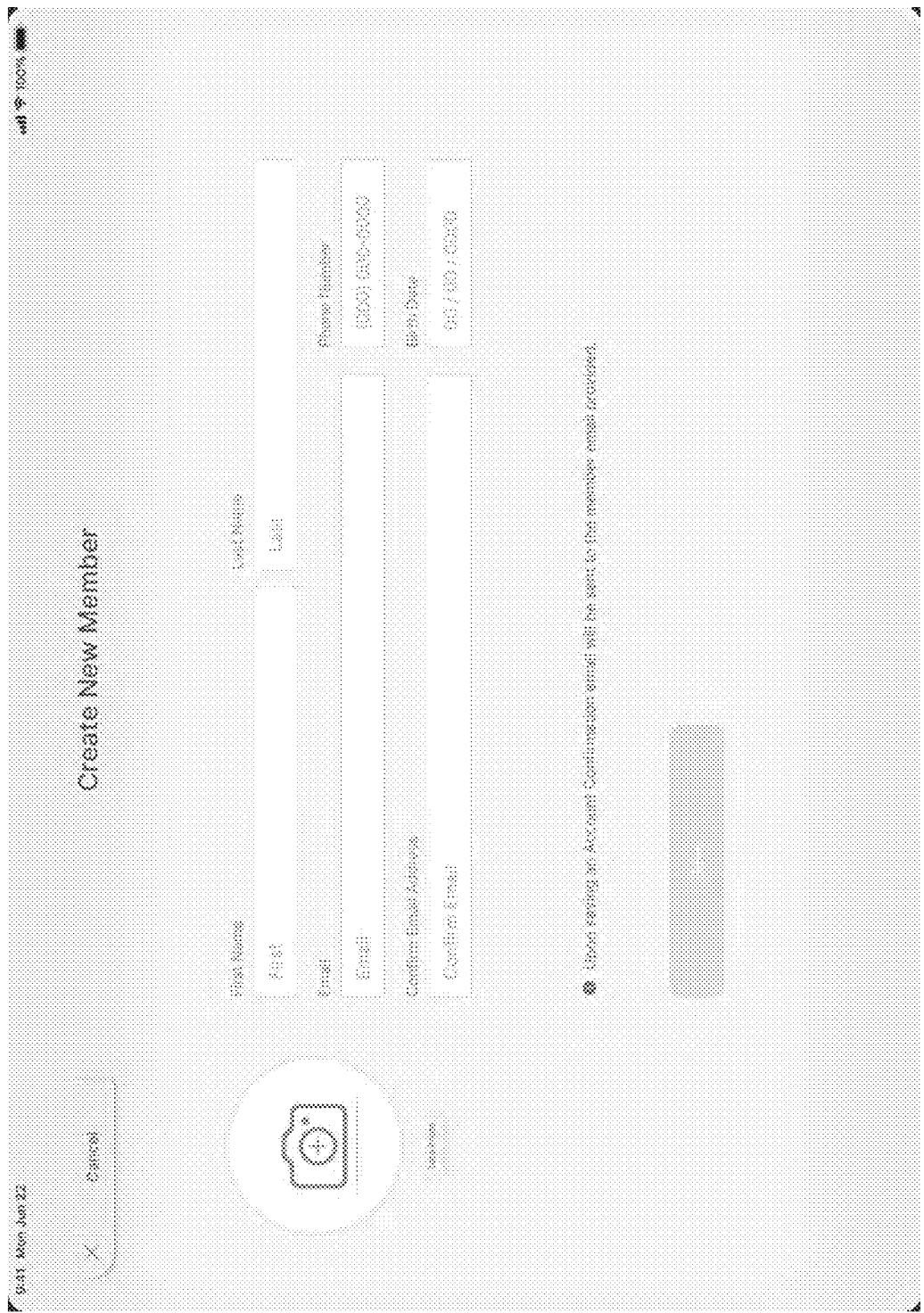
FIGS. 25A and 25B illustrate an implementation of the platform software function to create and confirm a new user.
Figure 25B:
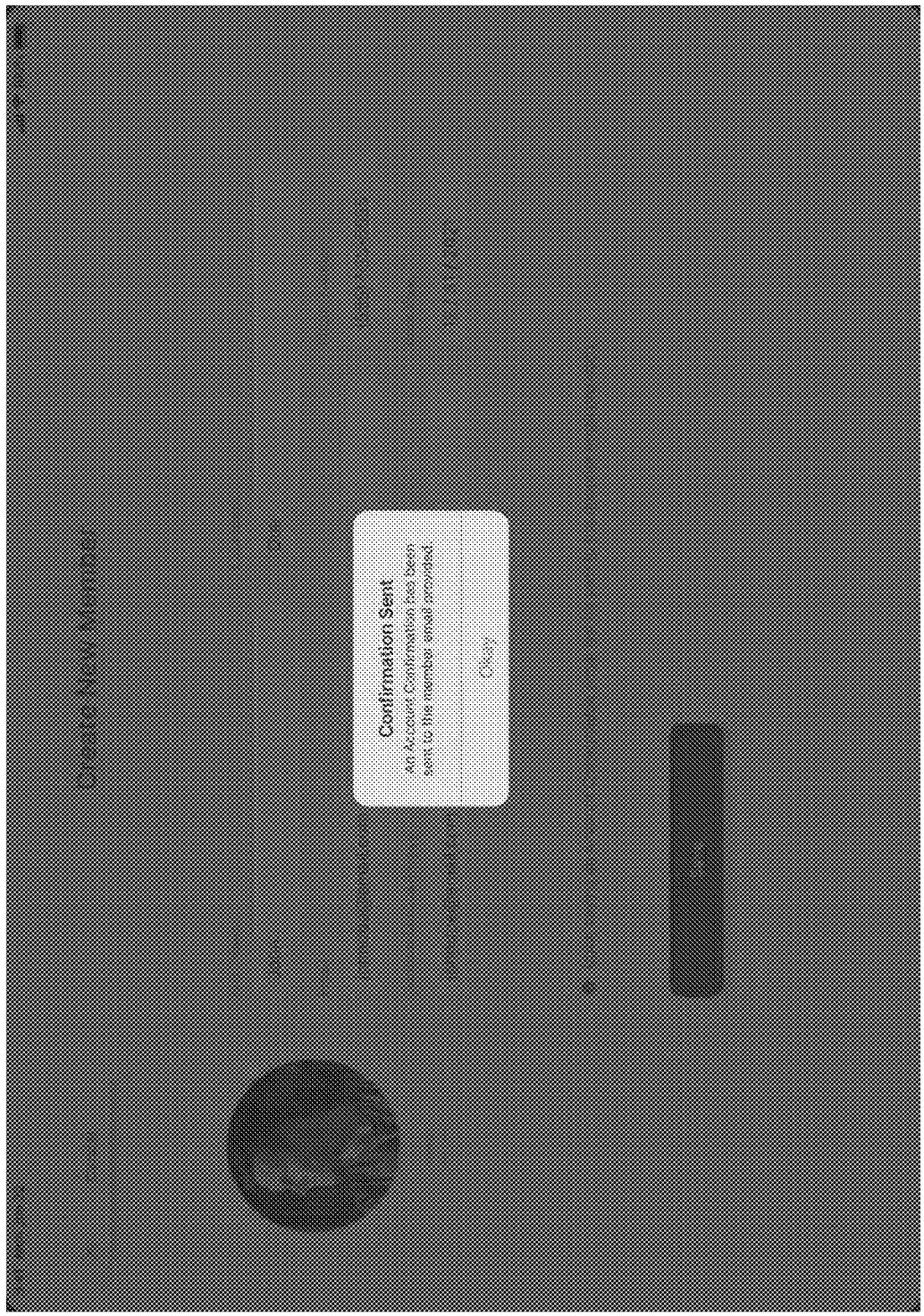
Figure 26:
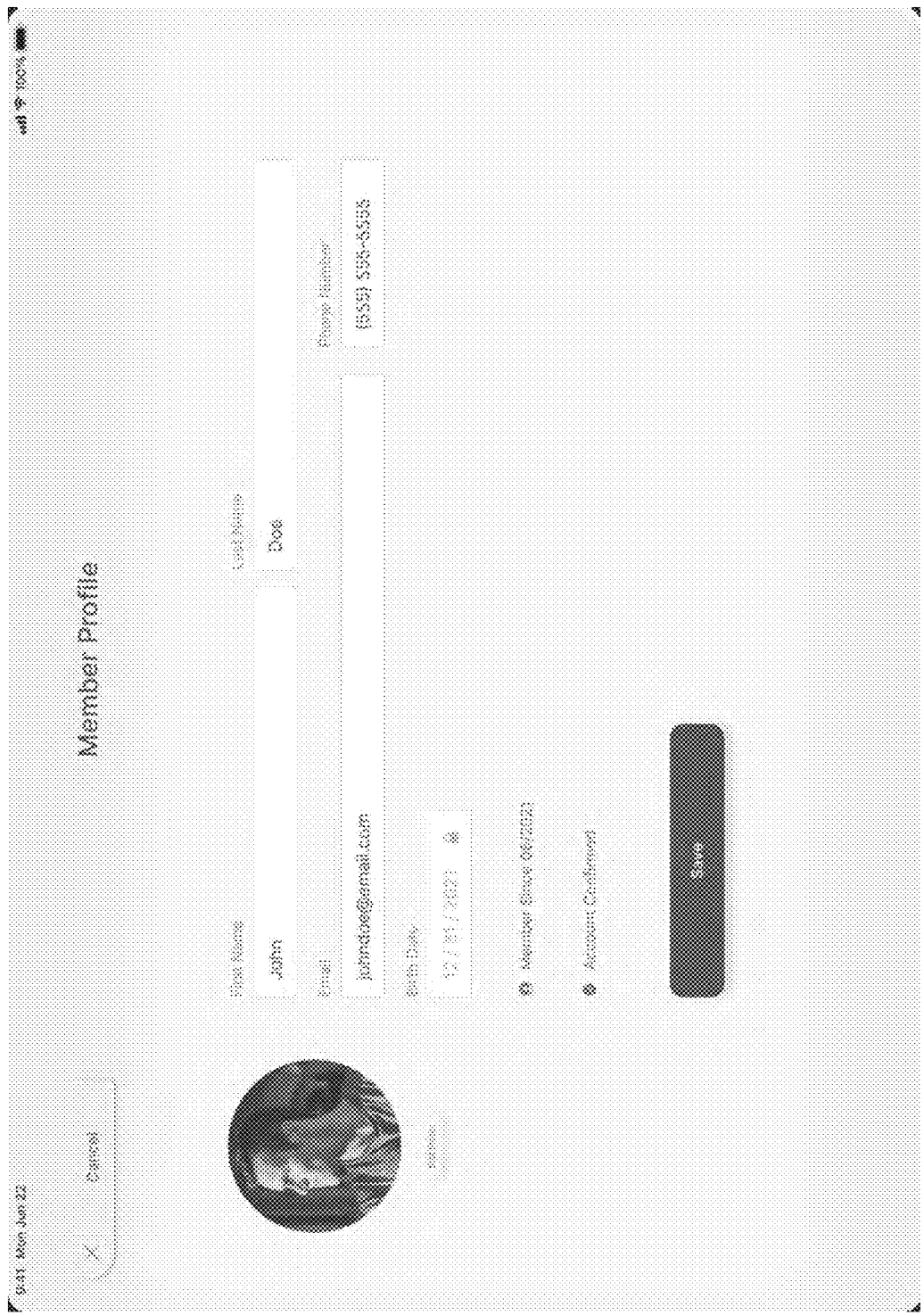
FIG. 26 illustrates an implementation of the platform software successful confirmation of a new user.

Returning to FIGS. 22A-B, new member accounts can be created by entering profile details, as shown in FIG. 25A and completing all necessary health agreements as discussed above. FIG. 25B illustrates a finalized account confirmation screen, which indicates that an account was successfully created and confirms contact information. FIG. 26 illustrates one implementation of a confirmed or active member account profile.

Figure 27:
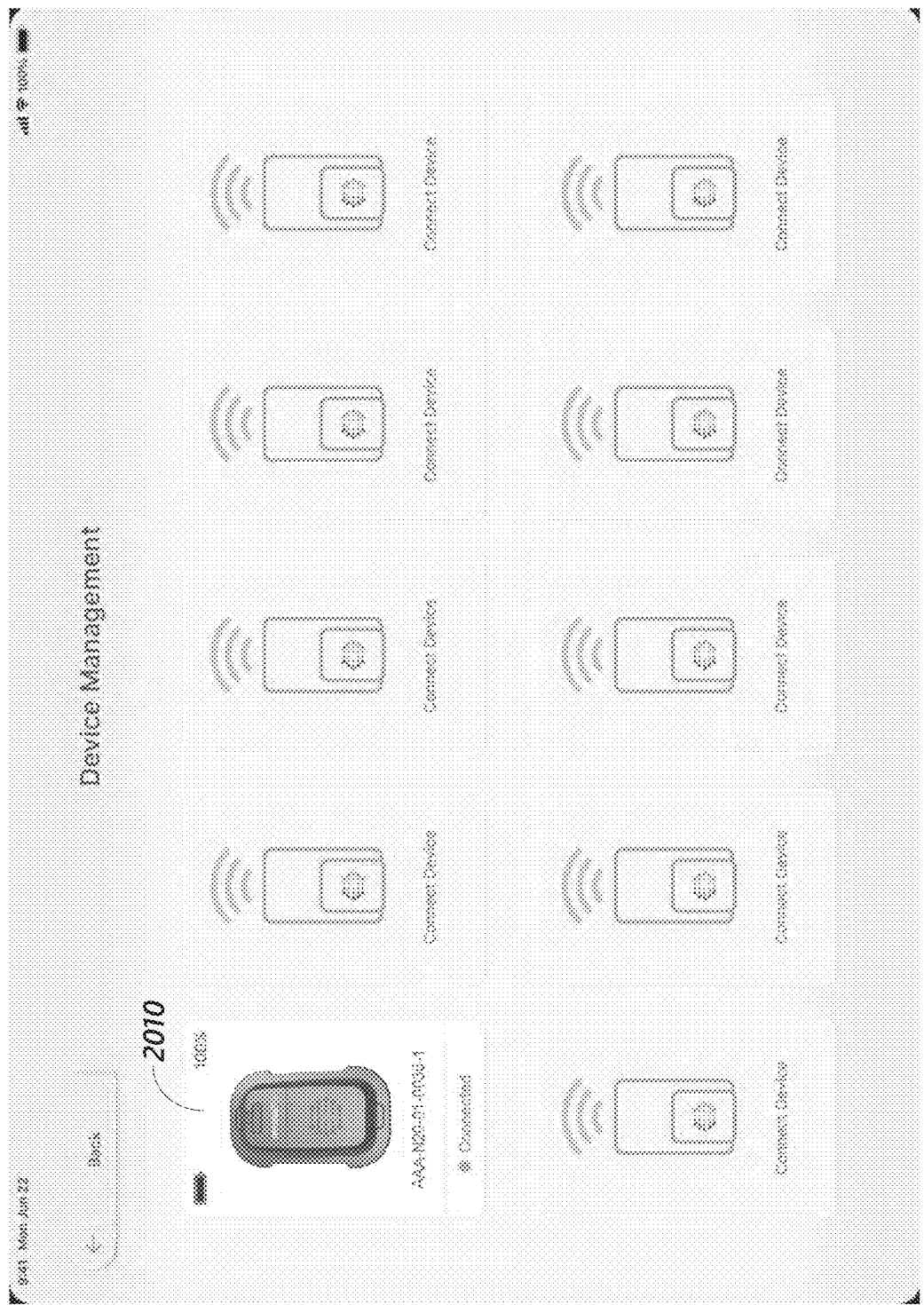
FIG. 27 illustrates an implementation of the platform software practitioner screen to add devices.
Figure 28:
FIG. 28 illustrates an implementation of the platform software practitioner display of all devices added to a session.
Figure 29A:
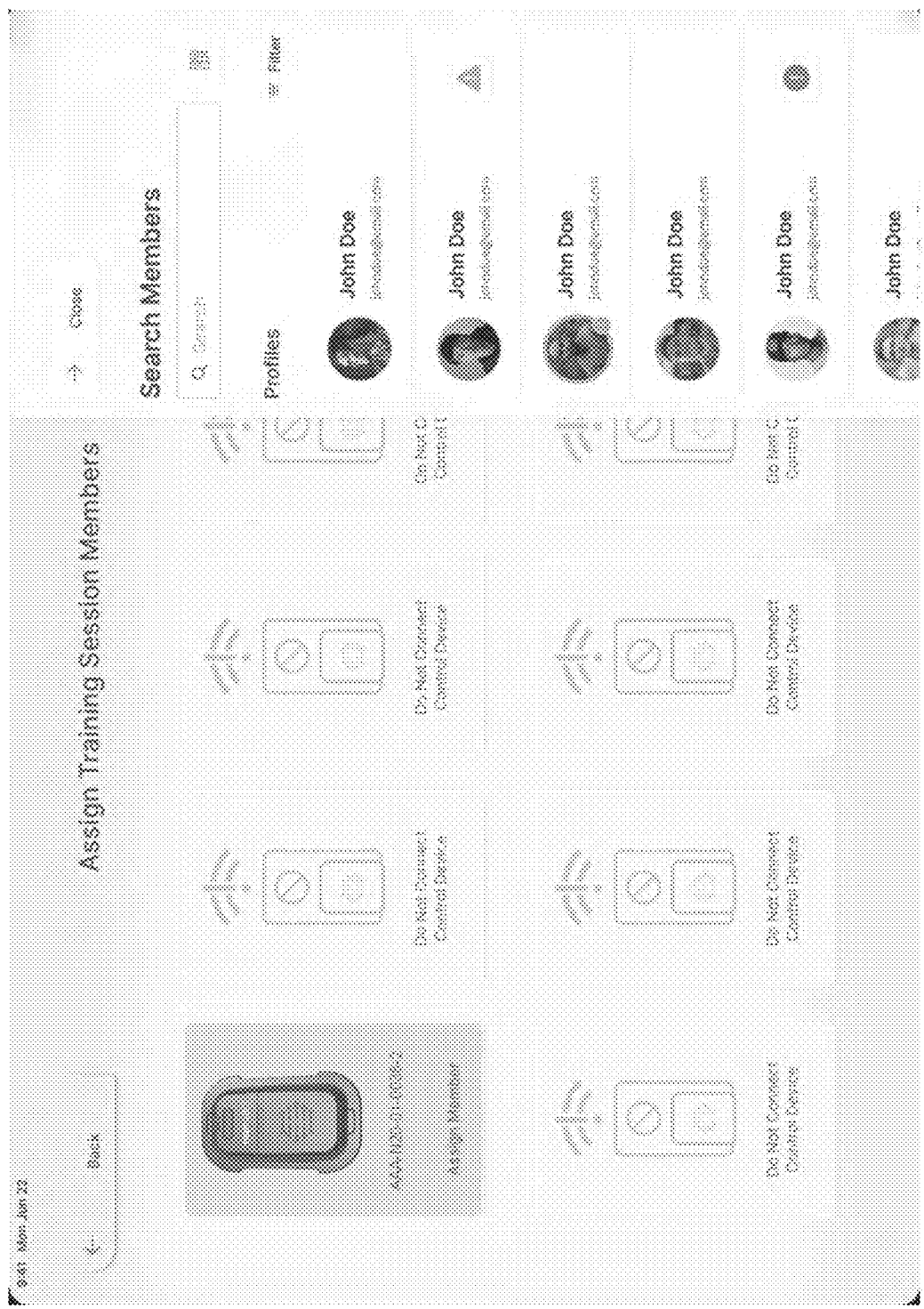
FIGS. 29A and 29B illustrate an implementation of the platform software practitioner display of added devices assigned to clients.
Figure 29B:
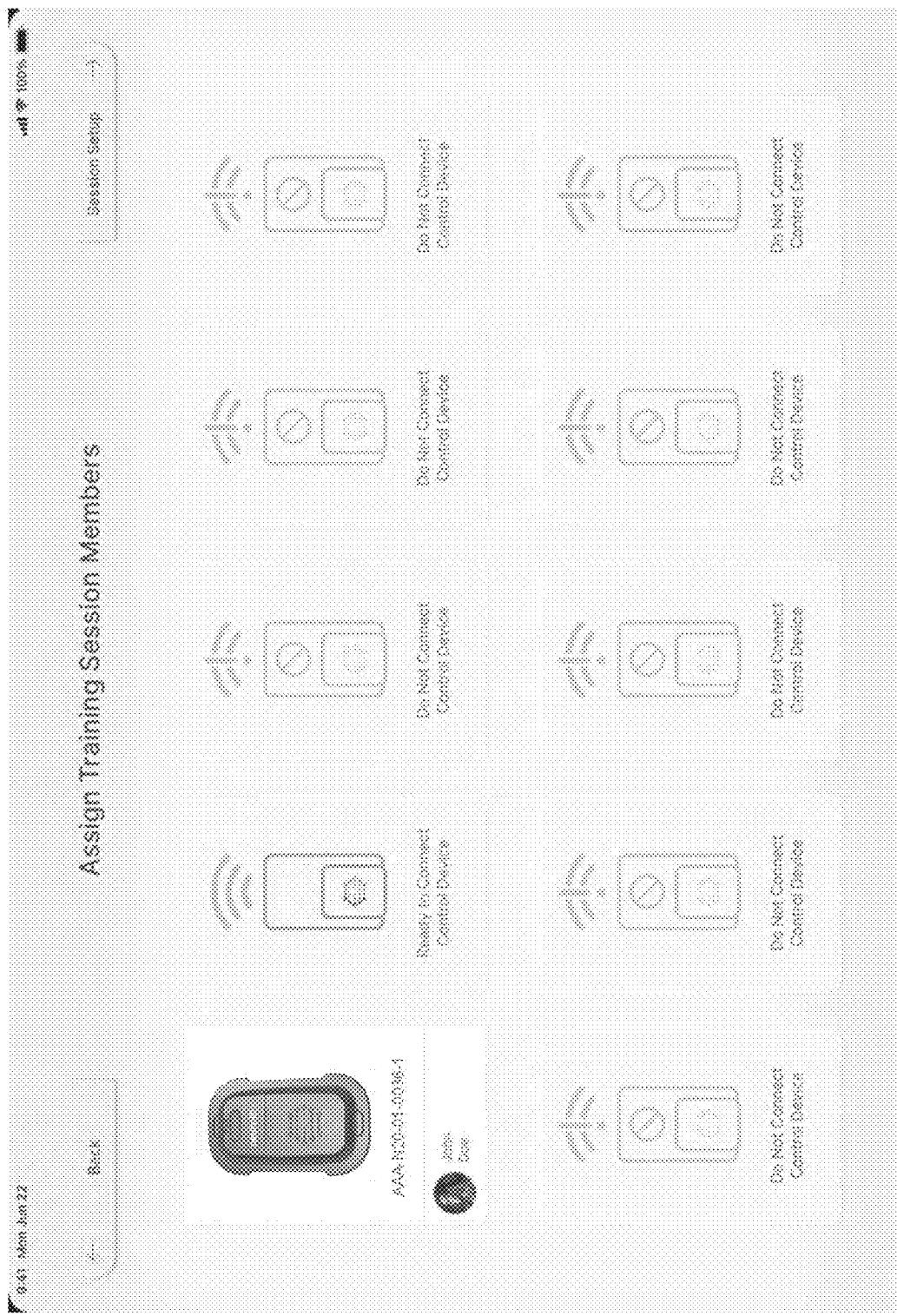
Figure 30:
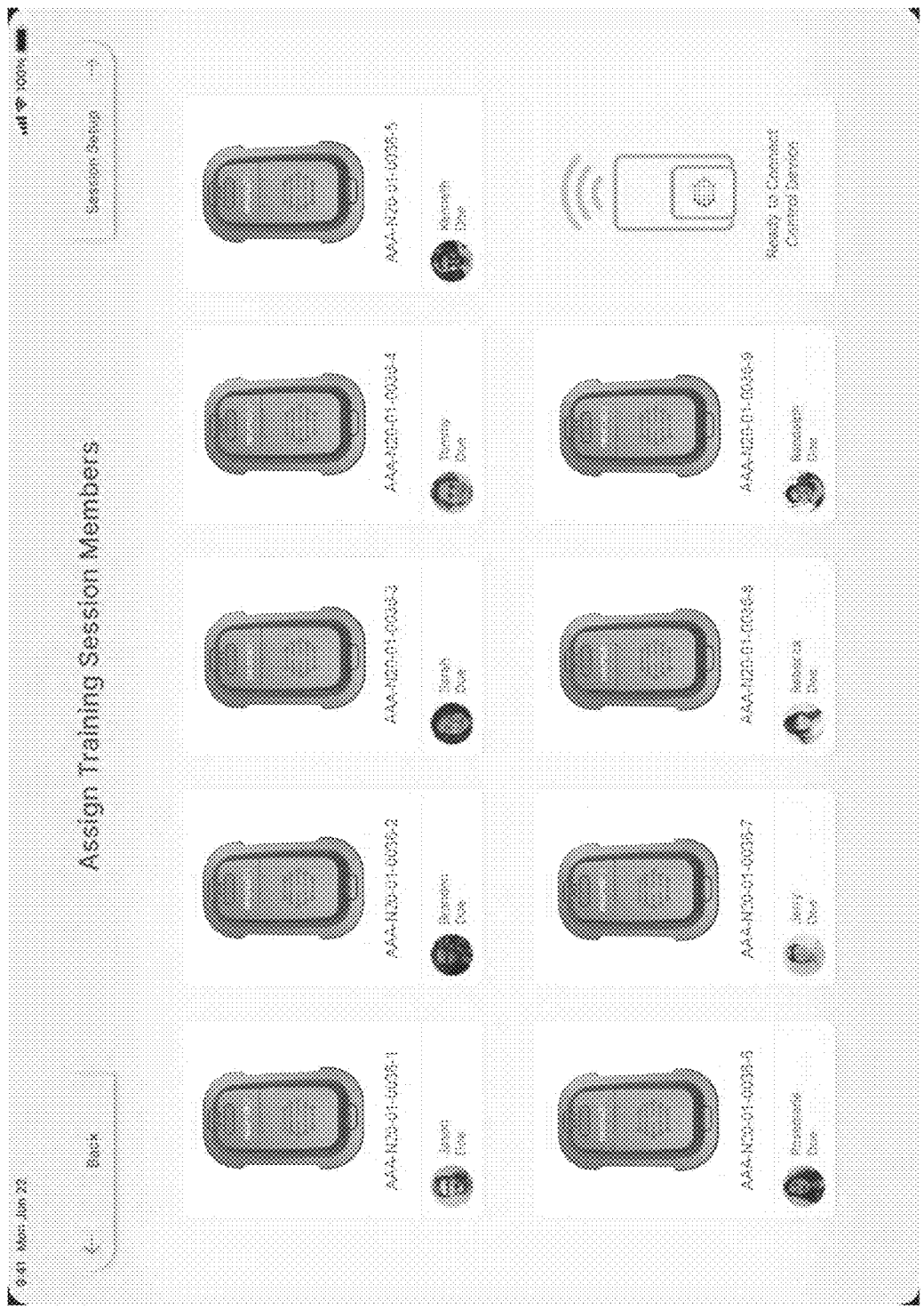
FIG. 30 illustrates an implementation of the platform software practitioner display of all devices added to a session and assigned to clients.
Figure 31:
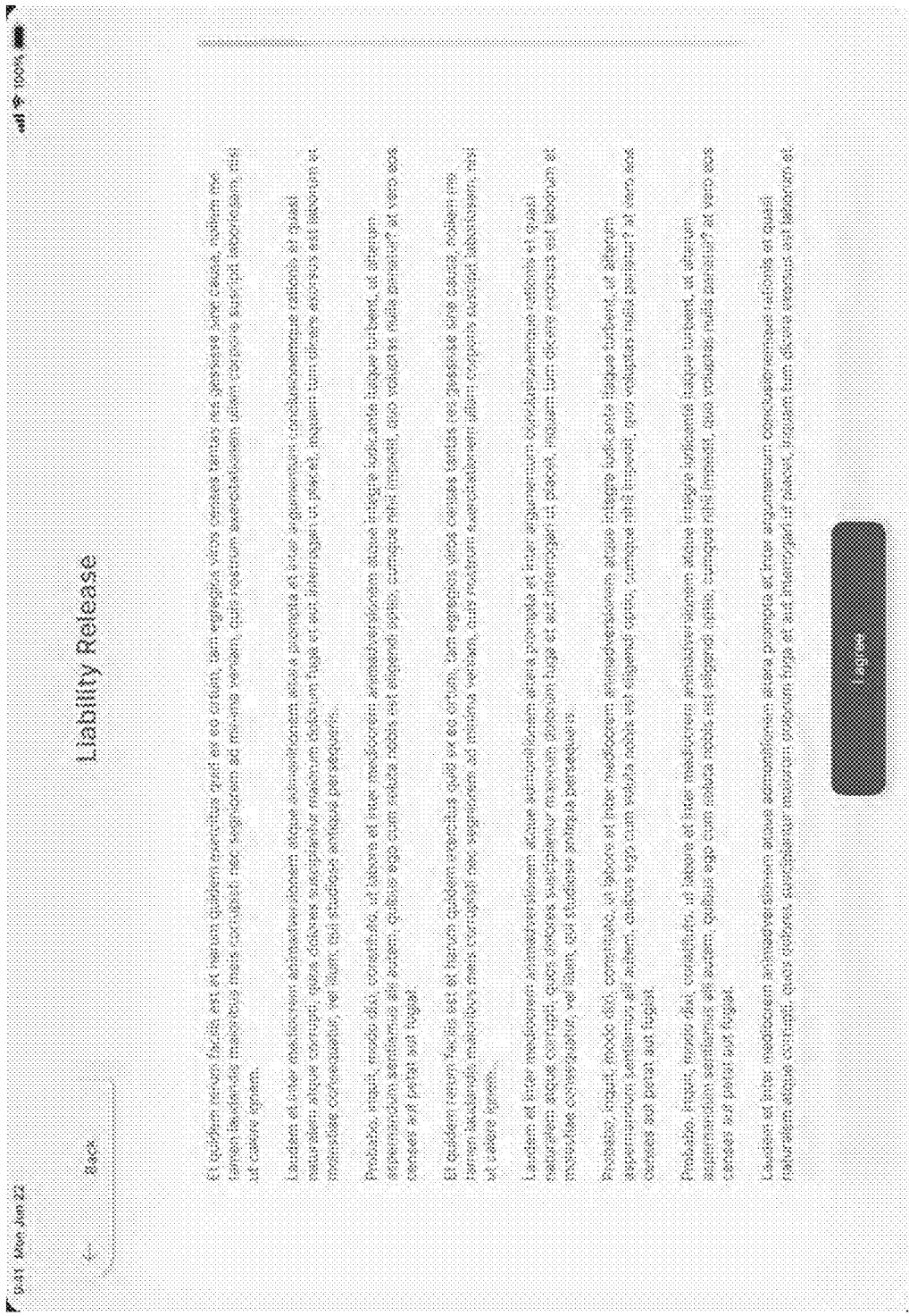
FIG. 31 illustrates an implementation of the platform software waiver verification.

FIG. 27 shows an implementation of a practitioner account at the start of a training session. The practitioner adds simulation control boxes 2010 to the session. In this implementation, the practitioner is authorized to provide training to ten clients. In other implementations, or for other users with different authorization levels, the number of clients and stimulation boxes can vary. For example, in some implementations such as a single-user home system, only one stimulation box can be added to the session. As shown in FIG. 28, the practitioner of FIG. 27 has added all stimulation boxes (e.g., control boxes 120) for the session. Each stimulation box includes a status indicator, for example status 2016, to notify the practitioner of the status. For example, each stimulation box can be marked as connected, disconnected, low battery, outdated, or other information. Details 2014 of each stimulation box can also be provided. After all the stimulation boxes are added to the session, they are paired to a client. The practitioner can select a client as shown in FIG. 29A to pair the client and the stimulation box as shown in FIG. 29B, until all clients and stimulation boxes are assigned, as shown in FIG. 30. Any additional reminders, warnings, notifications, waivers, or other important communications are presented to the member before stimulation can begin. For example, the practitioner is shown a final liability release in FIG. 31, which must be accepted before continuing.

Figure 32:
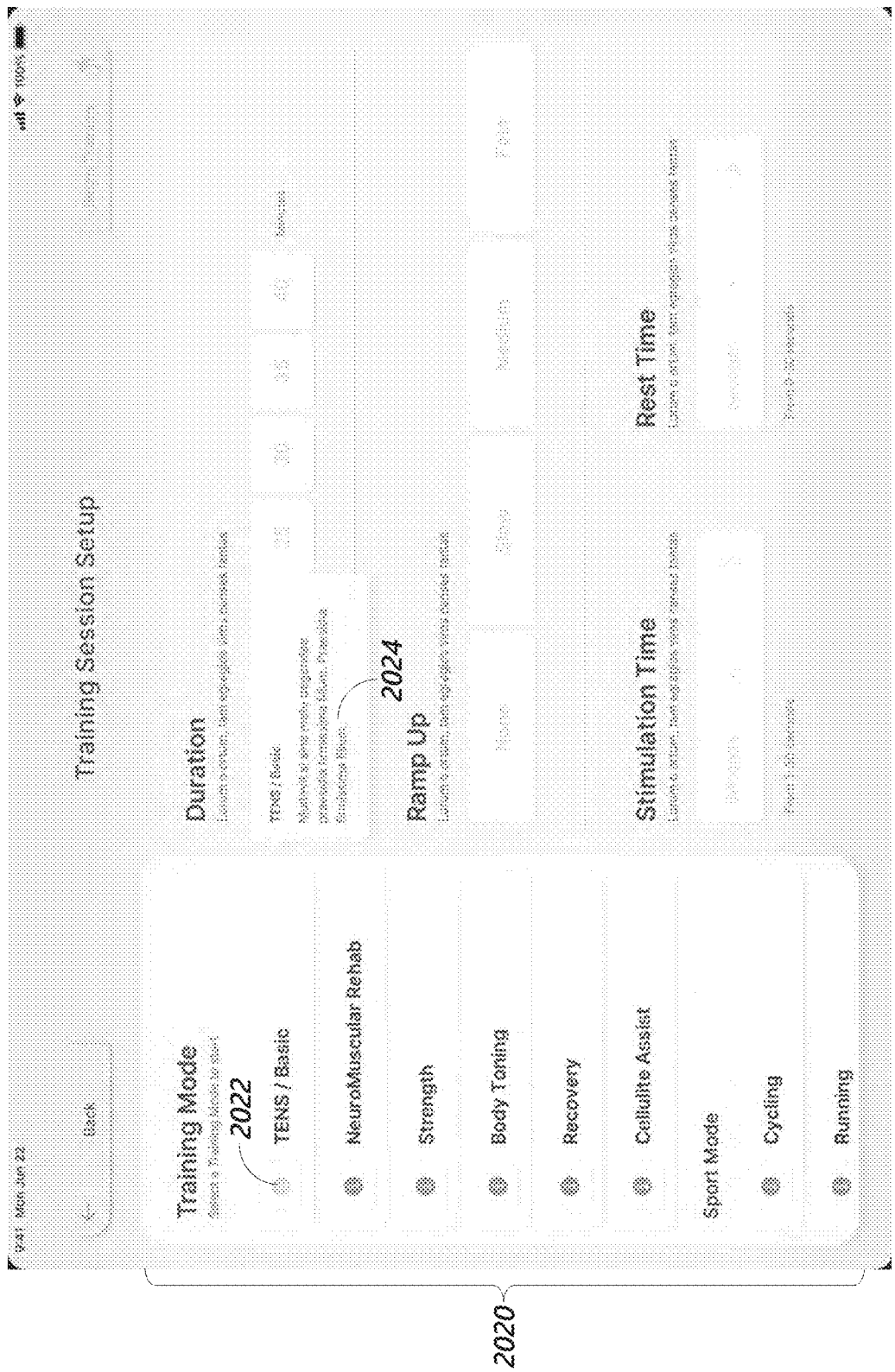
FIG. 32 illustrates an implementation of the platform software program information popup.

As illustrated in FIG. 32, in some implementations, the practitioner screen presents various stimulation modes 2020. In some implementations, the software automatically presents authorized programs for the member. For example, as shown in FIG. 32, the stimulation modes 2020 include a transcutaneous electrical nerve stimulation (TENS) mode and a neuromuscular rehabilitation mode, among other programs. In this implementation, a home-use client would not be presented with these more clinical modes. Alternatively or additionally, inaccessible modes may be presented but marked as unavailable. In other implementations, the mode may be available to all users, but the stimulation paradigm may be different depending on the user and the user's authorization level. For example, all users may be presented with and have access to a "strength" mode, but a home-use client user may have a different set of options, features, and/or limitations than a practitioner user who is fully trained. In some implementations, an information button or icon 2022 is available for some or each of the modes. This feature can optionally be used to provide additional information 2024 about the mode in order to assist a user in selecting the most appropriate program.

Figure 33:
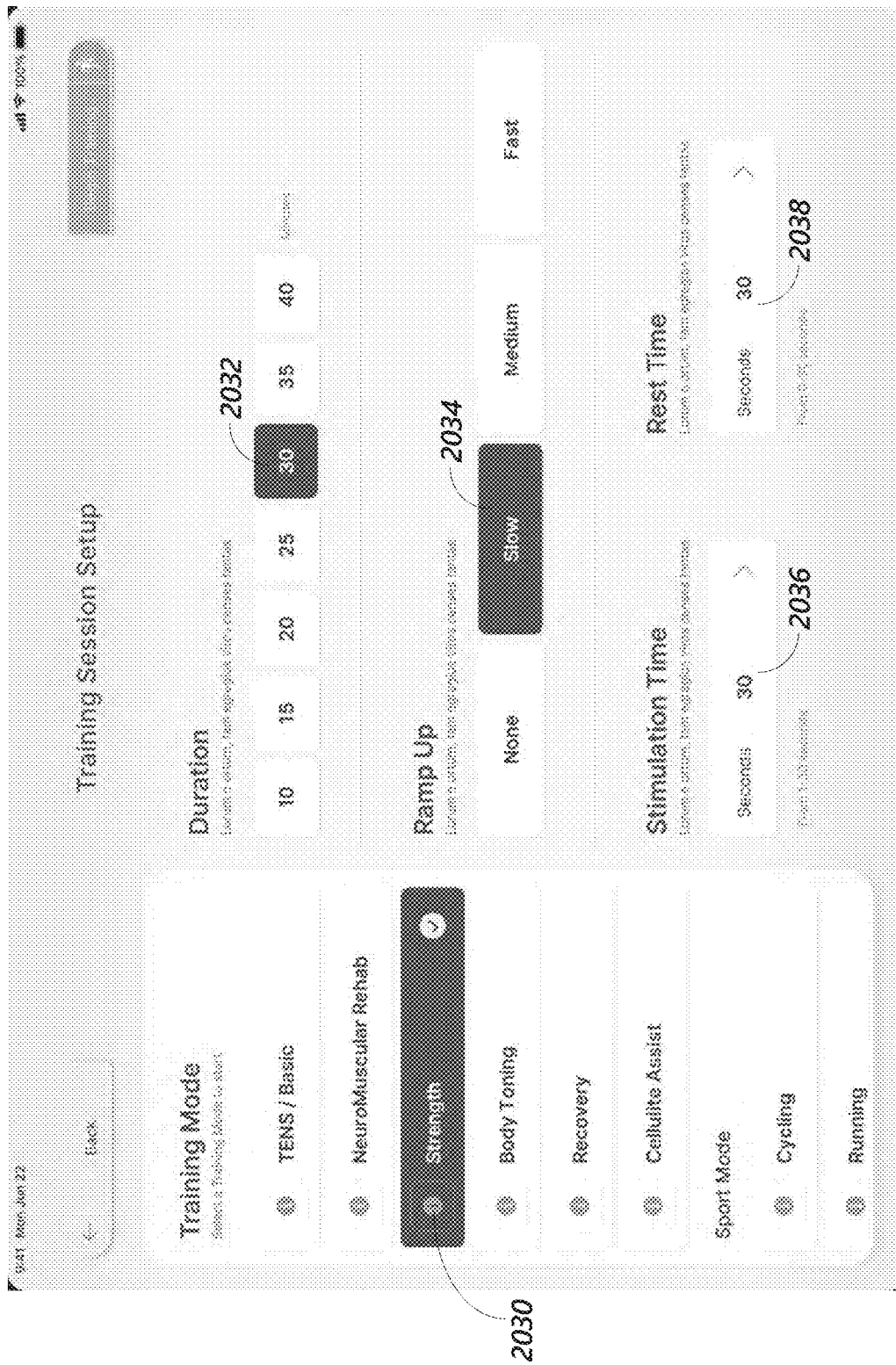
FIG. 33 illustrates an implementation of the platform software practitioner display of available programs and parameters.

With continued reference to the example implementations of the software 150, FIG. 33 illustrates a preliminary setup for a mode. The software 150 displays on a graphical user interface the selected mode 2030, the overall session length 2032, a ramp up rate 2035, a stimulation time or stimulation duration 2036, and an intervening rest time 2038. In this example, the options, such as duration option 2032 and ramp up option 2034 are selectable from a list of options. In other implementations, the user may be free to enter a desired time within an acceptable range. In other implementations, the option may be automatically pre-selected. For a practitioner user, each client in the session may have an individual settings package in some implementations. In other implementations, all clients in the session use the same settings package determined by the practitioner for the session.

Figure 34A:
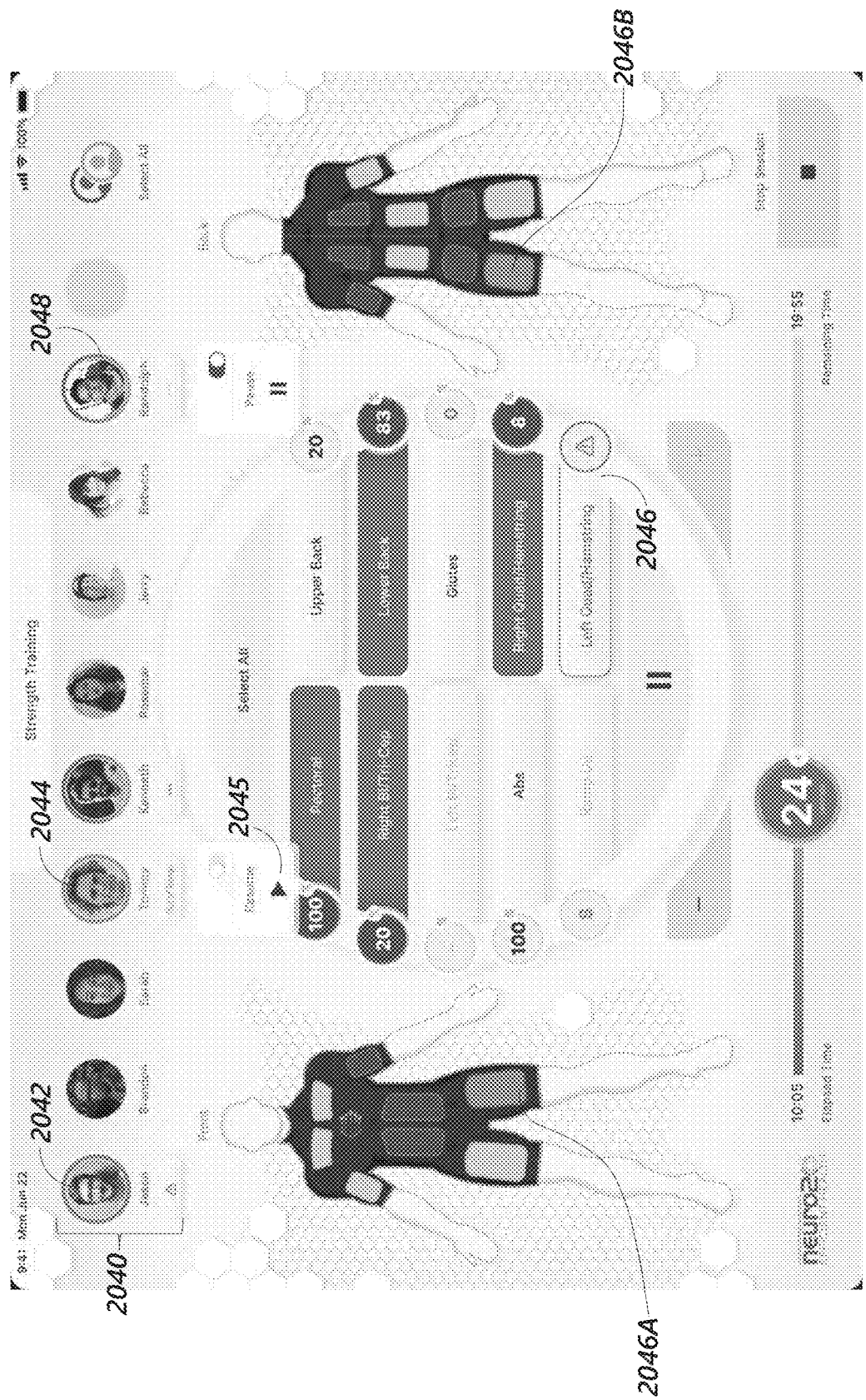
FIGS. 34A and 34B illustrate an implementation of the platform software practitioner session setup and session start.

An example implementation of a session screen is shown in FIG. 34A. After the preliminary setup is complete, the system displays on a graphical user interface the session participant users (clients) 2040, including individual users 2042, 2044, and 2048. The software 150 can display an individual user's status and various alerts. For example, as illustrated in FIG. 34A, a first user 2042 shows an alert to the practitioner. This alert 2046 indicates that the user 2042 requires attention to the left leg, where quadriceps electrode 1046A and hamstring electrode 2046B are not functioning as intended. For example, the alerting electrode(s) may be improperly connected to the skin, disconnected from the suit 110 or stimulation controller 120, damaged, etc. Other alerts include notification that a user is disconnected, such as user 2044 who is out of wireless range. In some implementations, stimulation is automatically re-started when the user 2044 returns to wireless range. In other implementations, the system provides an alert when the user 2044 returns to wireless range and requires the practitioner to re-start stimulation. Stimulation can be restarted in the software 150, for example via button 2045, or in hardware, for example by pressing a button on the control box 122 of the user.

The alerts and notifications can also include an indication that a user is not participating, such as user 2048 who is paused from receiving stimulation. In some implementations, a paused or out-of-range user, such as users 2048 and 2044, continue to receive stimulation. For example, the controller 120 can include a stored or pre-programmed stimulus paradigm or buffer. In some implementations, stimulation is stopped. In some implementations, sensor data is collected and stored and/or transmitted when a user is out of range or paused. In some implementations, sensor data collection is stopped. In some implementations, stimulation and/or sensing is stopped for the individual user. In some implementations, stimulation and/or sensing is stopped for all session participants. In still other implementations, starting, stopping, continuing and/or resuming stimulation and/or sensing for each session participant is set based on the type of error. For example, in the case of emergency, stimulation and sensing can be stopped for all session participants while only stimulation is stopped for a single user who steps away from the session.

Figure 34B:
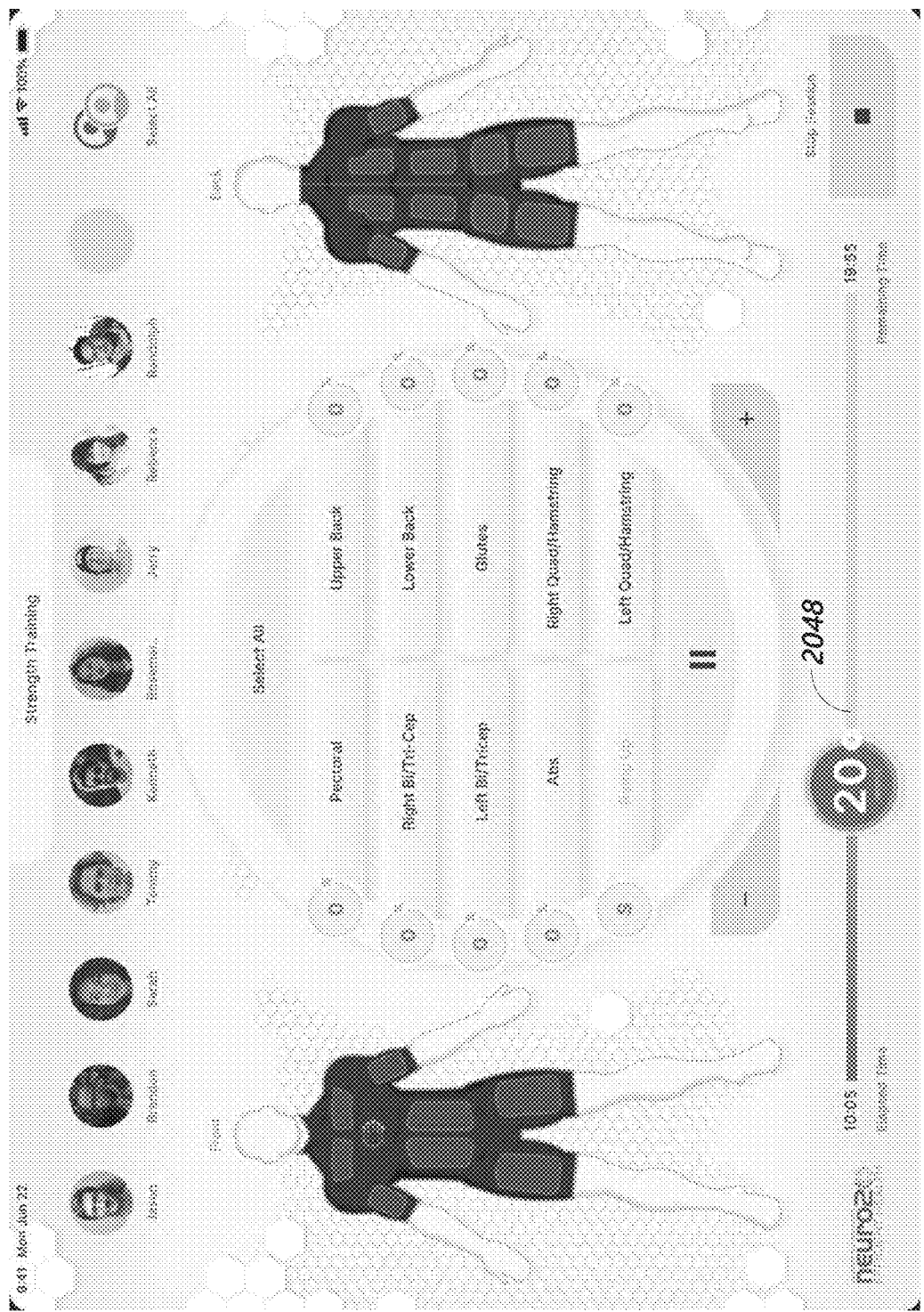

After the alerts are cleared, the session can resume for all participants. During normal operation, as shown in FIG. 34B, no alerts are indicated and all participant systems are functioning. A session timer 2048 moves to indicate the time remaining in the session, and the stimulation paradigm is provided. If alerts arise during the session, the screen displays the alert and, in some implementations, stops stimulation and/or the session as discussed above.

Figure 35A:
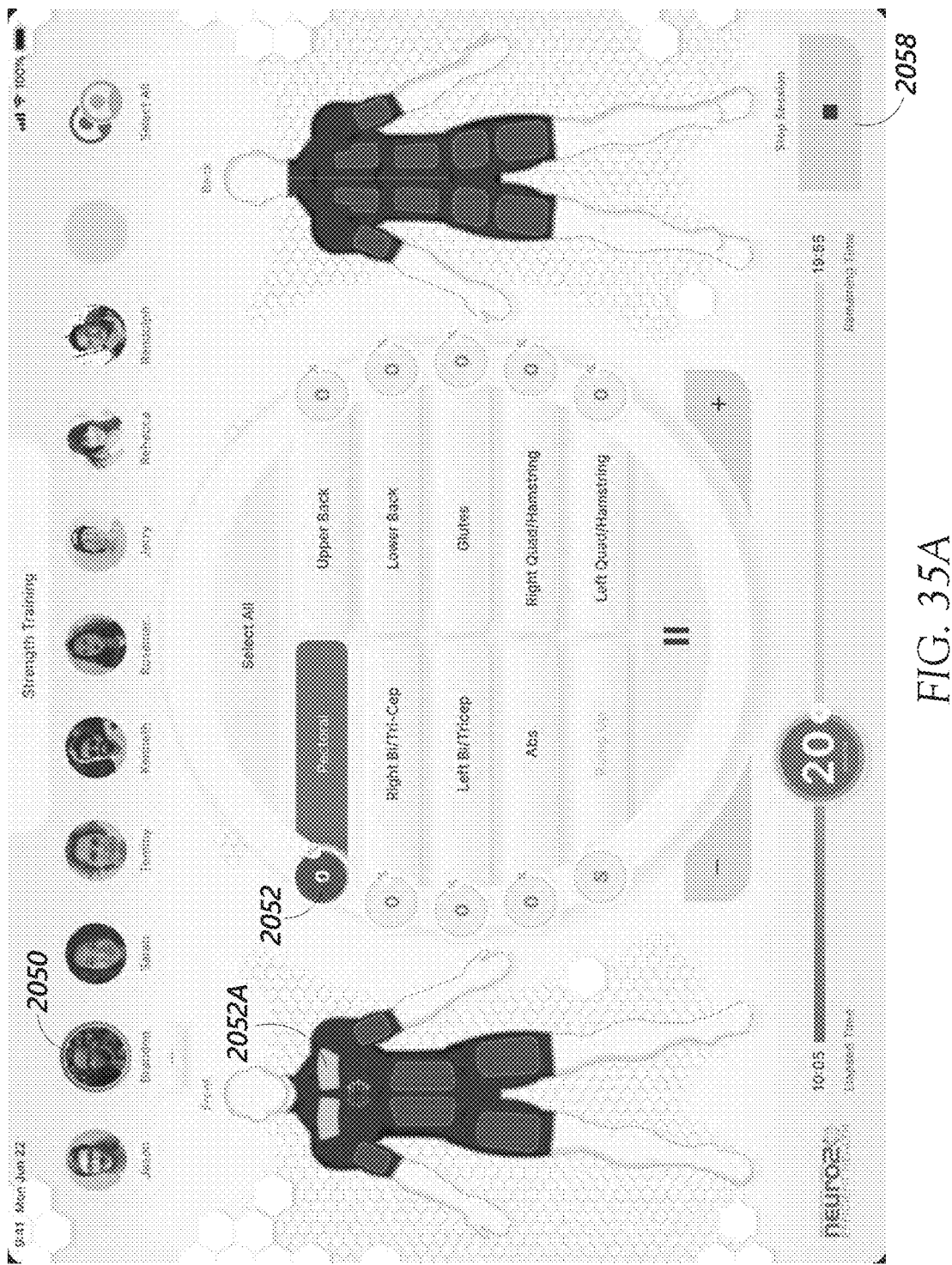
FIGS. 35A and 35B illustrate an implementation of the platform software session adjustments available to a practitioner.
Figure 35B:
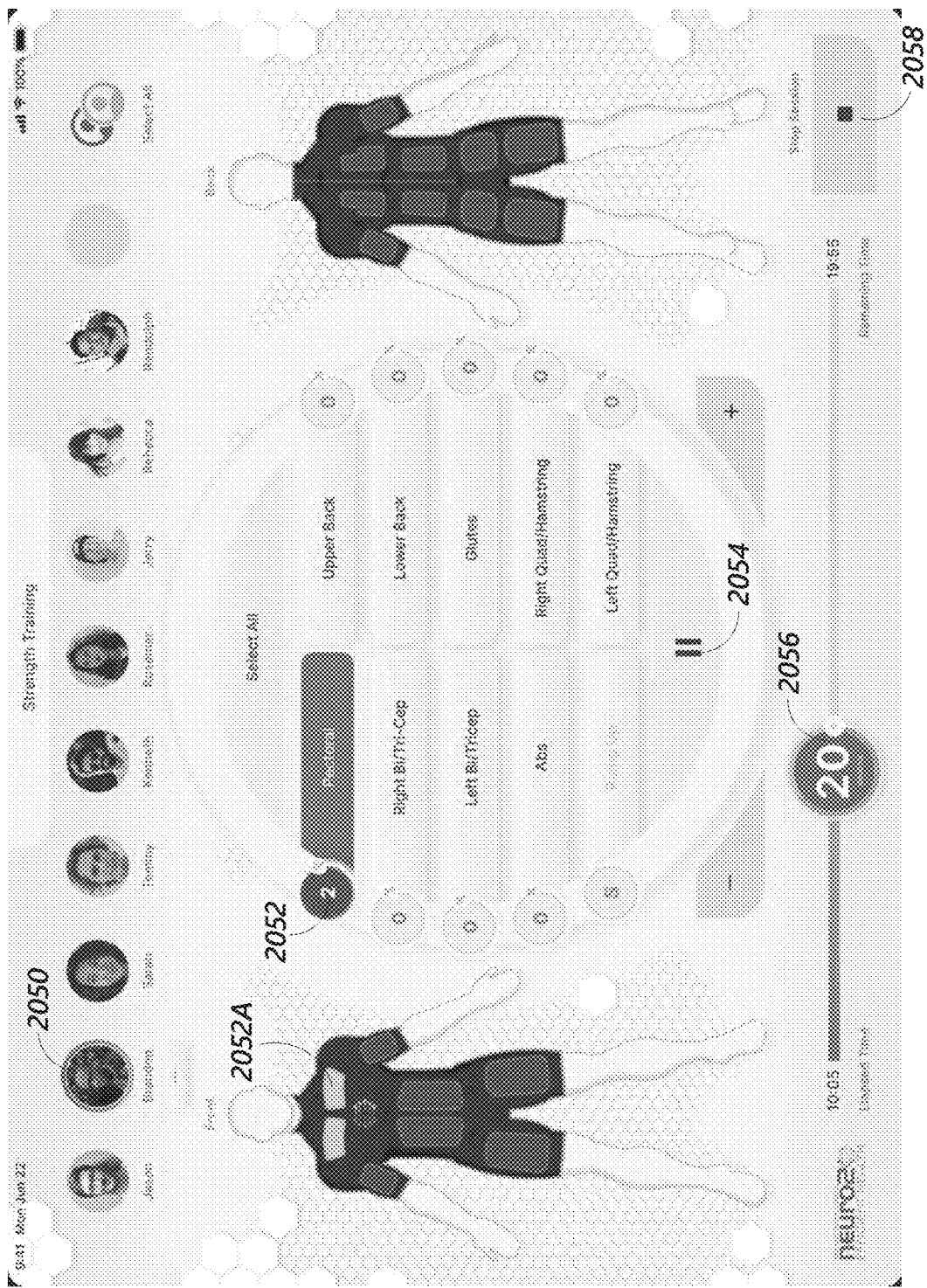
Figure 36:
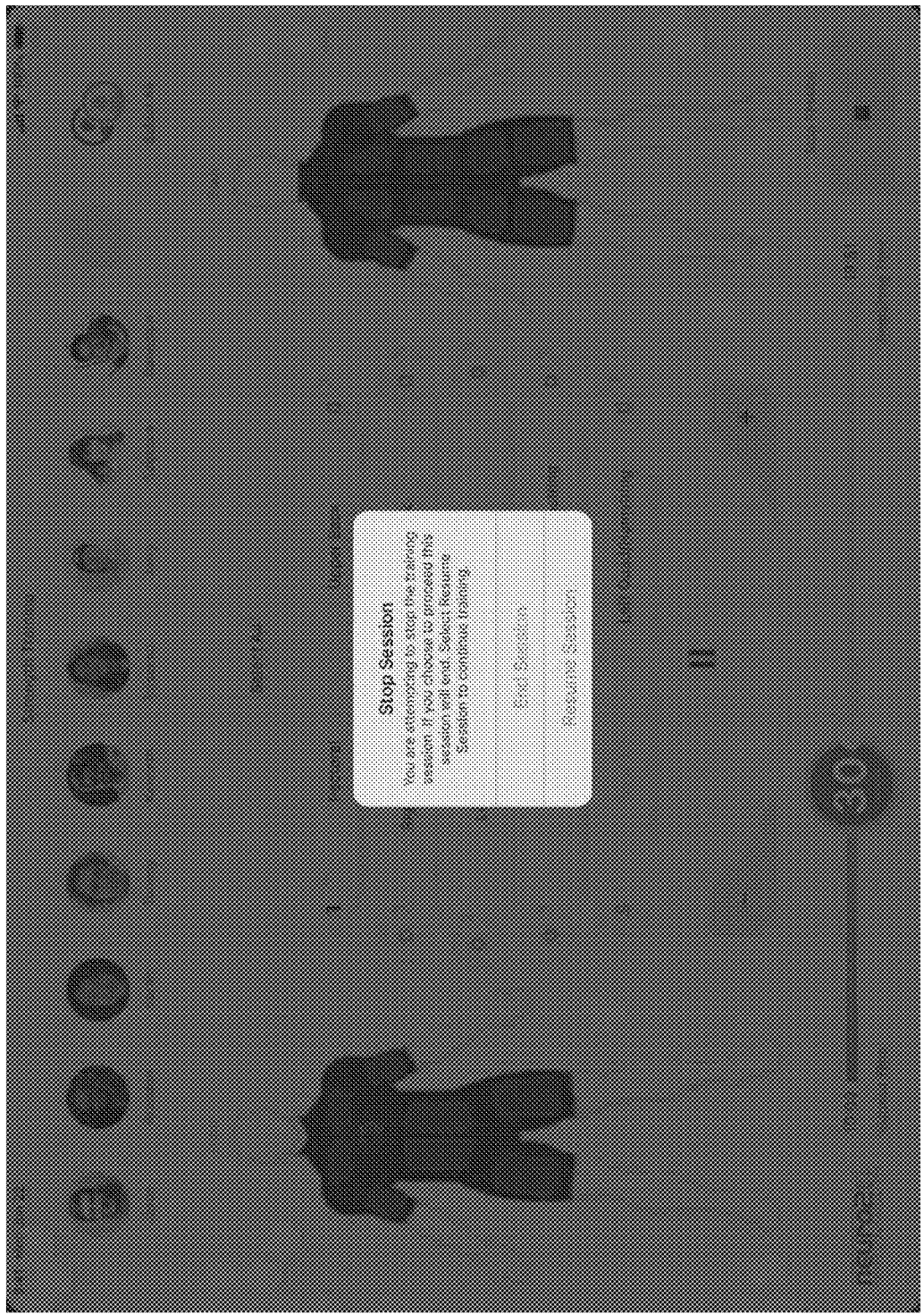
FIG. 36 illustrates an implementation of the platform software function to end a session early.

In this implementation, the practitioner can adjust an individual user's settings during the session. For example, as illustrated in FIG. 35A, the practitioner can adjust the stimulation level 2052 of an electrode 2052A for a user 2050. Stimulation levels can be adjusted up or down or stopped. For example, as shown in FIG. 35B, the stimulation level 2052 of a pectoralis electrode 2052A is adjusted up for one user 2050. With continued reference to FIGS. 35A-B, the session display also allows the practitioner to pause the session with a pause button 2054, which halts stimulation and the progress of timer 2056. The practitioner also has the ability to end the session early with a stop button 2058. As illustrated in FIG. 36, in some implementations, the stop button 2058 requires a confirmation from the practitioner to end a session before the allotted time.

Figure 37A:
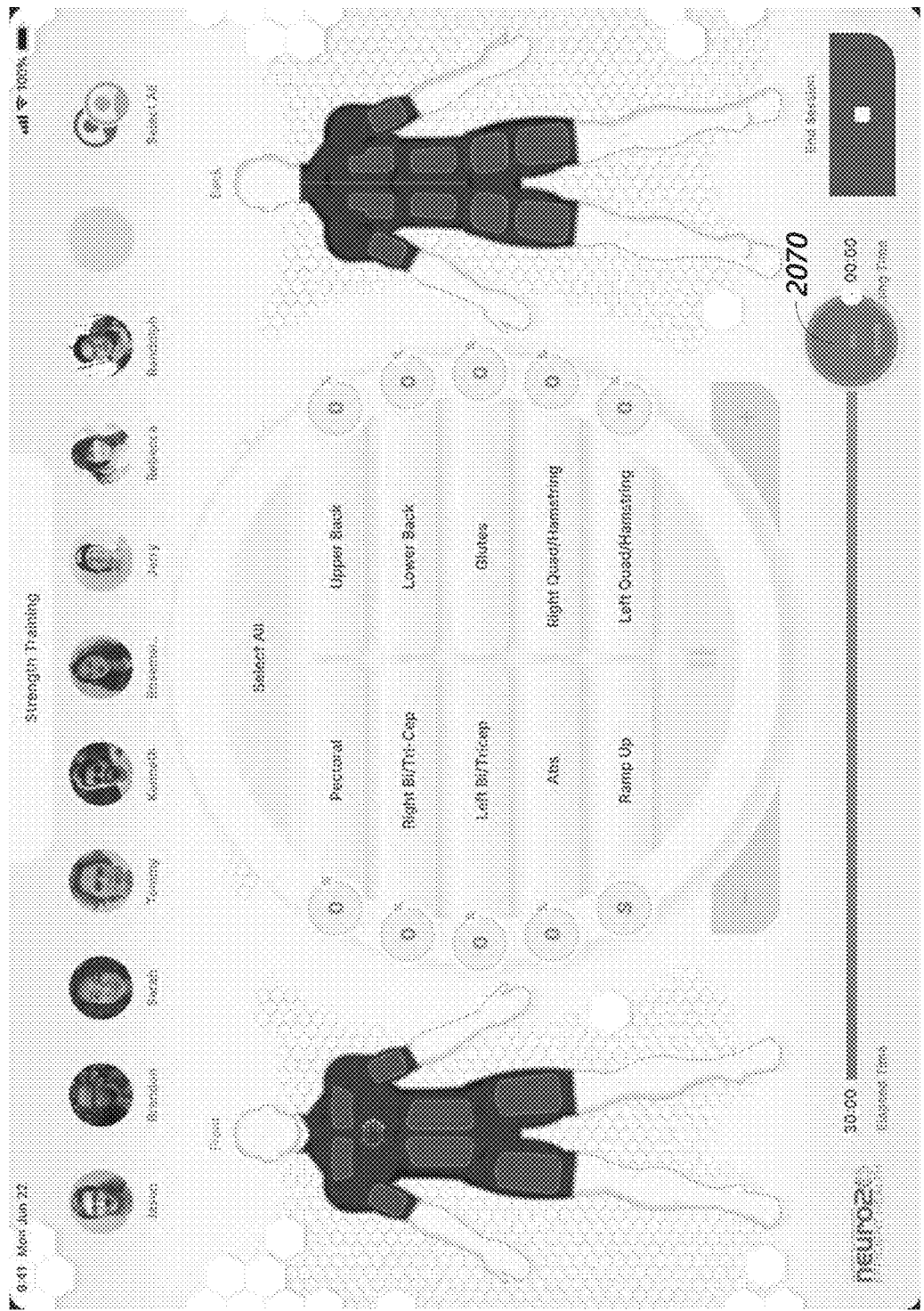
FIGS. 37A and 37B illustrate an implementation of the platform software function to end a session normally with confirmation.
Figure 37B:

In this example implementation, the stimulation patterns are delivered to the clients until the session is completed. As illustrated in FIG. 37A, in some implementations, a session is complete when the timer indicates that the session duration, selected as shown in FIG. 33, has elapsed 2070. In some implementations, the session is complete when a pre-selected number of repetitions, sets, or cycles has been completed. In some implementations, the session is complete when a condition is met, for example when fatigue is detected by one or more sensors 7, 20. In some implementations, a session is "endless" and continues until the participant and/or practitioner ends the session. After the session ends, in some implementations the software 150 can allow the practitioner to exit the training or begin a new session with the same group of clients, as shown in FIG. 37B. In some implementations, the software 150 disables the controller 120 after a session ends. In some implementations, the software 150 continues to collect sensor data after the session is completed.

The example discussed above and shown in FIGS. 20-37 is an illustrative implementation of a practitioner system. Personal or home use systems are also contemplated. In personal use implementations, the system, including suit 110, stimulation control box 122 with controller 120, and software 150, is designed for individual residential use. The home system can be similar in some or many respects to the practitioner system discussed above. In some implementations, the home system can be monitored remotely by a licensed healthcare practitioner. In some implementations, data is transmitted to the healthcare practitioner for review.

As mentioned above, in some implementations of the home system, the user accesses modified software using an application on a desktop or laptop computer, tablet, phone or other mobile computing device. In some implementations, the software 150 is modified to limit the number of control boxes, maximum and/or minimum stimulation parameter ranges, number and type of available programs, session duration, and/or number of sessions. For example, in some implementations, the modified home use software allows users to select one pre-installed training program and recovery mode, select the limits of maximum intensity percentages, and schedule the training session start and end time. In some implementations, the software 150 limits the operational time, for example not to exceed 15 minutes per day, 30 minutes per day, 60 minutes per week, three hours per week, twenty days per month, or other appropriate limits. In some implementations, additional features can be accessed, blocked, or adjusted. For example, after a client completes a therapy course over a prescribed number of months, the software can unlock additional time, modes, and/or maximum intensity percentage. These examples are illustrative, and not intended to be limiting. The numbers may vary slightly (e.g., by 5-10%) in some implementations. In other implementations, they are exact.

Stimulation Patterns

As indicated above, the system provides a variety of stimulation modes. The delivered stimulation parameters and session parameters are tailored for the purpose of each mode. For all modes, stimulation is generated by a series of repeated pulses. In some implementations, the pulses are generally uniform, and can be delivered at a varying frequency. For example, in some implementations, each uniform pulse is a symmetric square wave, made of two equal phases with 0 microseconds between phases. The equal phases can be 20-200 microseconds each. Because the pulse is biphasic and symmetrical, electricity flows in both directions and is balanced. In accordance with several implementations, as there is no net ion flow, this stimulation activates nerves and muscles but does not create a residual build-up of ions. In some implementations, the pulses are uniform triphasic pulses or pulse trains. In some implementations, the pulses are monophasic pulses. In some implementations, the pulses are non-uniform charge-balanced biphasic or triphasic pulses. In some implementations, the pulse trains combine different waveforms to achieve a desired result (e.g., motion, static contraction, increased circulation, cutaneous and/or haptic feedback, etc.).

These uniform pulses are grouped into pulse trains. A pulse train is a set of pulses delivered at a frequency for a period of time (the "on" time) followed by a delay (or an "off" time). In some implementations, a pulse train is designed to provide cutaneous and/or haptic feedback at one or more electrodes 1. For example, haptic feedback stimulation can be provided to simulate sensory interaction with virtual objects, or to allow multiple session participants to virtually interact with one or more other participants. Cutaneous feedback can be used in addition to or instead of other feedback, for example in place of or with the visible and/or audio feedback cues discussed below. In some implementations, the feedback stimulation can be provided by the same electrode(s) 1 as the muscle stimulation. In some implementations, the feedback can be provided by one or more dedicated feedback electrodes 1, which may be identical to the muscle stimulation electrodes 1 in some or all respects. For example, a suit 110 may include one or more additional electrodes 1 in an area separate from electrodes 52-86 discussed above. In some implementations, a sensory electrode 1 can be included in an area of a suit 110 designed to contact a side, neck, sternum, chest, back, wrist, or other location on the body of the wearer.

For many implementations for generating muscle contractions, the frequency and/or timing (the on/off times, or a duty cycle) is adjustable by the practitioner, as discussed above. The stimulation output may have an amplitude between 0 and 200 mA. The stimulation output may be constant current type and have a frequency range of between 1 and 100 Hz. The stimulation output pulse width may vary between 75 and 180 microseconds. In some implementations, the output voltage range is between 20 and 60 volts. The stimulation output pulse ramp up and down may range from 0.25 seconds to 0.75 seconds, as desired and/or required. The ramp up may be toggled between three discrete levels of abrupt, medium and gentle ramp up and ramp down.

Stimulation parameters (e.g., amplitude, frequency, duration of activation and relaxation phases) may be designed (e.g., pre-programmed) to correlate to coordinated activation of particular muscles at different steps of a particular motion so as to tailor the stimulation program to enhance or maximize effects corresponding to a particular training or recover motion or program. In some implementations, the stimulation patterns are based on a kinetic analysis of body parts during various motions so as to provide coordinate activation of muscles throughout a particular motion (e.g., pitching a baseball, swinging a baseball bat, swinging a golf club, kicking a ball, running, cycling, etc.). In some implementations, stimulation patterns can simultaneously activate multiple muscle groups with one or more electrodes to induce a coordinated movement.

In one example stimulation mode, stimulation is provided to induce muscle and/or nerve stimulation during cycling training on a stationary bicycle. The cycling mode is programmed to stimulate the quadriceps and gluteal muscles, for example via electrodes 64, 66, 80, and 82, of each leg of the wearer of the suit 110. In this non-limiting example, the quadriceps and gluteal muscles can be activated in a left leg via electrodes 66 and 80 for a duration, and then the quadriceps and gluteal muscles can be activated in a right leg via electrodes 64 and 82 for the same duration. The duration of activation determines the cycling speed. In some cycling implementations, the left leg and right leg activation times can overlap, while in other implementations the activation times can include a delay between them. In some implementations, the quadriceps and gluteal muscles are started and/or stopped together, while in other implementations, the muscles are activated and/or stopped separately with a time of overlap where they are active together. In some implementations, the hamstrings are also activated during the cycle by sending stimulation signals to the hamstring electrodes, such as electrodes 84 and 86, of the suit 110. Concentric contractions can also be stimulated for all or part of the full pedal cycle. One example implementation of a slow and fast cycling mode is represented in Table 1 below. However, other ranges of timing patterns or parameters may also be used as desired and/or required. Each cycle is repeated immediately after conclusion of the prior cycle, and the pattern continues for a session duration, for example 10, 12, 15, 20, 25, 30 minutes or other appropriate time.

In another example stimulation mode, stimulation is provided to induce muscle and/or nerve stimulation during walking, jogging, running and/or sprinting movements (collectively, ambulation movements). The ambulation mode is programmed to stimulate the quadriceps muscles and gluteal muscles together on the right side, and then together on the left side, with a delay between the left and right. The hamstring muscles are activated during the delay period of the quadriceps muscles on the same side, and hamstring stimulation is stopped before the quadriceps muscles are stimulated again. For example, in some implementations, the stimulation controller 120 is programmed to stimulate the quadriceps and gluteal muscles of a left leg via electrodes 66 and 80 for a duration and then after a delay, to stimulate the quadriceps and gluteal muscles of the right leg via electrodes 64 and 82 for the same duration. The controller 120 can also provide stimulation to the hamstring muscles of the right leg via electrode 86 after the right quadriceps are off, and stimulation to the hamstring muscles of the left leg via electrode 84 after the left quadriceps are off.

The duration of the activation and the intervening delays determine the ambulation speed. For example, in some implementations of a sprinting mode, each cycle can be programmed for about 280 ms, with the quadriceps and gluteal muscles of each side (left and right) activated for 25% (about 70 ms) of the cycle. The hamstrings can be activated for about 60 ms after the respective quadriceps stimulation stops. This cycle may be repeated for a rep duration of 20 seconds with a rest/recover of 40 seconds, and the mode concludes after 6 reps. In some implementations of a running mode, each cycle is extended to 320 ms and the duration of the entire mode is also extended to approximately 5 minutes. In some implementations of a jogging mode, each cycle is approximately 640 ms and the duration of the entire mode is approximately 20 minutes. In some implementations of a walking mode, each cycle (step) is 640 ms and the duration of the entire mode is approximately 20 minutes. One example implementation of ambulation modes is represented in Table 2 below. The numbers provided may be approximate and may vary by 5-10% in some implementations. In other implementations, they are exact. Each cycle is repeated immediately after conclusion of the prior cycle, and the pattern continues for a session duration, for example 10, 12, 15, 20, 25, 30 minutes or other appropriate time as discussed above.

TABLE 1

Cycling

| Muscles | Delay (ms) | ON time (ms) | OFF time (ms) |
|---|---|---|---|
| 45 RPM (slow; 1320 ms total each side) | | | |
| Left Quads and Glutes | 0 | 480-560 (e.g., 520) | 750-850 (e.g., 800) |
| Left Hamstrings | 700-900 (e.g., 800) | 340-380 (e.g., 360) | 140-180 (e.g., 160) |
| Right Quads and Glutes | 620-680 (e.g., 660) | 500-540 (e.g., 520) | 120-160 (e.g., 140) |
| Right Hamstrings | 140-180 (e.g., 160) | 340-380 (e.g., 360) | 750-850 (e.g., 800) |
| 80 RPM (fast; 760 ms total each side) | | | |
| Left Quads and Glutes | 0 | 250-350 (e.g., 300) | 420-500 (e.g., 460) |
| Left Hamstrings | 420-500 (e.g., 460) | 150-250 (e.g., 200) | 80-120 (e.g., 100) |
| Right Quads and Glutes | 350-420 (e.g., 380) | 250-350 (e.g., 300) | 60-100 (e.g., 80) |
| Right Hamstrings | 60-100 (e.g., 80) | 150-250 (e.g., 200) | 460-500 (e.g., 480) |

TABLE 2

Ambulation

| Muscles | Delay (ms) | ON time (ms) | OFF time (ms) |
|---|---|---|---|
| Walk (1000 ms) | | | |
| Left Quads and Glutes | 0 | 200 | 800 |
| Left Hamstrings | 300 | 200 | 500 |
| Right Quads and Glutes | 500 | 200 | 300 |
| Right Hamstrings | 800 | 200 | 0 |
| Jog (640 ms) | | | |
| Left Quads and Glutes | 0 | 200 | 440 |
| Left Hamstrings | 200 | 200 | 240 |
| Right Quads and Glutes | 320 | 200 | 120 |
| Right Hamstrings | 120 | 440 | 80 |
| Run (320 ms) | | | |
| Left Quads and Glutes | 0 | 100 | 220 |
| Left Hamstrings | 100 | 100 | 120 |

TABLE 2-continued

Ambulation

| Muscles | Delay (ms) | ON time (ms) | OFF time (ms) |
|---|---|---|---|
| Right Quads and Glutes | 160 | 100 | 60 |
| Right Hamstrings | 60 | 260 | 40 |
| Sprint (280) | | | |
| Left Quads and Glutes | 0 | 70 | 210 |
| Left Hamstrings | 70 | 60 | 150 |
| Right Quads and Glutes | 140 | 70 | 70 |
| Right Hamstrings | 210 | 60 | 10 |

In another example stimulation mode, stimulation is provided to induce muscle and/or nerve stimulation during swinging motions for training, for example swinging a bat, racquet, club (e.g., golf club), or other athletic or training equipment. For many swing motions, the extension of the stride knee (for example, the left quadriceps of a right-handed hitter) and bilateral hips (for example, the right gluteus maximus and right and left gluteus medius of a right-handed hitter) as well as the head speed of the club, bat, or racquet (generated by, for example, left lumbar paraspinals, left posterior deltoid and triceps plus right pectoralis and triceps for right-handed hitters) are paramount for bat speed and power. Thus, in many implementations, the most demanding instant for the trunk and spine is after ball contact for swinging. The swinging stimulation mode can be programmed in a pattern to induce repeated smooth swings by independently activating these muscles in concert, with appropriate activation onset delays and activation time/duration. An example right-handed batting motion stimulation pattern is represented in Table 3 below. The numbers provided may be approximate and may vary by 5-10% in some implementations. In other implementations, they are exact.

TABLE 3

Swinging

| Muscles | Delay (ms) | ON time (ms) | Total (ms) |
|---|---|---|---|
| Right Quadriceps and Gluteus Medius | | 180 | 180 |
| Left Hamstrings | | 120 | 120 |
| Left Gluteus Medius | 40 | 280 | 320 |
| Left Quadriceps | 100 | 220 | 320 |
| Right Gluteus Maximus | 60 | 220 | 280 |
| Left Lumbar paraspinals | 60 | 260 | 320 |
| Right Lumbar paraspinals | 220 | 100 | 320 |
| Left Abdominal muscles | 60 | 260 | 320 |
| Left Posterior Deltoid and Infraspinatus | 100 | 180 | 280 |
| Left Triceps | 140 | 140 | 280 |
| Right Pectoralis | 140 | 140 | 280 |
| Right Triceps | 160 | 120 | 280 |

In another example stimulation mode, stimulation is provided to induce muscle and/or nerve stimulation during a throwing motion for training. In many implementations, the throw mode is designed for an overhand single-arm throw, such as a baseball pitch, fielding throw, or football pass. Other implementations, such as basketball pass, shot put throw, frisbee toss, javelin, etc. are also contemplated. Some throw modes are designed to improve athletic performance, while others (for example, bean bag toss, hatchet toss) are designed to improve mobility, flexibility, and/or strength in a more entertaining and engaging way than simple repetitive stretches or motions.

Overhand single-arm throw motions can be subdivided into several phases, for example, a wind up, stride, trunk rotation and arm cock, arm acceleration, arm deceleration, and follow-through. In accordance with several implementations, each phase requires coordinated activation of muscles, as discussed below. Other throw motions can similarly be subdivided into phases for easier control, analysis, programming, and/or adjustment.

In the example implementation of an overhand throw discussed here, the wind up is a balance and positioning maneuver, not a speed and power move. Quadriceps are active allowing the body to drop down during an eccentric contraction followed by a concentric contraction. Power begins in the stride phase. The forward movement of the stride leg is important, but because throwing has no resistance (an open kinetic chain), this phase can include one lower extremity stride forward from the stance and/or the trailing extremity and pelvis dropping down and pushing off with the pelvis initially internally rotated then forcefully externally rotated by the gluteus maximus. The hip is somewhat extended during initial push off, transitioning energy from the ground into the trunk. During trunk rotation and arm cocking, the trunk is still extended and begins to rotate to square the shoulders. This translates energy from the stance leg push off through the pelvis into the trunk and then the shoulder and arm. Arm cocking takes place as the stride begins and requires energy from the infraspinatus and posterior deltoid to stretch the rotator cuff as well as the pectoralis muscles. The biceps flex to bring the elbow into a flexed position. During arm acceleration, subscapularis activation is critical, but in many implementations is not easily accessed by surface stimulation electrodes. The biceps muscle is used to align the elbow. Flexing of the pectoralis internally rotates the shoulder with the subscapularis. Activation of the triceps accelerates the ball and is maximally active both during acceleration and after a brief pause is reactivated during the next phase of arm deceleration. Arm deceleration activates the triceps, infraspinatus, and teres minor to stabilize the shoulder. During follow-through, the deltoid and rotator cuff muscles continue to eccentrically contract to decelerate the shoulder, and the serratus anterior, middle trapezius, and rhomboids work eccentrically to decelerate the scapula bone. The elbow and forearm are decelerated by biceps contraction. Triceps contraction continues to help stabilize the shoulder joint. The most demanding instant for the trunk and spine may be near front foot contact for pitching.

In some implementations, the triceps and infraspinatus muscles may be simultaneously activated by a single electrode. In these designs, during an arm cocking phase, the triceps would not be activated so neither would the infraspinatus be activated. In these implementations, the client can voluntarily active the infraspinatus, or the muscle might not be active with little to no detriment in the training because arm cocking is not a power maneuver. An example right-handed throwing motion pattern is represented in Table 4 below. The numbers provided by be approximate and may vary by 5-10% in some implementations. In other implementations, they are exact.

TABLE 4

Throwing

| Muscles | Delay (ms) | ON (ms) | OFF (ms) | ON (ms) |
|---|---|---|---|---|
| Right Quadriceps | | 280 | 260 | |
| Right Gluteus Maximus | 180 | 120 | 240 | |

TABLE 4-continued

Throwing

| Muscles | Delay (ms) | ON (ms) | OFF (ms) | ON (ms) |
|---|---|---|---|---|
| Left Lumbar Paraspinals | 180 | 220 | 140 | |
| Left Abdominal | 220 | 220 | 100 | |
| Right Abdominal | 260 | 180 | 100 | |
| Right Infraspinatus and Upper Paraspinals | 160 | 80 | 200 | 100 |
| Right Biceps | 180 | 120 | 240 | |
| Right Triceps | 280 | 100 | 60 | 100 |

In another example stimulation mode, stimulation is provided to induce muscle and/or nerve stimulation for strength training. In this implementation, a muscle or group of muscles can be activated for a maximal or near-maximal contraction for a time period, followed by a rest, or relaxation, period. For example, a muscle or group of muscles can be activated at 84 Hz for 3 seconds, followed by 3 seconds of rest, which is repeated. In another example implementation, the muscle(s) activation is 84 Hz for 5 seconds, followed by 2 seconds of rest, which is repeated. As another example, a muscle or group of muscles can be activated at 84 Hz for 180 microseconds, followed by 75 microseconds of rest, which pattern is repeated.

In another example stimulation mode, stimulation can be provided for a massage function. In this implementation, a muscle or group of muscles can be burst-activated activated for a maximal or near-maximal contraction for a short time period, followed by a longer rest period. For example, a muscle or group of muscles can be activated using a pattern of stimulation at 84 Hz for 1 second, followed by 4 seconds of rest, which is repeated. Although the individual activation signals are the same (84 Hz) for both strength training and massage, the timing of the activation and rest provides different functional results. As another example, a muscle or group of muscles can be activated using a stimulation pattern of stimulation at 84 Hz for 180 microseconds, followed by 75 microseconds of rest, which pattern is repeated.

In another example stimulation mode, stimulation is provided to induce muscle and/or nerve stimulation for body toning. In this implementation, again a muscle or group of muscles can be activated for a time period, followed by a rest period. The activation/rest durations are similar to strength training, but the frequency of stimulation is different. In some implementations, the frequency is lower to provide sub-maximal muscle contractions. For example, a muscle or group of muscles can be activated using a pattern of stimulation at 40 Hz for 4 seconds, followed by 4 seconds of rest, which is repeated, or stimulation at 40 HZ for 180 microseconds followed by 75 microseconds of rest. In other implementations, the frequency is very high to provide maximal contraction. For example, a muscle or group of muscles can be activated using a repeating cycle of stimulation at 100 Hz for 5 seconds, followed by 3 seconds of rest or, alternatively, 100 Hz stimulation for 75 microseconds, followed by 180 microseconds of rest.

In another example stimulation mode, stimulation is provided to induce muscle and/or nerve stimulation for cooldown. In this implementation, a muscle or group of muscles can be burst-activated activated for a maximal or near-maximal contraction for a short time period, followed by similarly short rest period. For example, a muscle or group of muscles can be activated at 100 Hz for 1 second (or alternatively 75 microseconds), followed by 1 or 2 seconds of rest. This type of fast-cycling pattern allows the muscles to gradually return to a resting state after competing one or more of the other patterns, and can help reduce muscle soreness and risk of injury.

In another example stimulation mode, stimulation is provided to simulate an environment or condition. In some implementations, stimulation is provided to induce or mimic muscle fatigue or injury. In some implementations, haptic stimulation is provided to mimic interaction with virtual objects, remote users, harsh environments, and the like. In some implementations, this type of stimulation is optionally available in other training modes, such as the modes discussed above.

The timing described herein is exemplary and not intended to limit the available stimulation durations, patterns, rest periods, or session lengths. For example, the activation times and durations can be altered to include an overlap. In some implementations, the overlap can be a timing overlap of an antagonistic muscle or muscle group. For example, the running timing patterns above can include as brief overlap of the quadriceps and gluteal timing. In some implementations, the overlap is 50 ms, 100 ms, 200 ms, 500 ms, 1000 ms, 1%, 2%, 5%, 10%, 12%, 15%, 20%, 25%, 30%, 40%, 50% or other time and/or ratio of contraction. As discussed above, the software 150 can provide mode templates, where the practitioner can adjust each parameter to suit a specific client and/or to meet particular goals. In some implementations, feedback can be provided. For example, in some implementations, an audible and/or visual cue, such as a beep and/or a light, can be used to alert the wearer and/or practitioner that a stimulation pattern (e.g., a cycling rep) is beginning and/or ending. In some implementations, the audible, tactile, haptic, and/or visual cue can be used to provide an alert that an individual movement (e.g., a swing or a throw) is beginning and/or ending. These cues can help clients and practitioners properly position a client's body and/or equipment, decrease the risk of injury, and improve ease of use. In some implementations, the feedback can be adjusted. For example, beep volume and tone can be changed, light color can be changed, and patterns can be selected for both audible and visual feedback. In some implementations, the feedback can be provided with a delay, for example a delay of 500-5000 ms. In some implementations, the control box and/or manager device can be used to pause or stop stimulation after the feedback is provided, for example if the client is improperly positioned or otherwise unready for stimulation. In some implementations, the stimulation pattern automatically repeats for a duration or a number of cycles. In some implementations, the stimulation pattern is "endless" and repeats until the client and/or practitioner stops the program. In some implementations, the stimulation pattern completes one cycle and the client and/or practitioner can selectively repeat the cycle.

For some implementations of the various stimulation modes, the stimulation pattern can include a ramp up and/or ramp down period. In some modes, the ramp applies to the entire session, similar to a warm up and/or cool down period. In some modes, the ramp applies to each pulse train. For example, in the cycling implementations described above, a pulse train can include a ramp up period between 0.1 and 1.0 seconds. Ramp down periods are typically, but not always, shorter and may be eliminated from the stimulation pattern. For all patterns, muscles can be activated individually, in agonist groups, in antagonist pairs, in functional groups, or across the entire suit, depending on the individual goals. In some implementations, core or trunk muscles can be additionally activated at any phase of the pattern or through the entire pattern. For example, abdominal and/or lumbar muscles can be activated during running, sprinting, and/or kicking to enhance stability and/or improve posture. Muscles not included in the desired motion itself can optionally be stimulated during any pattern, for example to increase caloric burn. In each of the rest periods described above, muscles can be activated at a very low level, for example 7 Hz, less than 10 Hz, less than 20 Hz, less than 5 Hz.

The software, including remote software 150 and software or firmware inside control box 122, can also include a calibration circuit. In some implementations, the calibration circuit is used to establish a baseline, a threshold, an offset, a calibration coefficient such as a scaling factor, other calibration parameters, and combinations thereof. A calibration algorithm can be performed for a wearer, a suit 110, and/or a location. For example, a stimulation threshold can be established for a particular wearer with a particular suit 110 in a particular session. At the next session, the new or clean suit 110 can be recalibrated to ensure safety and function. Similarly, calibration can be performed when the control box is moved from one connection area 130 to another (e.g., when the controller is moved from one side of the suit 110 to the other side) to account for the different relationships and geometry between the connected components. In other implementations, calibration optionally can be performed when adding, replacing, or removing sensors, for example sensors 7, 10, in order to establish a baseline. In some implementations, calibration information is stored in a memory of the control box 122. In some implementations, stored calibration information can be selected, altered, or accessed by the practitioner via the manager device 152. In these implementations, the calibration data can be stored and used as part of a user profile. In some implementations, calibration is performed automatically, such as when the system detects a new component connection, on power-up, and/or after a predefined run time. In other implementations, the calibration can optionally be performed at any time via user selection. These examples are illustrative and not intended to be limiting.

In some implementations, the system comprises various features that are present as single features (as opposed to multiple features). For example, in one implementation, the system includes a single suit and a single control box with a stimulation controller. In another implementation, the system includes a single suit, a single control box, and a single remote manager device with software. The suit may form a single, unitary, or integral, construct including the textile suit, electrode(s), signal pathway(s), closure system, and connection area. In some implementations, multiple sensors may be contained in an integrated sensor package. For example, multiple photodetectors can be combined with a thermistor in an integrated sensor package. In some implementations, the control box includes a single integrated package including a stimulation controller, transceiver, charging circuit, and memory. In some implementations, the software is a single software package, while in other implementations the software is made of multiple cooperating modules optionally run on distributed hardware. Multiple features or components are provided in alternate implementations.

In some implementations, the system comprises one or more of the following: a means for muscle stimulation (e.g., electrodes, wires), a means for holding the stimulation means against the muscle or skin (e.g., a garment, belt, strap, band, harness, adhesive), a means for controlling the stimulation (e.g., a software based controller, a hardware based controller, a pre-programmed controller, a dynamically adjustable controller), a means for interfacing with a user (e.g., a button, switch, light, speaker, display, touchscreen, mouse, stylus), a means for biosensing (e.g., electrodes, sensors, signal acquisitioning circuitry, signal processors and pre-processors), and a means for data analysis and storage (artificial intelligence, data sets, memory, removable memory, servers).

Computer Systems

Figure 38:
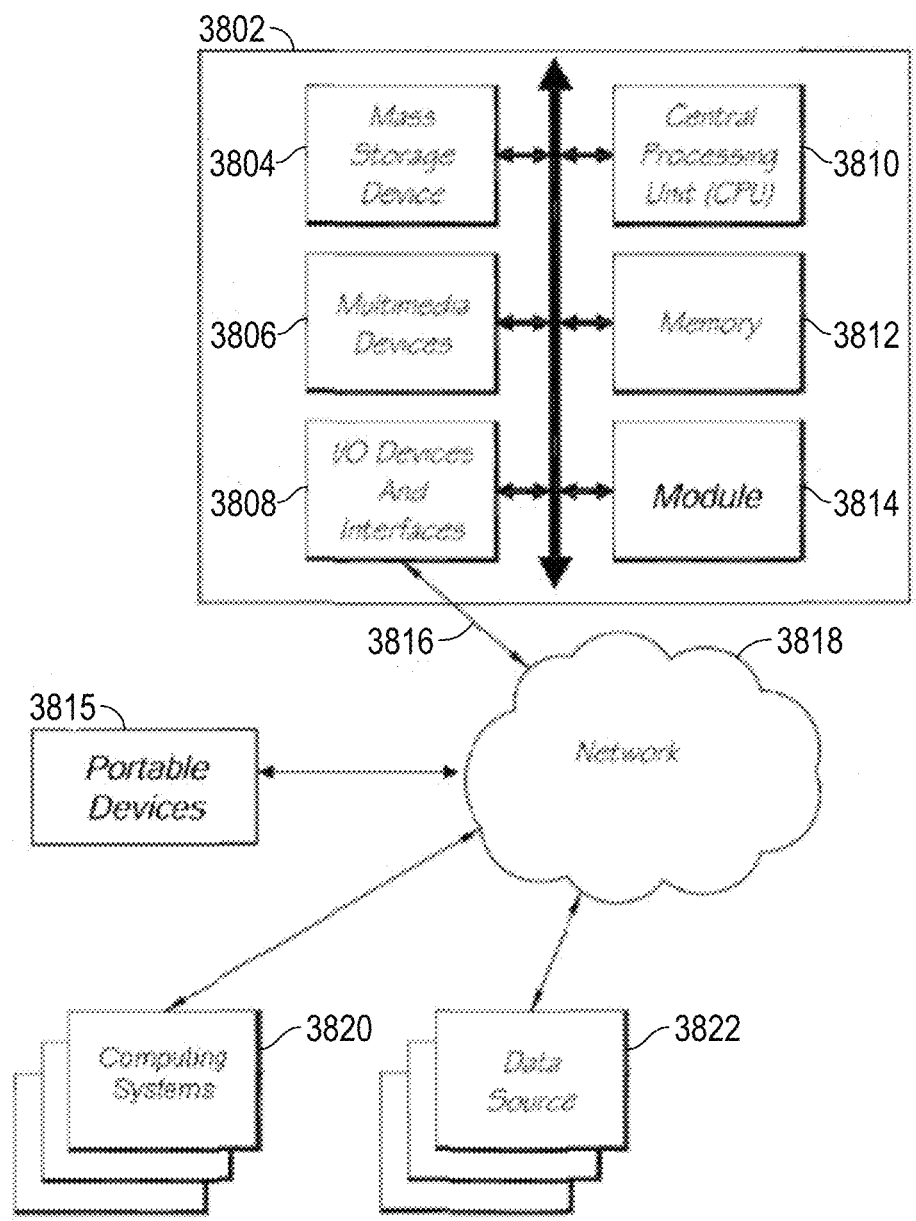
FIG. 38 is a block diagram depicting an implementation of a computer hardware system configured to run software for implementing the systems, methods, and devices disclosed herein.

FIG. 38 is a block diagram depicting an implementation of a computer hardware system configured to run software for implementing one or more implementations of the functional impulse training and rehabilitation systems, methods, and devices disclosed herein.

In some implementations, the systems, processes, and methods described herein are implemented using a computing system, such as the one illustrated in FIG. 38. The example computer system 3802 is in communication with one or more computing systems 3820 and/or one or more data sources 3822 via one or more networks 3818. While FIG. 38 illustrates an implementation of a computing system 3802, it is recognized that the functionality provided for in the components and modules of computer system 3802 may be combined into fewer components and modules, or further separated into additional components and modules.

The computer system 3802 can comprise an electrical stimulation training and rehabilitation management module 3814 that carries out the functions, methods, acts, and/or processes described herein. In some implementations, the electrical stimulation training and rehabilitation management module 3814 carries out some or all of the functions of software 150 discussed above. The electrical stimulation training and rehabilitation management module 3814 can be executed on a computer system 3802 by a central processing unit 3810 discussed further below. In some implementations, computer system 3802 is a separate device. In some implementations, computer system 3802 includes some or all of manager device 152 and/or controller box 122.

In general, the word "module," as used herein, refers to logic embodied in hardware or firmware or to a collection of software instructions, having entry and exit points. Modules are written in a program language, such as JAVA, C or C++, PYPHON or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some implementations, process blocks described herein may be altered, rearranged, combined, and/or omitted.

The computer system 3802 includes one or more processing units (CPU) 3810, which may comprise a microprocessor. The computer system 3802 further includes a physical memory 3812, such as random access memory (RAM) for temporary storage of information, a read only memory (ROM) for permanent storage of information, and a mass storage device 3804, such as a backing store, hard drive, rotating magnetic disks, solid state disks (SSD), flash memory, phase-change memory (PCM), 3D)(Point memory, diskette, or optical media storage device. Alternatively, the mass storage device may be implemented in an array of servers. Typically, the components of the computer system 3802 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 3802 includes one or more input/output (I/O) devices and interfaces 3808, such as a keyboard, mouse, touch pad, and printer. The I/O devices and interfaces 3808 can include one or more display devices, such as a monitor, eyepiece, and/or headset, that allows the visual presentation of data to a user. More particularly, a display device provides for the presentation of GUIs as application software data, and multi-media presentations, for example. The I/O devices and interfaces 3808 can also provide a communications interface to various external devices. The computer system 3802 may comprise one or more multi-media devices 3806, such as speakers, video cards, graphics accelerators, and microphones, for example.

The computer system 3802 may run on a variety of computing devices, such as a server, a Windows server, a Structure Query Language server, a Unix Server, a personal computer, a laptop computer, and so forth. In other implementations, the computer system 3802 may run on a cluster computer system, a mainframe computer system and/or other computing system suitable for controlling and/or communicating with large databases, performing high volume transaction processing, and generating reports from large databases. The computing system 3802 is generally controlled and coordinated by an operating system software, such as z/OS, Windows, Linux, UNIX, BSD, SunOS, Solaris, MacOS, or other compatible operating systems, including proprietary operating systems. Operating systems control and schedule computer processes for execution, perform memory management, provide file system, networking, and I/O services, and provide a user interface, such as a graphical user interface (GUI) or virtual reality simulation, among other things.

The computer system 3802 illustrated in FIG. 38 is coupled to a network 3818, such as a LAN, WAN, or the Internet via a communication link 3816 (wired, wireless, or a combination thereof). Network 3818 communicates with various computing devices and/or other electronic devices. Network 3818 is communicating with one or more computing systems 3820 and one or more data sources 3822, and optionally additional portable devices 3815. The electrical stimulation training and rehabilitation management module 3814 may access or may be accessed by computing systems 3820 and/or data sources 3822 and/or one or more portable devices 3815 through a web-enabled user access point. Connections may be a direct physical connection, a virtual connection, and other connection type. The web-enabled user access point may comprise a browser module that uses text, graphics, audio, video, and other media to present data and to allow interaction with data via the network 3818.

Access to the electrical stimulation training and rehabilitation management module 3814 of the computer system 3802 by computing systems 3820 and/or by data sources 3822 and/or by portable devices 3815 may be through a web-enabled user access point such as the computing systems' 3820 or data source's 3822 or portable device's 3815 personal computer, cellular phone, smartphone, laptop, tablet computer, e-reader device, audio player, or another device capable of connecting to the network 3818. Such a device may have a browser module that is implemented as a module that uses text, graphics, audio, video, and other media to present data and to allow interaction with data via the network 3818.

The output module may be implemented as a combination of an all-points addressable display such as a cathode ray tube (CRT), a liquid crystal display (LCD), a plasma display, or other types and/or combinations of displays. The output module may be implemented to communicate with input devices 3808 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another implementation, a user may interact with the system more directly such as through a system terminal connected to the score generator without communications over the Internet, a WAN, or LAN, or similar network.

In some implementations, the system 3802 may comprise a physical or logical connection established between a remote microprocessor and a mainframe host computer for the express purpose of uploading, downloading, or viewing interactive data and databases on-line in real time. The remote microprocessor may be operated by an entity operating the computer system 3802, including the client server systems or the main server system, and/or may be operated by one or more of the data sources 3822 and/or one or more of the computing systems 3820 and/or one or more of the portable devices 3815. In some implementations, terminal emulation software may be used on the microprocessor for participating in the micro-mainframe link.

In some implementations, computing systems 3820 who are internal to an entity operating the computer system 3802 may access the electrical stimulation training and rehabilitation management module 3814 internally as an application or process run by the CPU 3810.

In some implementations, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a web site and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 3802 may include one or more internal and/or external data sources (for example, data sources 3822). In some implementations, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 3802 may also access one or more databases 3822. The databases 3822 may be stored in a database or data repository. The computer system 3802 may access the one or more databases 3822 through a network 3818 or may directly access the database or data repository through I/O devices and interfaces 3808. The data repository storing the one or more databases 3822 may reside within the computer system 3802.

Figure 39:
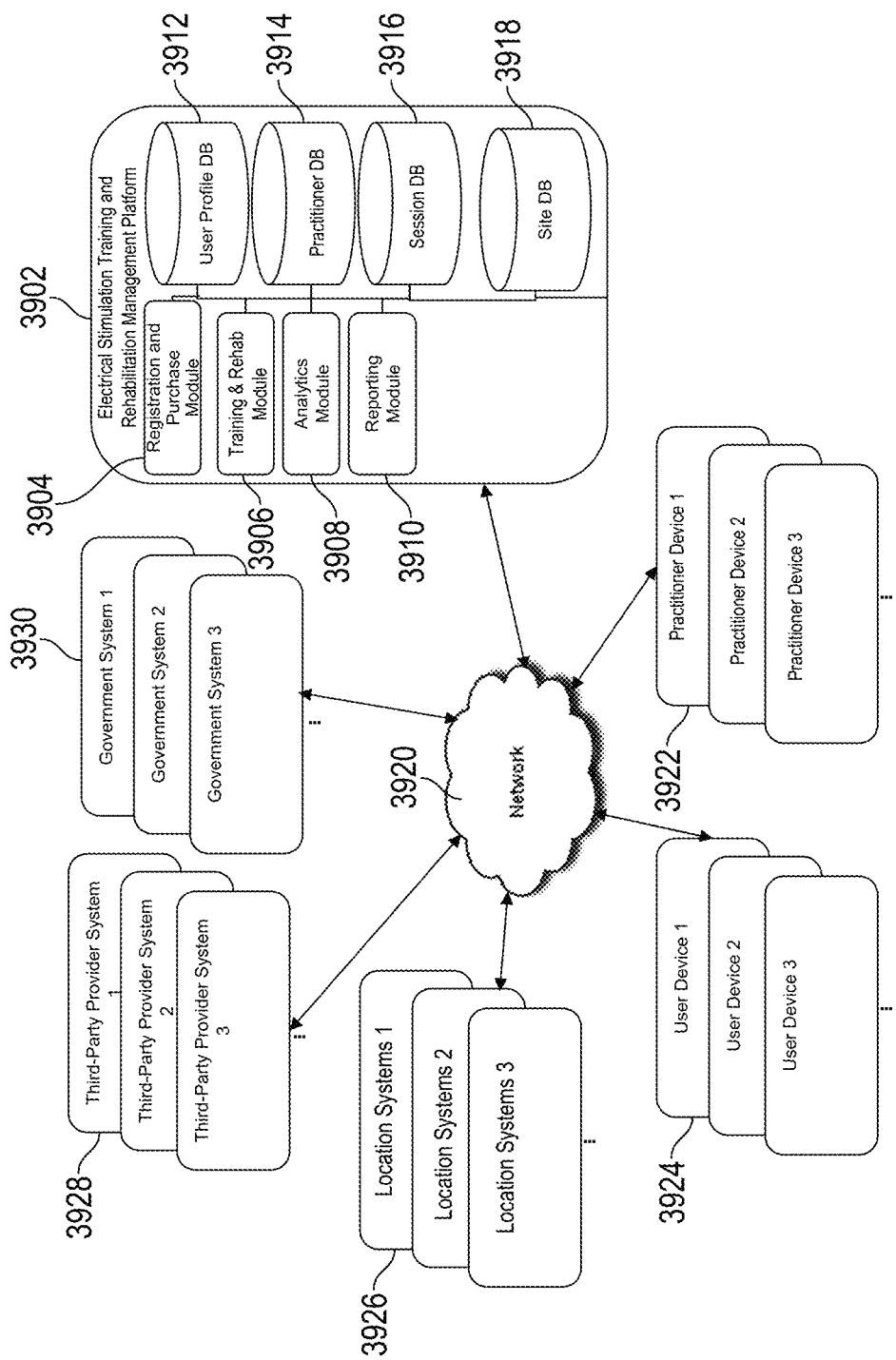
FIG. 39 is a block diagram illustrating an example implementation of a computer system configured to run software for implementing one or more implementations of the electrical stimulation training and rehabilitation management systems, methods, and devices disclosed herein

FIG. 39 is a block diagram illustrating an example implementation of a computer system configured to run software for implementing one or more implementations of the electrical stimulation training and rehabilitation management systems, methods, and devices disclosed herein. In some implementations, the various systems, methods, and devices described herein may also be implemented in decentralized systems such as, for example, blockchain applications. For example, blockchain technology may be used to maintain user profiles, proctor profiles, session results, session site databases, and/or financing databases or ledgers, dynamically generate, execute, and record training and rehabilitation plan agreements, perform searches, conduct client-practitioner matching, determine pricing (such as session prices, hardware prices, and/or session mode access prices), and conduct any other functionalities described herein.

In some implementations, an electrical stimulation training and rehabilitation management platform 3902 may be comprised of a registration and purchase module 3904, a training and/or rehabilitation module 3906, an analytics module 3908, and a reporting module 3910. The electrical stimulation training and rehabilitation management platform 3902 may also comprise a user profile database 3912, a practitioner database 3914, a session database 3916, and/or a site database 3918. The electrical stimulation training and rehabilitation management platform 3902 can be connected to a network 3920. The network 3920 can be configured to connect the electrical stimulation training and rehabilitation management platform 3902 to one or more practitioner devices 3922 (such as manager device 152), one or more user devices 3924 (such as control box 122), one or more location systems 3926 (such as homes, gyms, athletic facilities, rehabilitation facilities, aircraft, space stations, and the like) one or more third-party provider systems 3928, and/or one or more government systems 3930.

The registration and purchase module 3904 may function by facilitating client and/or practitioner registration through one or more registration interfaces and in conjunction with the user database 3912, store user registration data. The training and/or rehabilitation module 3906 may be configured to allow a client and/or user to initiate and complete a training and/or rehabilitation session or visit with a practitioner through a series interfaces, as described herein. The analytics module 3908 may be configured to dynamically analyze client performance across a given population stored in the session database 3916 and provide structured data of the results. The reporting module 3910 may function by dynamically and automatically reporting results to medical records, clinicians, government entities, patients/clients, and third parties using one or more interfaces, such as one or more application programming interfaces. Each of the modules can be configured to interact with each other and the databases discussed herein.

Additional Implementations

In the foregoing specification, the invention has been described with reference to specific implementations thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain implementations and examples, it will be understood by those skilled in the art that the invention extends beyond the specifically disclosed implementations to other alternative implementations and/or uses of the invention and obvious modifications and equivalents thereof. In addition, while several variations of the implementations of the invention have been shown and described in detail, other modifications, which are within the scope of this invention, will be readily apparent to those of skill in the art based upon this disclosure. It is also contemplated that various combinations or sub-combinations of the specific features and aspects of the implementations may be made and still fall within the scope of the invention. It should be understood that various features and aspects of the disclosed implementations can be combined with, or substituted for, one another in order to form varying modes of the implementations of the disclosed invention. Any methods disclosed herein need not be performed in the order recited. Thus, it is intended that the scope of the invention herein disclosed should not be limited by the particular implementations described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every implementation.

As used herein, "system," "instrument," "apparatus," and "device" generally encompass both the hardware (for example, mechanical and electronic) and, in some implementations, associated software (for example, specialized computer programs for graphics control) components.

It is to be understood that not necessarily all objects or advantages may be achieved in accordance with any particular implementation described herein. Thus, for example, those skilled in the art will recognize that certain implementations may be configured to operate in a manner that achieves or optimizes one advantage or group of advantages as taught herein without necessarily achieving other objects or advantages as may be taught or suggested herein.

Each of the processes, methods, and algorithms described in the preceding sections may be embodied in, and fully or partially automated by, code modules executed by one or more computer systems or computer processors including computer hardware. The code modules may be stored on any type of non-transitory computer-readable medium or computer storage device, such as hard drives, solid state memory, optical disc, and/or the like. The systems and modules may also be transmitted as generated data signals (for example, as part of a carrier wave or other analog or digital propagated signal) on a variety of computer-readable transmission mediums, including wireless-based and wired/cable-based mediums, and may take a variety of forms (for example, as part of a single or multiplexed analog signal, or as multiple discrete digital packets or frames). The processes and algorithms may be implemented partially or wholly in application-specific circuitry. The results of the disclosed processes and process steps may be stored, persistently or otherwise, in any type of non-transitory computer storage such as, for example, volatile or non-volatile storage.

Many other variations than those described herein will be apparent from this disclosure. For example, depending on the implementation, certain acts, events, or functions of any of the algorithms described herein can be performed in a different sequence, can be added, merged, or left out altogether (for example, not all described acts or events are necessary for the practice of the algorithms). Moreover, in certain implementations, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the implementations disclosed herein can be implemented as electronic hardware, computer software, or combinations of both. To clearly illustrate this interchangeability of hardware and software, various illustrative components, blocks, modules, and elements have been described herein generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various features and processes described herein may be used independently of one another, or may be combined in various ways. All possible combinations and sub-combinations are intended to fall within the scope of this disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed example implementations. The example systems and components described herein may be configured differently than described. For example, elements may be added to, removed from, or rearranged compared to the disclosed example implementations.

The various illustrative logical blocks and modules described in connection with the implementations disclosed herein can be implemented or performed by a machine, such as a general purpose processor, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another implementation, a processor includes an FPGA or other programmable devices that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some, or all, of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the implementations disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

It will also be appreciated that conditional language used herein, such as, among others, "can," "could," "might," "may," "e.g.," and the like, unless specifically stated otherwise, or otherwise understood within the context as used, is generally intended to convey that certain implementations include, while other implementations do not include, certain features, elements and/or steps. Thus, such conditional language is not generally intended to imply that features, elements and/or steps are in any way required for one or more implementations or that one or more implementations necessarily include logic for deciding, with or without author input or prompting, whether these features, elements and/or steps are included or are to be performed in any particular implementation. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other implementations. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain implementations require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments or implementations shown herein, but are to be accorded the widest scope consistent with this disclosure, the principles and the novel features disclosed herein.

What is claimed is:

1. An electrical stimulation training and rehabilitation system comprising:
   a machine-washable textile body suit comprising:
      a plurality of conductive electrodes positioned along the textile body suit at various locations so as to facilitate neuromuscular stimulation of various regions of a body of a wearer; and
      at least one integrated sensor adapted to collect biodata indicative of a physiological parameter of the wearer;
   a controller configured to provide adjustable stimulation signals to the plurality of conductive electrodes and to receive the biodata;
   a signal pathway connecting the plurality of conductive electrodes to the controller;
   a connector port configured to removably connect the signal pathway to the controller, the connector port comprising an outer circuit board on an outside of the body suit for connecting to the controller, and an inner circuit board on an inside of the body suit connected to the signal pathway; and a manager device configured to wirelessly communicate with the controller and to receive signals from the at least one integrated sensor, and configured to, upon execution of program instructions stored in memory on the manager device, allow a user to adjust a parameter of the stimulation signals, wherein the controller is configured to wirelessly communicate with a user computing device to allow a user to adjust the stimulation signals via a user interface of the user computing device that, upon execution of program instruction stored on a non-transitory computer-readable storage medium, receives input data from the user and generates control signals to the controller responsive to the user input data, wherein the plurality of conductive electrodes includes at least one dry electrode with an antimicrobial agent, wherein the at least one integrated sensor includes at least one of a sweat sensor, a temperature sensor, a wetness sensor, a pH sensor, or a cardiac sensor, and wherein the stimulation signals comprise a pre-set pattern configured to cause a coordinated motion of a person wearing the body suit.

2. The system of claim 1, wherein the plurality of conductive electrodes comprises at least 20 electrodes.

3. The system of claim 1, wherein the plurality of conductive electrodes comprise a plurality of dry electrodes.

4. The system of claim 1, wherein the plurality of conductive electrodes are configured to contact at least body locations corresponding to muscles of the arms, chest, back, and legs when the body suit is worn.

5. The system of claim 1, wherein each of the plurality of conductive electrodes includes an anti-microbial agent.

6. The system of claim 1, wherein the connector port further comprises
flexible wires connecting the outer circuit to the inner circuit.

7. The system of claim 1, wherein the outer circuit includes an outer printed circuit board and the inner circuit includes an inner printed circuit board.

8. The system of claim 1, wherein the outer circuit includes an electrical connector and the connector port includes an outer cover containing the outer circuit.

9. The system of claim 8, wherein the controller is housed in a control box, and the outer cover is shaped to mate with a back of the control box when the controller is connected.

10. The system of claim 1, further wherein:
the signal pathway includes a first connector port on a first side of the textile body suit and a second connector port on a second side of the textile body suit; and
the controller is removably connectable to both the first connector port and second connector port.

11. The system of claim 1, wherein the at least one integrated sensor comprises the cardiac sensor.

12. The system of claim 11, wherein the cardiac sensor is an EKG sensor.

13. The system of claim 1, wherein the at least one integrated sensor comprises the sweat sensor.

14. The system of claim 1, wherein the controller is configured to send the biodata to the user computing device to facilitate monitoring of the physiological parameter.

15. An electrical stimulation training and rehabilitation system comprising:
a machine-washable textile body suit comprising:
a plurality of conductive electrodes positioned along the textile body suit at various locations so as to facilitate neuromuscular stimulation of various regions of a body of a wearer; and
at least one integrated sensor adapted to collect biodata indicative of a physiological parameter of the wearer;
a controller configured to provide adjustable stimulation signals to the plurality of conductive electrodes and to receive the biodata; and
a signal pathway connecting the plurality of conductive electrodes to the controller,
wherein the controller is configured to wirelessly communicate with a user computing device to allow a user to adjust the stimulation signals via a user interface of the user computing device that, upon execution of program instruction stored on a non-transitory computer-readable storage medium, receives input data from the user and generates control signals to the controller responsive to the user input data,
wherein the controller is removably connected to the signal pathway with a connector port,
wherein the connector port further comprises:
an outer circuit on an outside of the body suit for connecting to the controller;
an inner circuit on an inside of the body suit connected to the signal pathway; and
flexible wires connecting the outer circuit to the inner circuit,
wherein the outer circuit includes an electrical connector and the connector port includes an outer cover containing the outer circuit, and
wherein the controller is housed in a control box, and the outer cover is shaped to mate with a back of the control box when the controller is connected.

16. The system of claim 15, further comprising a manager device configured to wirelessly communicate with the controller and to receive signals from the at least one integrated sensor.

17. The system of claim 15, wherein the plurality of conductive electrodes comprises at least one dry electrode.

18. The system of claim 15, wherein the plurality of conductive electrodes are configured to contact at least body locations corresponding to muscles of the arms, chest, back, and legs when the body suit is worn.

19. The system of claim 15, wherein the at least one integrated sensor comprises a heart rate sensor.

20. The system of claim 15, wherein the at least one integrated sensor comprises a sweat sensor.

21. The system of claim 15, wherein the plurality of conductive electrodes comprises at least 20 electrodes.

* * * * *

UNITED STATES PATENT AND TRADEMARK OFFICE
CERTIFICATE OF CORRECTION

| | | |
|---|---|---|
| PATENT NO. | : 11,839,759 B2 | Page 1 of 1 |
| APPLICATION NO. | : 18/187624 | |
| DATED | : December 12, 2023 | |
| INVENTOR(S) | : Finkelstein et al. | |

It is certified that error appears in the above-identified patent and that said Letters Patent is hereby corrected as shown below:

In the Specification

On Column 17, Line 12: Delete "301." and insert -- 30 Ω. --.

On Column 39, Line 7: Delete "3D)(Point" and insert -- 3D XPoint --.

Signed and Sealed this
Twenty-sixth Day of March, 2024

Katherine Kelly Vidal
*Director of the United States Patent and Trademark Office*